(12) United States Patent
Doebler et al.

(10) Patent No.: US 11,473,049 B2
(45) Date of Patent: *Oct. 18, 2022

(54) SYSTEM, APPARATUS AND METHOD FOR MATERIAL PREPARATION AND/OR HANDLING

(71) Applicant: CLAREMONT BIOSOLUTIONS LLC, Upland, CA (US)

(72) Inventors: Robert Doebler, Upland, CA (US); Ali Nadim, San Marino, CA (US); James D. Sterling, Upland, CA (US); Anna Hickerson, Altadena, CA (US); Barbara Erwin, Ontario, CA (US); Denice Woyski, Anaheim, CA (US); Ryan P. Talbot, South Pasadena, CA (US); Bruce Irvine, Glendora, CA (US)

(73) Assignee: CLAREMONT BIOSOLUTIONS, LLC, Upland, CA (US)

( * ) Notice: Subject to any disclaimer, the term of this patent is extended or adjusted under 35 U.S.C. 154(b) by 391 days.

This patent is subject to a terminal disclaimer.

(21) Appl. No.: 16/565,206

(22) Filed: Sep. 9, 2019

(65) Prior Publication Data
US 2020/0002663 A1    Jan. 2, 2020

Related U.S. Application Data

(60) Division of application No. 15/299,059, filed on Oct. 20, 2016, now Pat. No. 10,428,301, which is a
(Continued)

(51) Int. Cl.
*C12M 1/00* (2006.01)
*C12N 1/06* (2006.01)
(Continued)

(52) U.S. Cl.
CPC ............ *C12M 47/06* (2013.01); *C12M 23/28* (2013.01); *C12M 27/00* (2013.01); *C12N 1/066* (2013.01);
(Continued)

(58) Field of Classification Search
None
See application file for complete search history.

(56) References Cited

U.S. PATENT DOCUMENTS

| 2,468,515 A | 4/1949 | Robinson |
| 3,190,568 A | 6/1965 | Freedman et al. |

(Continued)

FOREIGN PATENT DOCUMENTS

| EP | 1 767 630 A1 | 3/2007 |
| JP | 58-158345 U | 10/1983 |

(Continued)

OTHER PUBLICATIONS

Amendment, filed Aug. 21, 2015, for U.S. Appl. No. 12/823,081, Irvine et al., "Capture and Elution of Bio-Analytes via Beads That Are Used to Disrupt Specimens," 9 pages.
(Continued)

*Primary Examiner* — William H. Beisner
(74) *Attorney, Agent, or Firm* — Seed Intellectual Property Law Group LLP

(57) ABSTRACT

Oscillating angularly rotating a container containing a material may cause the material to be separate. Denser or heavier material may unexpectedly tend to collected relatively close to the axis of rotation, while less dense or light material may tend to collect relatively away from the axis of rotation. Oscillation along an arcuate path provides high lysing efficiency. Alternatively, a micromotor may drive an impeller removably received in a container. Lysing may be implemented in batch mode, flow-through stop or semi-
(Continued)

batch mode, or flow-through continuous mode. Lysing particulate material may exceed material to be lysed or lysed material and/or air may be essentially eliminated from a chamber to increase lysing efficiency.

10 Claims, 33 Drawing Sheets

Related U.S. Application Data division of application No. 14/451,015, filed on Aug. 4, 2014, now abandoned, which is a continuation of application No. 12/732,070, filed on Mar. 25, 2010, now abandoned, which is a continuation-in-part of application No. PCT/US2009/030622, filed on Jan. 9, 2009.

(60) Provisional application No. 61/117,012, filed on Nov. 21, 2008, provisional application No. 61/020,072, filed on Jan. 9, 2008.

(51) Int. Cl.
  G01N 1/28 (2006.01)
  G01N 1/40 (2006.01)
  C12M 1/02 (2006.01)

(52) U.S. Cl.
  CPC ............ G01N 1/286 (2013.01); G01N 1/4077 (2013.01); *G01N 2001/4083* (2013.01); *G01N 2001/4088* (2013.01); *G01N 2001/4094* (2013.01)

(56) References Cited

U.S. PATENT DOCUMENTS

| | | | |
|---|---|---|---|
| 3,493,497 A | 2/1970 | Pretorius et al. | |
| 3,704,864 A * | 12/1972 | Lee | B01F 7/162 366/205 |
| 4,261,828 A | 4/1981 | Brunner et al. | |
| 4,307,846 A | 12/1981 | Spelsberg | |
| 4,683,195 A | 7/1987 | Mullis et al. | |
| 4,683,202 A | 7/1987 | Mullis | |
| 4,800,159 A | 1/1989 | Mullis et al. | |
| 4,871,675 A | 10/1989 | Coupek et al. | |
| 4,942,018 A | 7/1990 | Munk | |
| 5,229,580 A | 7/1993 | Chioniere | |
| 5,315,993 A | 5/1994 | Alcala | |
| 5,366,395 A | 11/1994 | Mostaghel et al. | |
| 5,374,522 A | 12/1994 | Murphy et al. | |
| 5,464,773 A | 11/1995 | Melendez et al. | |
| 5,475,610 A | 12/1995 | Atwood et al. | |
| 5,720,552 A * | 2/1998 | Schindlegger | A47G 19/2205 366/197 |
| 5,733,776 A | 3/1998 | Barngrover et al. | |
| 5,824,517 A | 10/1998 | Cleuziat et al. | |
| 6,017,698 A | 1/2000 | Bienhaus et al. | |
| 6,084,683 A | 7/2000 | Bruno et al. | |
| 6,369,893 B1 | 4/2002 | Christel et al. | |
| 6,386,844 B1 | 5/2002 | Chen et al. | |
| 6,440,725 B1 | 8/2002 | Pourahmadi et al. | |
| 6,455,287 B1 | 9/2002 | Jem | |
| 6,479,277 B2 | 11/2002 | Duncan | |
| 6,536,938 B2 * | 3/2003 | Zhou | C12M 23/38 366/273 |
| 6,680,025 B2 | 1/2004 | Hearst et al. | |
| 6,740,518 B1 | 5/2004 | Duong et al. | |
| 6,976,383 B2 | 12/2005 | Petro et al. | |
| 7,315,376 B2 | 1/2008 | Bickmore, Jr. et al. | |
| 7,892,491 B2 | 2/2011 | Kim et al. | |
| 8,153,064 B2 | 4/2012 | Doebler, II et al. | |
| 8,852,862 B2 | 10/2014 | Wu et al. | |
| 9,260,475 B2 | 2/2016 | Irvine et al. | |
| 9,873,860 B2 * | 1/2018 | Irvine | C12N 1/066 |
| 10,801,001 B2 * | 10/2020 | Brown | C12M 3/08 |
| 2001/0012612 A1 | 8/2001 | Petersen et al. | |
| 2001/0043508 A1 | 11/2001 | Zhou | |
| 2002/0066812 A1 * | 6/2002 | Gazeau | C12M 47/06 241/66 |
| 2002/0109844 A1 | 8/2002 | Christel et al. | |
| 2002/0146836 A1 | 10/2002 | Neilson et al. | |
| 2002/0146840 A1 | 10/2002 | Hage et al. | |
| 2002/0155619 A1 | 10/2002 | Kurihara et al. | |
| 2003/0082590 A1 | 5/2003 | Van Ness et al. | |
| 2003/0104431 A1 | 6/2003 | Van Ness et al. | |
| 2003/0138800 A1 | 7/2003 | Van Ness et al. | |
| 2003/0165911 A1 | 9/2003 | Van Ness et al. | |
| 2004/0031754 A1 | 2/2004 | Pesiri et al. | |
| 2004/0252299 A9 | 12/2004 | Lemmo et al. | |
| 2004/0252582 A1 * | 12/2004 | Bucher | B01F 13/0863 366/273 |
| 2005/0092685 A1 | 5/2005 | Hilhorst et al. | |
| 2005/0156124 A1 | 7/2005 | Tobimatsu | |
| 2005/0269522 A1 | 12/2005 | Farmer et al. | |
| 2006/0019265 A1 | 1/2006 | Song et al. | |
| 2006/0030038 A1 | 2/2006 | Taylor et al. | |
| 2006/0134630 A1 | 6/2006 | Segura et al. | |
| 2007/0035818 A1 | 2/2007 | Bahatt et al. | |
| 2007/0081419 A1 | 4/2007 | Mou | |
| 2007/0248958 A1 | 10/2007 | Jovanovich et al. | |
| 2010/0203521 A1 | 8/2010 | Klapperich et al. | |
| 2012/0009667 A1 | 1/2012 | Peterson et al. | |
| 2016/0186127 A1 | 6/2016 | Irvine et al. | |

FOREIGN PATENT DOCUMENTS

| | | |
|---|---|---|
| JP | 61-139745 U | 8/1986 |
| JP | 64-24999 U | 2/1989 |
| JP | 3-83574 A | 4/1991 |
| JP | 5-68553 A | 3/1993 |
| JP | 7-239292 A | 9/1995 |
| JP | 7-114718 B2 | 12/1995 |
| JP | 8-160140 A | 6/1996 |
| JP | 2650159 B2 | 5/1997 |
| JP | 2710159 B2 | 10/1997 |
| JP | 2000-320698 A | 11/2000 |
| JP | 2001-527220 A | 12/2001 |
| JP | 2002-502311 A | 1/2002 |
| JP | 2002-537868 A | 11/2002 |
| JP | 2003-102476 A | 4/2003 |
| JP | 2003-522521 A | 7/2003 |
| JP | 2004-32458 A | 11/2004 |
| JP | 2005-118009 A | 5/2005 |
| JP | 2005-160428 A | 6/2005 |
| JP | 2005-177606 A | 7/2005 |
| JP | 2007-82548 A | 4/2007 |
| KR | 10-0700093 B1 | 3/2007 |
| WO | 95/25180 A1 | 9/1995 |
| WO | 99/09211 A1 | 2/1999 |
| WO | 99/49081 A2 | 9/1999 |
| WO | 00/28082 A1 | 5/2000 |
| WO | 00/73412 A2 | 12/2000 |
| WO | 2004/040001 A2 | 5/2004 |
| WO | 2008/114025 A1 | 9/2008 |
| WO | 2009/030622 A1 | 3/2009 |
| WO | 2010/151705 A2 | 12/2010 |

OTHER PUBLICATIONS

Amendment, filed Feb. 28, 2013, for U.S. Appl. No. 12/823,081, Irvine et al., "Capture and Elution of Bio-Analytes via Beads That Are Used to Disrupt Specimens," 18 pages.

Amendment, filed Jan. 14, 2014, for U.S. Appl. No. 12/732,070, Doebler et al., "System, Apparatus and Method for Material Preparation and/or Handling," 24 pages.

Amendment, filed Jan. 14, 2015, for U.S. Appl. No. 12/823,081, Irvine et al., "Capture and Elution of Bio-Analytes via Beads That Are Used to Disrupt Specimens," 18 pages.

(56) References Cited

OTHER PUBLICATIONS

Amendment, filed Mar. 3, 2016, for U.S. Appl. No. 14/451,015, Doebler et al., "System, Apparatus and Method for Material Preparation and/or Handling," 10.
Amendment, filed May 22, 2015, for U.S. Appl. No. 12/823,081, Irvine et al., "Capture and Elution of Bio-Analytes via Beads That Are Used to Disrupt Specimens," 8 pages.
Amendment, filed Oct. 25, 2013, for U.S. Appl. No. 12/823,081, Irvine et al., "Capture and Elution of Bio-Analytes via Beads That Are Used to Disrupt Specimens," 19 pages.
Australian Notice of Acceptance, dated Nov. 30, 2016, for Australian Application No. 2010266034, 3 pages.
Australian Patent Examination Report No. 1, dated Feb. 10, 2016, for Australian Application No. 2010266034, 2 pages.
Belgrader et al., "A Minisonicator To Rapidly Disrupt Bacterial Spores for DNA Analysis".
Canadian Office Action, dated Apr. 12, 2016, for Canadian Application No. 2,711,854, 5 pages.
Canadian Office Action, dated Apr. 27, 2016, for Canadian Application No. 2,766,517, 3 pages.
Canadian Office Action, dated Feb. 12, 2015, for Canadian Application No. 2,711,854, 4 pages.
Canadian Office Action, dated Jun. 15, 2017, for Canadian Application No. 2,711,854, 6 pages.
Chisti et al., "Disruption of microbial cells for intracellular products," *Enzyme and Microbial Technology* 8(4):194-204, 1986.
Communication pursuant to Article 94(3) EPC, dated Apr. 4, 2016, for European Application No. 10 792 687.5, 4 pages.
Communication pursuant to Article 94(3) EPC, dated Aug. 2, 2013, for European Application No. 09 700 618.3, 4 pages.
Communication pursuant to Article 94(3) EPC, dated Jun. 10, 2015, for European Application No. 09 700 618.3, 4 pages.
DeAngelis et al., "Solid-phase reversible immobilization for the isolation of PCR products" *Nucleic Acids Research* 23(22):4742-4743, 1995.
Doebler et al., "Arrayed Lyser and Homogenizer Systems With Multiple Agitator Devices," U.S. Appl. No. 62/454,500, filed Feb. 3, 2017, 43 pages.
Doebler et al., "Continuous-Flow, Rapid Lysis Devices for Biodefense Nucleic Acid Diagnostic Systems" *Journal of Laboratory Automation* 14(3):119-125, 2009.
Doebler et al., "Effect of Triton X-100 on Nicking Endonuclease Activity of N.BstNBI during Isothermal Exponential Amplification of Oligonucleotides Performed Using a Hand-held Real-time Fluorescence-based Device," Keck Graduate Institute, Poster, 2005, 1 page.
Doebler et al., "System, Apparatus and Method for Lysing," U.S. Appl. No. 61/020,072, filed Jan. 9, 2008, 62 pages.
European Decision to Grant a Patent, dated Sep. 15, 2016, for European Application No. 09700618, 2 pages.
European Intention to Grant, dated Apr. 29, 2016, for European Application No. 09 700 618, 9 pages.
Extended European Search Report, dated Jul. 19, 2012, for European Application No. 09 70 0618, 9 pages.
Extended European Search Report, dated May 9, 2014, for European Application No. 10 79 2687, 8 pages.
Farmer et al., "Hand-held thermal-regulating fluorometer," *Review of Scientific Instruments* 76(11):115102, 2005. (5 pages).
Final Office Action, dated Apr. 29, 2013, for U.S. Appl. No. 12/823,081, Irvine et al., "Capture and Elution of Bio-Analytes via Beads That Are Used to Disrupt Specimens," 14 pages.
Final Office Action, dated Feb. 24, 2015, for U.S. Appl. No. 12/823,081, Irvine et al., "Capture and Elution of Bio-Analytes via Beads That Are Used to Disrupt Specimens," 11 pages.
Final Office Action, dated May 10, 2016, for U.S. Appl. No. 14/451,015, Doebler et al., "System, Apparatus and Method for Material Preparation and/or Handling," 11 pages.
Final Office Action, dated May 21, 2014, for U.S. Appl. No. 12/732,070, Doebler et al., "System, Apparatus and Method for Material Preparation and/or Handling," 8 pages.
Geciova et al., "Methods for disruption of microbial cells for potential use in the dairy industry—a review," *International Dairy Journal* 12(6):541-553, 2002.
Harrison, "Bacterial Cell Disruption: A Key Unit Operation in the Recovery of Intracellular Products," *Biotechnology Advances* 9(2):217-240, 1991.
Hopkins, "Physical and Chemical Cell Disruption for the Recovery of Intracellular Proteins," *Purification and Analysis of Recombinant Proteins*, Marcel Dekker, Inc., New York, New York, USA, 1991, pp. 57-83. (31 pages).
International Preliminary Report on Patentability, dated Jan. 4, 2012, for International Application No. PCT/US2010/039872, 5 pages.
International Preliminary Report on Patentability, dated Jul. 13, 2010, for International Application No. PCT/US2009/030622, 5 pages.
International Search Report, dated Aug. 27, 2009, for International Application No. PCT/US2009/030622, 3 pages.
International Search Report, dated Mar. 23, 2011, for International Application No. PCT/US2010/039872, 6 pages.
Irvine et al., "Capture and Elution of Bio-Analytes via Beads That Are Used to Disrupt Specimens," U.S. Appl. No. 61/220,984, filed Jun. 26, 2009, 67 pages.
Irvine et al., "Capture and Elution of Bio-Analytes via Beads That Are Used to Disrupt Specimens," U.S. Appl. No. 61/317,604, filed Mar. 25, 2010, 91 pages.
Japanese Decision to Grant a Patent, dated Feb. 3, 2015, for Japanese Application No. 2012-517746, 4 pages. (with English Translation).
Japanese Decision to Grant a Patent, dated Oct. 18, 2016, for Japanese Application No. 2015-043852, 4 pages. (with English Translation).
Japanese Final Office Action, dated Jul. 2, 2014, for Japanese Application No. 2010-542379, 6 pages. (with English Translation).
Japanese Notice of Allowance, dated Nov. 11, 2014, for Japanese Application No. 2010-542379, 3 pages.
Japanese Office Action, dated Apr. 8, 2014, for Japanese Application No. 2012-517746, 13 pages. (with English Translation).
Japanese Office Action, dated Jan. 5, 2016, for Japanese Application No. 2015-043852, 6 pages. (with English Translation).
Japanese Office Action, dated May 21, 2013, for Japanese Application No. 2010-542379, 8 pages. (with English Translation).
Kim et al., "Cell lysis on a microfluidic CD (compact disc)" *Lab on a Chip* 4(5):516-522, 2004.
Nadim et al., "System, Apparatus and Method to Separate Material," U.S. Appl. No. 61/117,012, filed Nov. 21, 2008, 41 pages.
Notice of Allowance, dated Oct. 30, 2015, for U.S. Appl. No. 12/823,081, Irvine et al., "Capture and Elution of Bio-Analytes via Beads That Are Used to Disrupt Specimens," 7 pages.
Non-final Office Action, dated Aug. 27, 2018, for U.S. Appl. No. 15/299,059, , Doebler et al., "System, Apparatus and Method for Material Preparation and/or Handling," 19 pages.
Office Action, dated Aug. 14, 2013, for U.S. Appl. No. 12/732,070, Doebler et al., "System, Apparatus and Method for Material Preparation and/or Handling," 10 pages.
Office Action, dated Aug. 31, 2012, for U.S. Appl. No. 12/823,081, Irvine et al., "Capture and Elution of Bio-Analytes via Beads That Are Used to Disrupt Specimens," 12 pages.
Office Action, dated Dec. 2, 2015, for U.S. Appl. No. 14/451,015, Doebler et al., "System, Apparatus and Method for Material Preparation and/or Handling," 10 pages.
Office Action, dated Jul. 14, 2014, for U.S. Appl. No. 12/823,081, Irvine et al., "Capture and Elution of Bio-Analytes via Beads That Are Used to Disrupt Specimens," 9 pages.
Paul et al., "A Multichannel Handheld Sensor for Microbial Contaminants," CICEET Progress Report for the period Mar. 16, 2006 through Sep. 15, 2006, URL=http://ciceet/unh.edu/progressreports/2006/9_2009/paul05/, download date Nov. 1, 2011, 3 pages.
Porter et al., "Rapid and Efficient Recovery of Histidine-tagged Proteins Directly from Bacterial Cultures," *The FASEB Journal* 20(4):A530-A531, 2006. (3 pages).

(56) References Cited

OTHER PUBLICATIONS

Pre-Appeal Brief Request For Review Remarks, filed Sep. 23, 2016, for U.S. Appl. No. 14/451,015, Doebler et al., "System, Apparatus and Method for Material Preparation and/or Handling," 6 pages.

Preliminary Amendment, filed Aug. 5, 2014, for U.S. Appl. No. 14/451,015, Doebler et al., "System, Apparatus and Method for Material Preparation and/or Handling," 5 pages.

Preliminary Amendment, filed Jan. 13, 2016, for U.S. Appl. No. 14/993,953, Irvine et al., "Capture and Elution of Bio-Analytes via Beads That Are Used to Disrupt Specimens," 8 pages.

Preliminary Amendment, filed Mar. 29, 2010, for U.S. Appl. No. 12/732,070, Doebler et al., "System, Apparatus and Method for Material Preparation and/or Handling," 3 pages.

Response Under 37 CFR 1.116, filed Aug. 9, 2016, for U.S. Appl. No. 14/451,015, Doebler et al., "System, Apparatus and Method for Material Preparation and/or Handling," 8 pages.

Response Under 37 CFR 1.116, filed Jul. 21, 2014, for U.S. Appl. No. 12/732,070, Doebler et al., "System, Apparatus and Method for Material Preparation and/or Handling," 9 pages.

Retsch, "Mixer Mills: MM 200, MM 301," Brochure, 2002, 4 pages.

Seetharam (Ed.) et al., *Purification and Analysis of Recombinant Proteins*, CRC Press, Marcel Dekker, Inc., New York, NY, 1991, Chapter 3, pp. 57-83, Hopkins, "Physical and Chemical Cell Disruption for the Recovery of Intracellular Proteins," 31 pages.

US Digital Designs, "DNA Amplifier," URL=http://www.usdd.com/Display_Page.php?pageTitle=DNA%20Amplifier, download date Nov. 1, 2011, 1 page.

Written Opinion, dated Aug. 27, 2009, for International Application No. PCT/US2009/030622, 4 pages.

Written Opinion, dated Mar. 23, 2011, for International Application No. PCT/US2010/039872, 4 pages.

\* cited by examiner

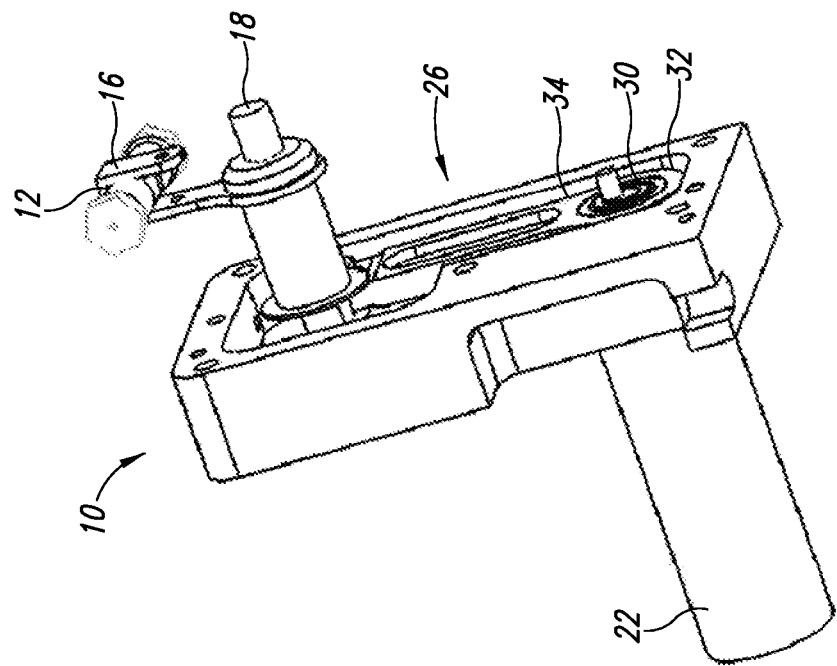
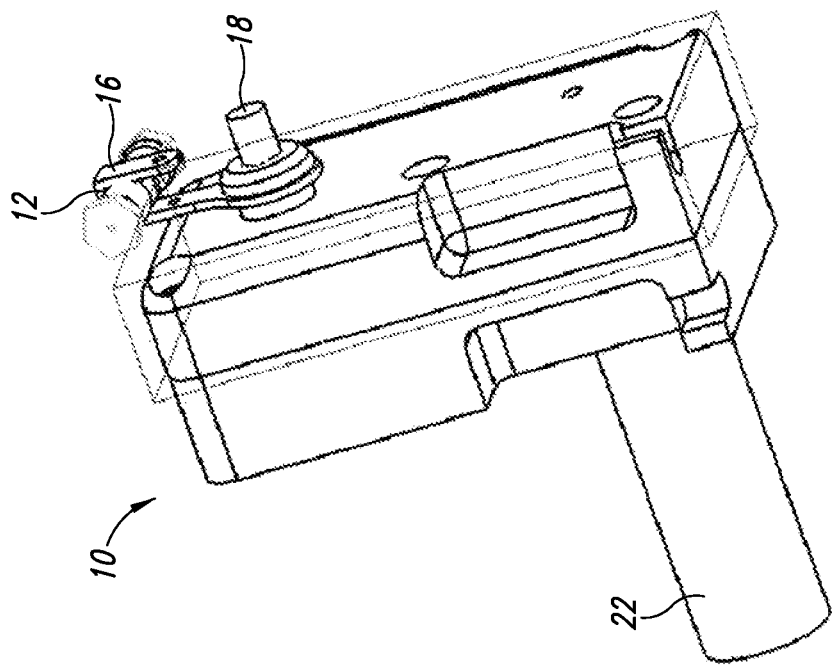

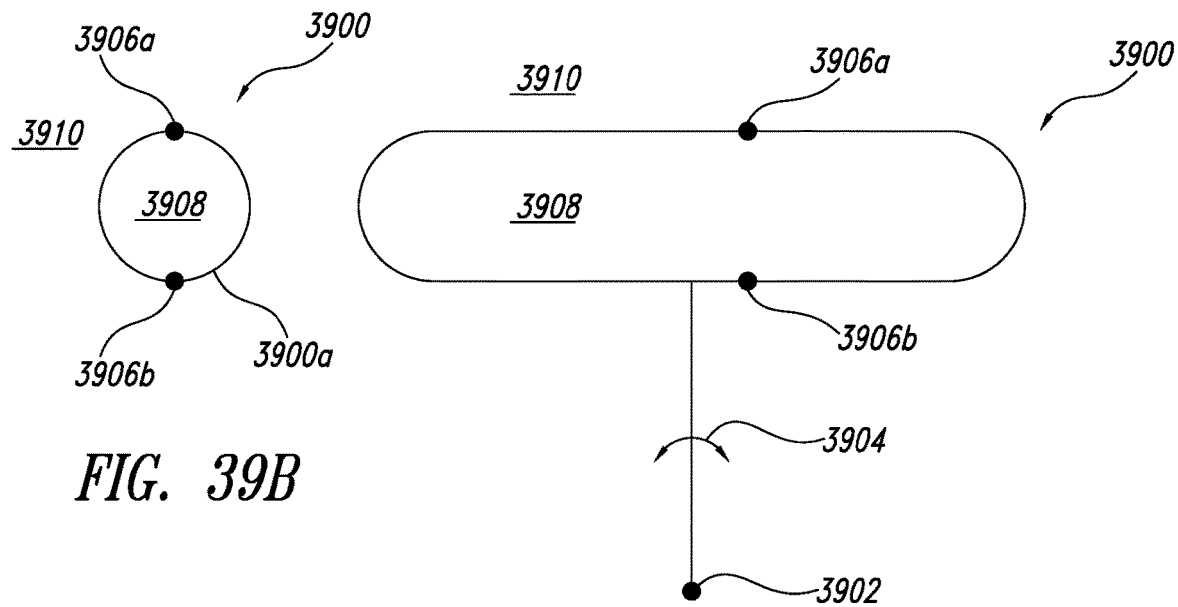
FIG. 39B
FIG. 39A
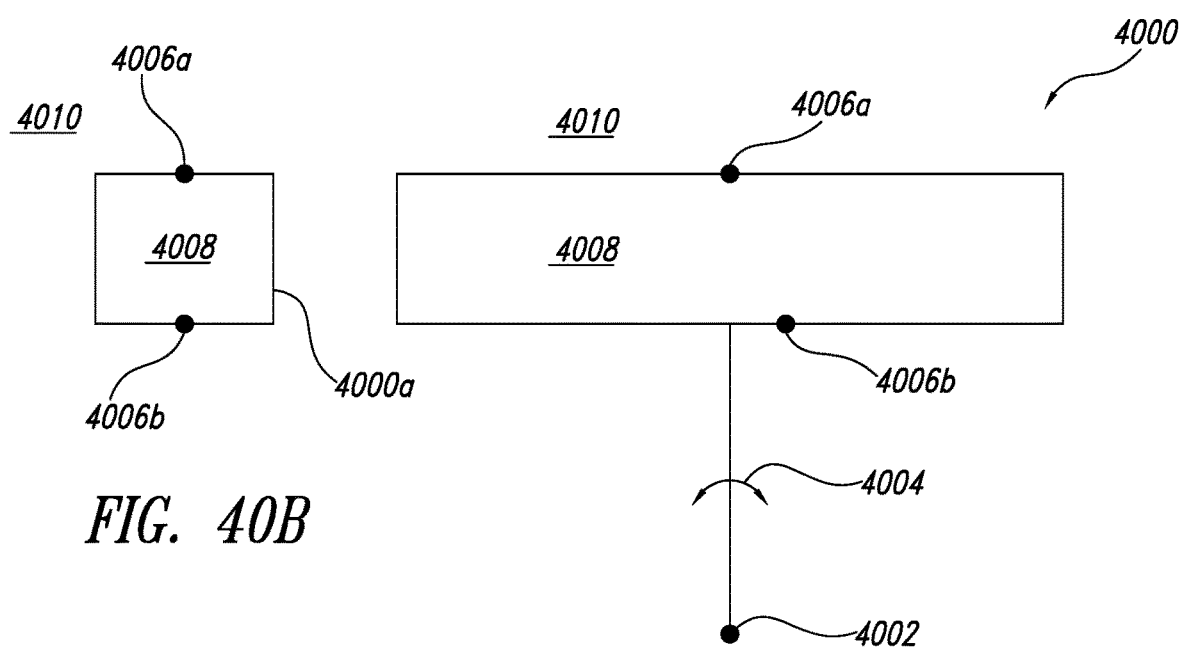
FIG. 40B
FIG. 40A

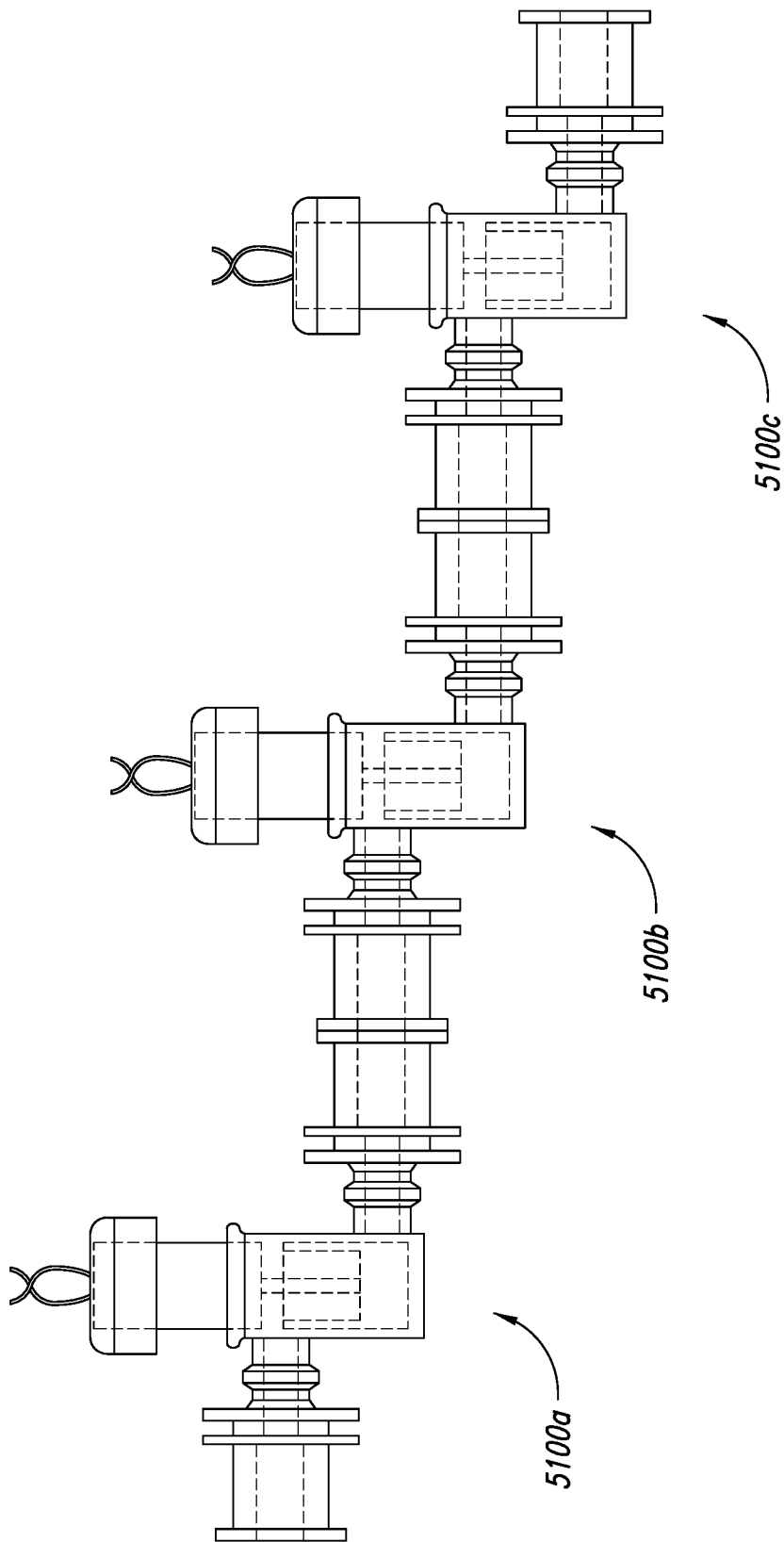

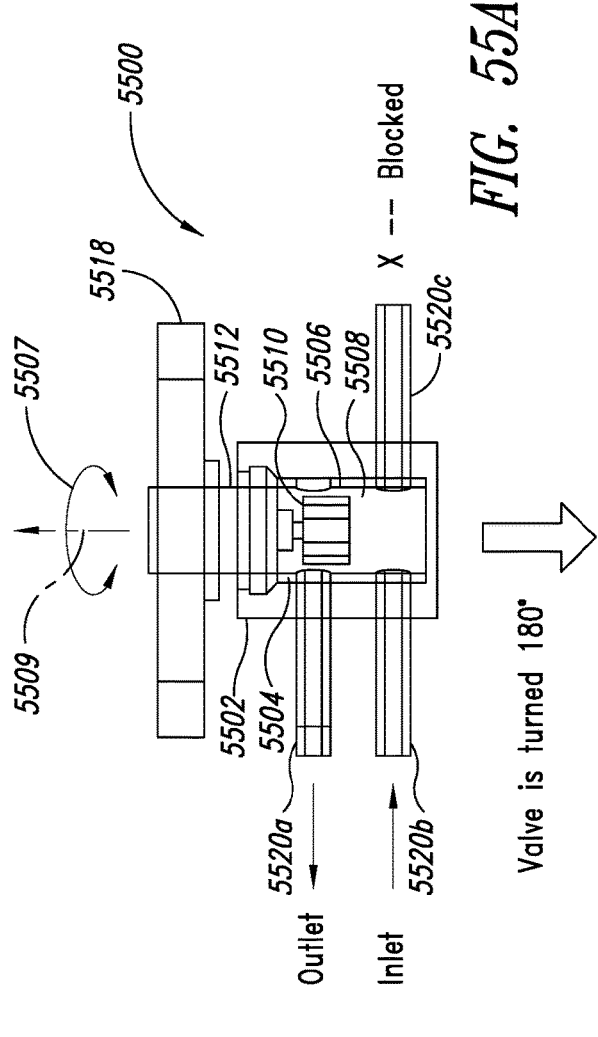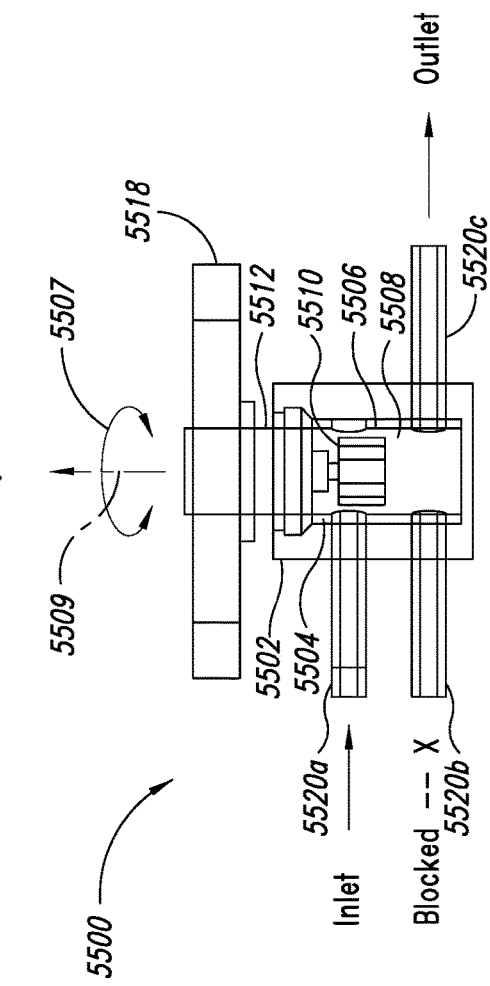
FIG. 55A
FIG. 55B

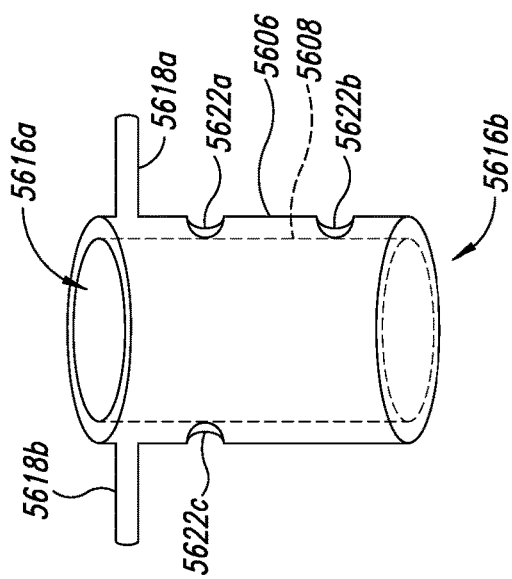
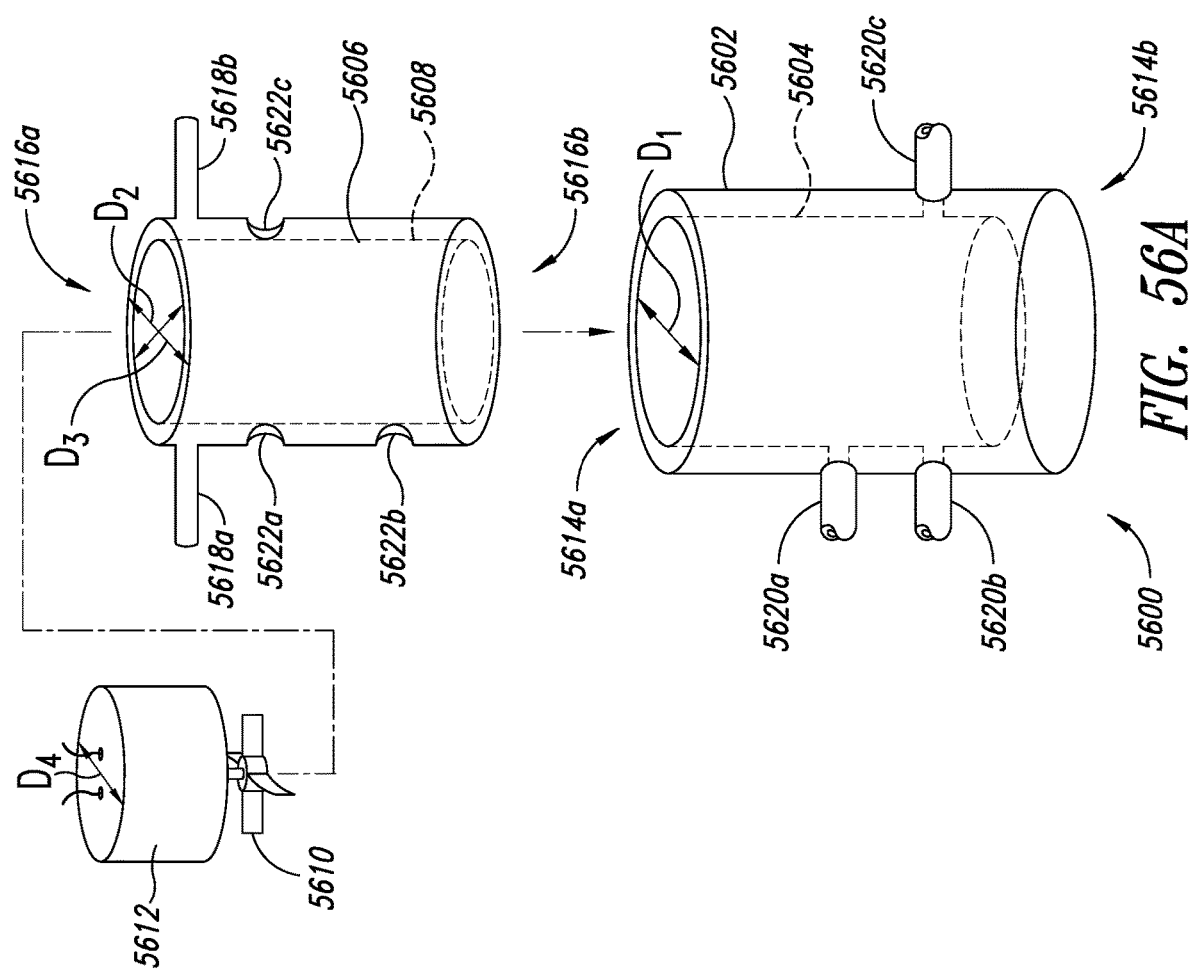
FIG. 56C
FIG. 56A

SYSTEM, APPARATUS AND METHOD FOR MATERIAL PREPARATION AND/OR HANDLING

TECHNICAL FIELD

The present disclosure relates to the separation of matter, for example particles or other material in a suspension. The present disclosure also relates to lysing and in particular to systems, apparatus and methods to perform lysing of a material to be lysed using a lysing particulate material.

BACKGROUND

There are numerous applications that require the separation of material, for example particulate or other matter in suspension. One common approach is to employ a centrifuge to separate relatively heavier material from relatively light material. Centrifuges typical include a container to hold the material, a drive system including a motor and transmission or linkage coupled to rotate the container about a fixed axis of rotation. The material in the container separates based on density under centripetal acceleration, with denser or heavier material tending to collect at a perimeter relatively away from the axis of rotation and with the less dense or lighter material tending to collect relatively closer to the axis of rotation.

Centrifuges may be used on a large variety of material from particulates, to fluids, to gases, and combinations of the same. Centrifuges are often used to separate biological material, for example in preparing samples for analysis of the composition of specific biological materials, such as proteins, lipids, and nucleic acids either individually or as complexes. A centrifuge may be used to isolate certain organelles-nuclei, mitochondria, lysosomes, chloroplasts, and/or endoplasmic reticulum.

Lysis of biological material, for example cell lysis, is used to analyze the composition of specific biological materials, for example proteins, lipids, and nucleic acids either individually or as complexes. If a cell membrane is lysed then certain organelles-nuclei, mitochondria, lysosmes, chloroplasts, and/or endoplasmic reticulum may be isolated. Such may be analyzed using PCR, electron microscopy, Western blotting or other analysis techniques.

There are numerous approaches to performing lysis. For example, enzymatic approaches may be employed to remove cell walls using appropriate enzymes, in preparation to cell disruption or to prepare protoplasts. Another approach employs detergents to physically disrupt cell membranes. These chemical approaches may adversely affect the resulting product, for example degrading the bio-products being released. Consequently, chemical approaches may, in some instances, not be practical.

Yet another approach employs ultrasound to produce cavitation and impaction for disrupting the cells. Such an approach may not achieve as high a lysis efficiency as may be required or desired for many applications.

Yet still another approach employs beads (e.g., glass or ceramic) which are agitated, for example, via a vortex mixer. Such an approach successfully addresses the issues raised by chemical lysis approaches, yet improvements in such an approach are desirable.

BRIEF SUMMARY

There is a need for other approaches to separating materials. Such approaches may provide quicker separation, more thorough separation, or may separate materials in a different manner than previous approaches.

There is also a need for bead-based lysing apparatus and methods that are more efficient than current lysing apparatus. Such may reduce the amount of time required to process a sample (i.e., material to be lysed) and/or increase throughput. Such may also increase the level or thoroughness of lysing, producing greater amounts of lysed material from a given sample size. There is also a need for lysing apparatus and methods that operate on sample sizes that are relatively small (e.g., 10 micro-liters) compared to conventional lysing apparatus. Such may enable lysing to be performed where a relatively small amount of a sample is available and/or reduce costs. Such may also reduce the amount of lysing particulate material that is required, also providing cost reductions. Such may also allow higher frequency oscillation, thereby increasing efficiency, while maintaining reasonable lifetime or fatigue characteristics. There is also a need to efficiently and reliably lyse typically difficult to lyse material, for example spores. There is a further need for the ability to perform flow-through lysing. Such may allow large quantities of small samples to be processed over time, for example processing small samples taken every minute over a long period of time (e.g., day, week, month, and/or years). There is also a need for lysing equipment that is small and hence portable, and that is relatively inexpensive yet sufficiently robust to withstand travel or harsh operating environments.

A system to perform lysis on material to be lysed may be summarized as including an arm having an attachment location to at least temporarily attach a container that at least temporarily holds a material to be lysed and a particulate lysing material; a motor operable to provide a drive force; and a drive mechanism coupled to transfer the drive force of the motor into oscillation of the attachment location of the arm along an arcuate path. The arm may be a rigid arm that does not flex under a load in response to the oscillation of the attachment location of the arm along the arcuate path. The arm may be a flexible arm that flexes under a load in response to the oscillation of the attachment location of the arm along the arcuate path.

The system to perform lysis may further include a holder at the attachment location, the holder configured to removably hold the container. The system may include the container and the particulate lysing material. In some embodiments the container is non-removably fixed to the arm at least proximate the attachment location. The container may have a first opening and at least a second opening spaced from the first opening, the first and the second openings to provide fluid communication into the chamber from an exterior thereof. The container may include a first filter positioned in the chamber and a second filter positioned in the chamber spaced from the first filter to form a particulate retainment area therebetween, the particulate retainment area positioned between the first and the second openings, the first and the second filters each having a plurality of apertures sized to substantially pass the material to be lysed and to block the particulate material. The first filter, the second filter and the particulate material may form a cartridge that is selectively replaceable in the chamber. The plurality of beads may include at least one of ceramic beads, glass beads, zirconium beads, metal beads, plastic beads, and sand and wherein the plurality of beads have diameters in the range of approximately 10 microns to approximately 600 microns. When in use a volume of the particulate matter may be greater than a volume of material to be lysed. When in use there may essentially be no air in the chamber.

The system may further include a pump operable to pump the material to be lysed through the chamber. The pump may be configured to intermittently pump the material to be lysed through the chamber. The material to be lysed may have a residence time in the chamber that may be sufficient to achieve a defined level of lysing. The pump may continuously pump the material to be lysed through the chamber. Given a length of the chamber, a flow rate of the pump may be such that the material to be lysed spends sufficient time (i.e., desired or defined residence time) in traversing the chamber from the first opening to the second opening to achieve a defined level of lysing.

The system may further include a first tube coupled to provide fluid communication to the first opening for the material to be lysed to the first opening; and a second tube coupled to provide fluid communication from the second opening for a material that has been lysed. Ends of at least one of the first and the second tubes may be reinforced. Ends of at least one of the first and the second tubes may be reinforced with additional tubes that are concentric about the ends of the tube. A length of at least one of the first and the second tubes may be such that the length does not restrict the oscillation of the attachment location. The length of at least one of the first and the second tubes may be such that the at least one of the first and the second tubes does not resonate in response to the oscillation of the attachment location of the arm along an arcuate path. A respective length of each of the first and the second tubes may be sufficiently long so as to not restrict the oscillation of the attachment location and are sufficiently short such that the first and the second tubes do not resonate during use.

The drive mechanism may consist of a four-bar linkage including a first bar rotationally driven by a motor, the bar connected by a hinge to a second bar that serves as a connecting rod. A third and a fourth bars both pivot about a central fixed axis with a fixed angle between them. The end of the second bar that serves as the connecting rod is connected by a hinge to the third bar whose length determines the angle of rotation of the third and the fourth bars. The length of the fourth bar is the radius of curvature of the arcuate motion of the lysis chamber, which is coupled or connected to the fourth bar.

A method of lysing a material to be lysed may be summarized as including receiving a material to be lysed in a chamber that contains a particulate lysing material; oscillating the chamber containing the material to be lysed and a particulate lysing material along an arcuate path to produce a lysed material; and removing the lysed material from the chamber.

The method of lysing a material to be lysed may further include pumping the material to be lysed into the chamber.

The method may further include intermittently pumping the material to be lysed into the chamber while oscillating the chamber. Intermittently pumping the material to be lysed into the chamber while oscillating the chamber may include intermittently pumping the material to be lysed into the chamber such that the material to be lysed spends sufficient time in the chamber to achieve a desired level of lysing. Intermittently pumping the material to be lysed into the chamber while oscillating the chamber may include intermittently pumping the material to be lysed into the chamber such that the chamber is completely evacuated of the lysed material during each cycle of the intermittent pumping. The chamber may be completely evacuated of the lysed material during each cycle of the intermittent pumping by the pumping into the chamber of more material to be lysed.

The method may further include continuously pumping the material to be lysed into the chamber while oscillating the chamber. The method may further include adjusting a flow rate of the pumping of the material to be lysed into the chamber based on a length of the chamber, a flow rate of the pump is such that the material to be lysed spends sufficient time in the chamber (i.e., residence time) to achieve a desired level of lysing.

The method may further include directing the lysed material removed from the chamber to at least one analysis device. The method may further include evacuating the chamber with an inert fluid.

A method of lysing a material to be lysed may be summarized as including receiving a first cartridge having a chamber that contains a particulate lysing material and a material to be lysed; and oscillating the first cartridge having the chamber that contains the material to be lysed and the particulate lysing material along an arcuate path to produce a lysed material.

The method may further include receiving a second cartridge in place of the first cartridge, the second cartridge having a chamber that contains a particulate lysing material and a material to be lysed; and oscillating the second cartridge having the chamber that contains the material to be lysed and the particulate lysing material along an arcuate path to produce a lysed material. Receiving a first cartridge may include receiving the first cartridge in a mounting bracket at an attachment point of an arm. Oscillating the first cartridge may include oscillating a rigid arm on which the first cartridge is mounted. Oscillating the first cartridge may include oscillating a flexible arm on which the first cartridge is mounted.

An article to perform flow-through lysis on material to be lysed may be summarized as including at least one wall forming at least one chamber having a first opening and at least a second opening spaced from the first opening, the first and the second openings to provide fluid communication into the chamber from an exterior thereof; a particulate lysing material received in the chamber, the particulate material including a plurality of particles sized to lyse a material to be lysed; a first filter received in the chamber between the first opening and the particulate material, the first filter having a plurality of apertures sized to substantially pass the material to be lysed and to retain the particulate material; and a second filter received in the chamber between the second opening and the particulate material, the second filter having a plurality of apertures sized to pass the material to be lysed and to retain the particulate material, wherein the first filter and the second filter form a particulate retainment area therebetween.

The article may further include an attachment structure proximate the first opening. The article may further include a first attachment structure to attach a first tube to the first opening; and a second attachment structure to attach a second tube to the second opening.

The article may further include a first nipple to attach a first tube about the first opening; and a second nipple to attach a second tube about the second opening. The at least one wall may be elongated and have a first end and a second end opposed to the first end. The first opening may be at the first end and the second opening may be at the second end. At least one wall may be cylindrically tubular.

The particulate material may be a plurality of beads. The plurality of beads may include at least one of ceramic beads, glass beads, zirconium beads, metal beads, plastic beads, and sand. The plurality of beads may have diameters in the range of approximately 100 microns. The plurality of beads may have diameters in the range of 50 microns to 150 microns. When in use, a volume of the particulate matter may be greater than a volume of material to be lysed. When in use there may be essentially no air in the chamber. The chamber may have a volume that holds less than 60 µl of the material to be lysed. The chamber may have a volume that holds approximately 10 µl to approximately 40 µl of the material to be lysed. The first and the second filters may be fixed to the wall.

A system to perform lysis may be summarized as including a container having at least one chamber to hold a material to be lysed and a lysing particulate material, the chamber having a first opening and at least a second opening to provide fluid communication into the chamber from an exterior thereof; an impeller having a number of blades received in the chamber of the container; and a micromotor coupled to turn the impeller. The first opening may provide an entrance for material to be lysed and the second opening may provide an exit for material that has been lysed.

The chamber may have a third opening, at least a portion of the micromotor may be received by the third opening and may seal the third opening. The micromotor may be removably received in the first third opening. The micromotor may be disposable.

The container may further include at least a first filter positioned before the exit in a flow path, the first filter having a plurality of apertures sized to substantially pass material that has been lysed and to substantially block lysing material. The container may further include at least a second filter positioned following the entrance in the flow path, the second filter having a plurality of apertures sized to substantially pass material to be lysed and to substantially block lysing material.

The micromotor may pulsate. The micromotor may drive the impeller at a rate of greater than 10,000 RPM in the presence of liquid and beads. The micromotor may drive the impeller at a rate of approximately 50,000 RPM, when not in the presence of liquid and beads.

A method of system to perform lysis, may be summarized as including receiving a material to be lysed via an entrance in at least one chamber of a container that holds a lysing particulate material; driving an impeller having a number of blades received in the chamber of the container via a micromotor; and expelling a material that has been lysed via an exit from the chamber of the container.

Expelling a material that has been lysed via an exit may include expelling the material that has been lysed via a first filter positioned before the exit in a flow path, the first filter having a plurality of apertures sized to substantially pass the material that has been lysed and to substantially block the lysing particulate material. Receiving a material to be lysed via an entrance may include receiving the material to be lysed via a second filter positioned following the entrance in the flow path, the second filter having a plurality of apertures sized to substantially pass the material to be lysed and to substantially block lysing particulate material.

The method of system to perform lysis may further include intermittently pumping the material to be lysed into the at least one chamber via the entrance. The method may further include continuously pumping the material to be lysed into the at least one chamber via the entrance.

Driving an impeller may include pulsating the impeller. Driving an impeller may include driving the impeller at a rate of greater than 10,000 RPM in the presence of liquid and beads. The method may further include replacing the micromotor with a new micromotor. The method may further include disposing the micromotor.

A system to perform lysis, may be summarized as including a first container having at least one chamber to hold a material to be lysed and a lysing particulate material, the chamber having a single opening to provide fluid communication into the chamber from an exterior thereof; an impeller having a number of blades received in the chamber of the first container; and a micromotor coupled to turn the impeller, at least a portion of the micromotor removably received in the single opening of the first container to seal the single opening in use. The micromotor may be disposable. The micromotor may be removably received by a single opening of a second container after removal from the single opening of the first container. The micromotor may pulsate. The micromotor may drive the impeller at a rate of greater than 10,000 RPM in the presence of liquid and beads.

A method of operating a system to perform lysis may be summarized as including receiving a material to be lysed via an entrance in at least one chamber of a first container that holds a lysing particulate material; locating an impeller in the chamber of the first container via the entrance; closing the entrance of the first container with a micromotor that is coupled to drive the impeller; and driving the impeller to circulate the material to be lysed and the lysing particulate material in the chamber of the first container.

The method of system to perform lysis may further include removing the micromotor from the entrance of the first container and removing a material that has been lysed via the entrance of the first container. Removing a material that has been lysed via the entrance of the first container may include withdrawing the material that has been lysed using a pipette. Driving the impeller may include pulsating the impeller. The method may further include reusing the micromotor with a second container. The method may further include disposing of the micromotor.

A system to separate materials may be summarized as including: a base; an actuator coupled to the base and selectively operable to provide a drive force; and a drive mechanism coupled to the base and coupled to transfer the drive force of the motor into a high frequency oscillatory angular rotation of a container about an axis of rotation. The actuator may be an electric motor.

The system may further include a holder coupled to the drive mechanism for movement thereby, the holder configured to removably hold the container.

The system may further include the container, wherein the container has an interior to hold the materials to be separated.

The system may further include the container, wherein the container has an interior to hold the materials to be separated and the container is non-removably fixed to the drive mechanism.

The system may further include the container, wherein the container has an interior to hold the materials to be separated and at least one inner port to provide fluid communication between the interior of the container and an exterior thereof, the at least one inner port positioned relatively proximate the axis of rotation with respect to an arc defined by an oscillatory movement of an outer most portion of the container from the axis of rotation.

The system may further include the container, wherein the container has an interior to hold the materials to be separated and at least one inner port to provide fluid communication between the interior of the container and an exterior thereof, the at least one inner port positioned at an inner periphery of the container.

The system may further include the container, wherein the container has an interior to hold the materials to be separated and at least one outer port to provide fluid communication between the interior of the container and an exterior thereof, the at least one outer port positioned relatively distal from the axis of rotation.

The system may further include the container, wherein the container has an interior to hold the materials to be separated and at least one outer port to provide fluid communication between the interior of the container and an exterior thereof, the at least one outer port positioned at an outer periphery of the container.

The system may further include the container, wherein the container has an interior to hold the materials to be separated, at least one inner port to provide fluid communication between the interior of the container and an exterior thereof and at least one outer port to provide fluid communication between the interior of the container and the exterior thereof, the at least one inner port spaced relatively closer to the axis of rotation with respect to the at least one outer port. The container may include at least one filter proximate one of the inner or the outer ports. The at least one filter may be selectively replaceable in the container.

The system may further include a pump to pump the material to be separated through the container. The pump may be configured to intermittently pump the material through the container. The axis of rotation may pass through the container. The container may be spaced from the axis of rotation. The drive mechanism may include a four-bar linkage that may include a first member, a second member, a third member and a fourth member, the second member coupled to the first member, the first member rotationally driven by a motor to eccentrically drive a first end of the second member in a circular motion, the third bar member pivotally coupled to a second end of the second member, the third member connected to the fourth member at a pivot point; where an amplitude of motion of the second member and a length of the third member define a angle of motion of the third and the fourth members and a length of the fourth member defines a distance of arcuate motion. The system may include a controller coupled to control a frequency of the oscillatory angular rotation of the container and selectively operable to set the frequency to a sufficiently low frequency as to cause the relatively denser material to collect relatively farther from the axis of rotation than the relatively less dense material.

A method to separate materials may be summarized as including: receiving a material to be separated in a container; oscillating angularly rotating the container at a high frequency; and removing at least some of the separated material from the container.

The method may further include pumping the material to be separated into the container. The method may further include intermittently pumping the material to be separated into the container while oscillating the container. The method may further include directing at least some of the separated material removed from the container to at least one analysis device. The method may further include evacuating the container with an inert fluid. The method may further include varying a speed of the oscillating angular rotating to change a direction in which particles in the material move during separation.

Such apparatus and methods may produce unexpected results. For example, in contrast to standard centrifuges, such apparatus and methods may cause denser or heavier materials to collected relatively close to an axis of rotation while less dense or lighter materials collect relatively away from the axis of rotation. Additionally or alternatively, such apparatus and method may allow a direction (inward or outward with respect to the axis of rotation) of material accumulation to be selected by varying a speed of the apparatus. Such apparatus and methods may even be used to combine separate materials.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 1C is a front, left side, bottom isometric view of the apparatus of FIG. 1A.

FIG. 2C is a front, right side, bottom isometric view of the apparatus of FIG. 2A.

FIG. 39A is a top plan view of a container to hold material to be separated, according to another illustrated embodiment.

FIG. 39B is a side-elevational view of the container of FIG. 10A.

FIG. 40A is a top plan view of a container to hold material to be separated, according to another illustrated embodiment.

FIG. 40B is a side-elevational view of the container of FIG. 11A.

FIG. 52 is a plan view of a plurality of lysing apparatus coupled sequentially to one another, according to one illustrated embodiment.

FIG. 55A is a side elevational view of a stopcock style lysing device, according to one illustrated embodiment, showing an inner portion rotated or configured to provide a first flow path via two selected ports.

FIG. 55B is a side elevational view of the stopcock style lysing device of FIG. 55A, showing the inner portion rotated or configured to provide a second flow path via two selected ports.

FIG. 56A is an exploded isometric view of a stopcock style lysing device, according to one illustrated embodiment, showing an inner vessel having an open bottom portion, the inner vessel in a first orientation with respect to an outer vessel.

FIG. 56C is an isometric view of the inner vessel of FIG. 56A, showing the inner vessel in a second orientation, different from the orientation illustrated in FIG. 56A.

DETAILED DESCRIPTION

Figure 2A:
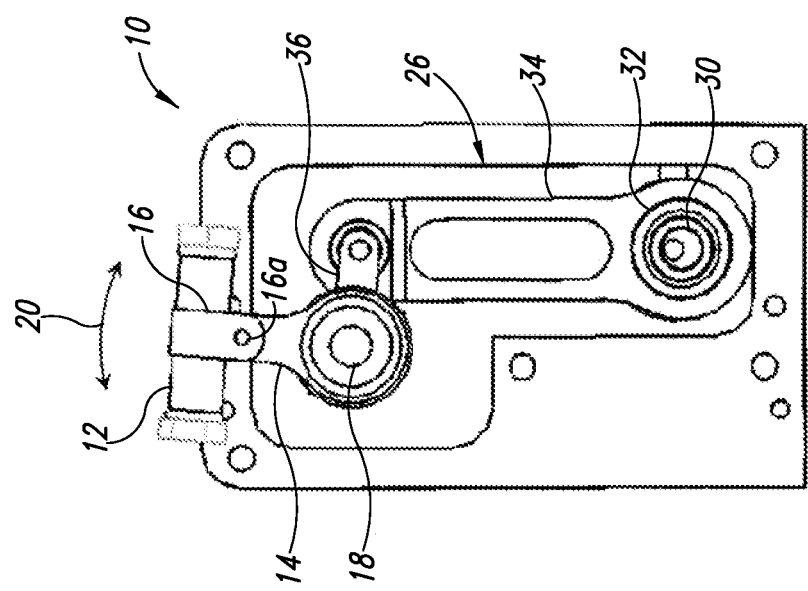
FIG. 2A is a front elevational view of the apparatus of FIG. 1A with a front cover removed, according to one illustrated embodiment.
Figure 1A:
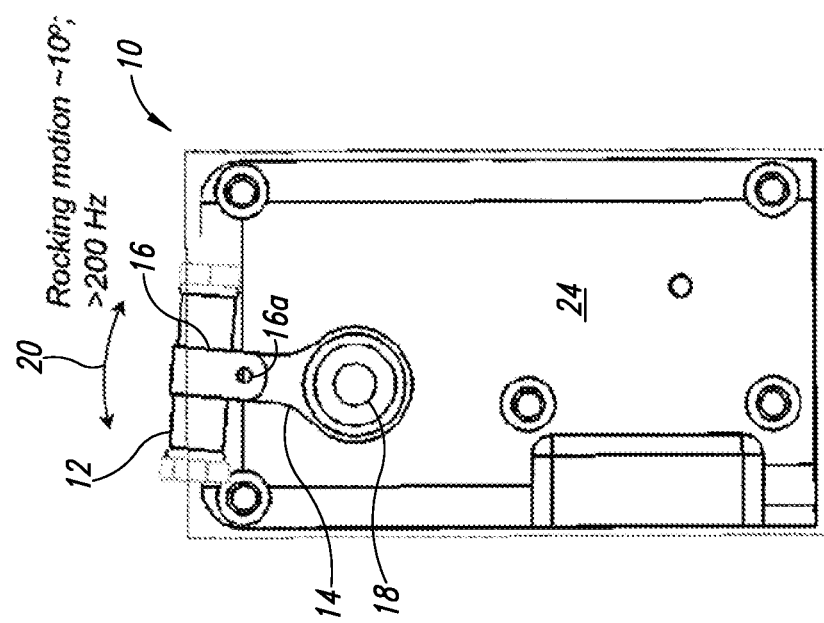
FIG. 1A is a front elevational view of an apparatus to perform material separation and/or lysis, according to one illustrated embodiment.
Figure 2B:
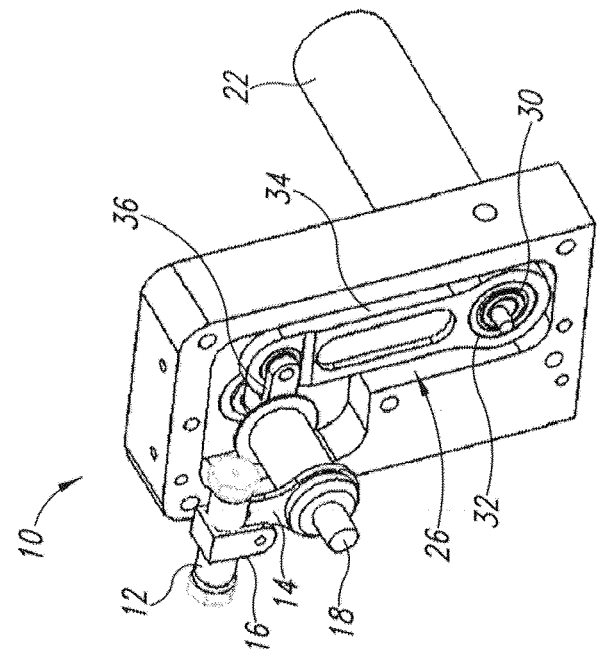
FIG. 2B is a front, right side, top isometric view of the apparatus of FIG. 2A.
Figure 3:
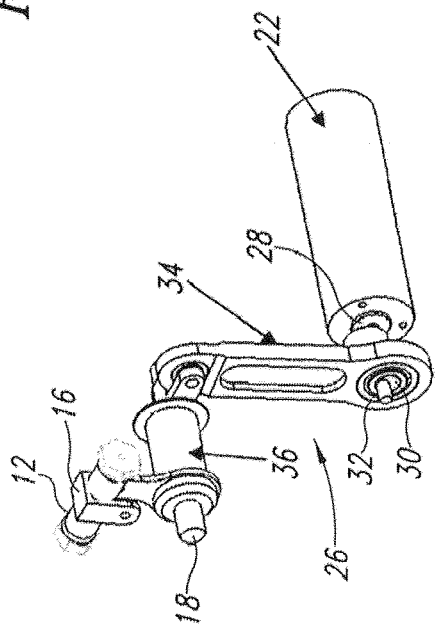
FIG. 3 is a front, right side isometric view of a motor and drive mechanism of the apparatus of FIGS. 1A-2C.
Figure 1B:
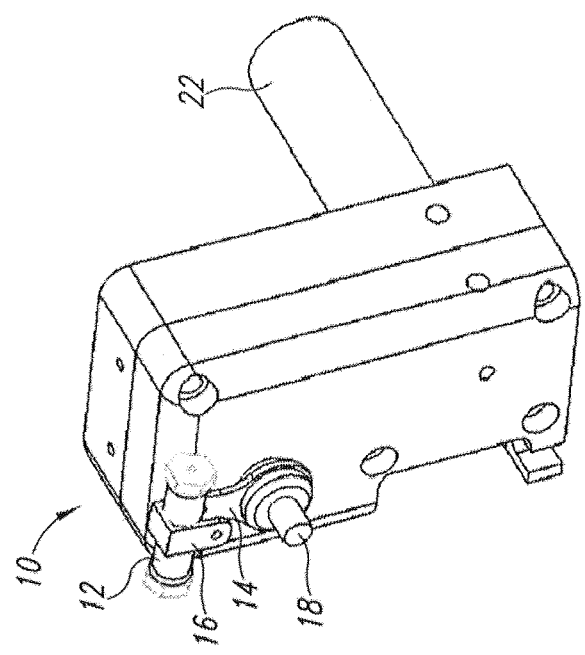
FIG. 1B is a front, right side, top isometric view of the apparatus of FIG. 1A.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with micromotors, controllers including motor controllers, and control systems such as programmed general purpose computing systems and the like have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

A number of embodiments of apparatus and systems to separate materials are described herein. The material separation apparatus and systems perform separation on a material to be separated, for example a particulate material in suspension, to produce separated material or material that has been separated. The material to be separated may take the form of biological materials, for example cells, spores, tissue, yeast, fungi, plants, bacteria, etc., typically suspended in a liquid medium. For instance the material may take the forms of organelles-nuclei, mitochondria, lysosomes, chloroplasts, endoplasmic reticulum, etc. The material may include lysing particulate material, for instance beads.

A number of embodiments of lysis apparatus and systems are described herein. The lysis apparatus and systems perform lysis on a material to be lysed using lysing particulate material, to produce lysed material or material that has been lysed. The material to be lysed may take the form of biological materials, for example cells, spores, tissue, yeast, fungi, plants, bacteria, etc., typically suspended in a liquid medium. The lysing particulate material may take a variety of forms. While generally referred to herein as beads, the term bead is not meant to be limiting with respect to size or shape. The beads may, for example, take the form of ceramic beads, glass beads, zirconium beads, zirconium/silica beads, metal beads, plastic beads, and/or sand. The lysed material may likewise take a variety of forms, for example organelles-nuclei, mitochondria, lysosomes, chloroplasts, endoplasmic reticulum, etc.

Various embodiments of the material separation and/or lysis apparatus and systems may, for example, operate in: 1) a batch mode, 2) flow-through stop or semi-batch mode, or 3) continuous flow-through mode. In batch mode, a container having a chamber holding a sample of material to be separated or lysed is located in a holder and oscillated. The container is removed after sufficient oscillation and the separated and/or lysed material recovered. In the flow-through stop or semi-batch mode, a sample of material to be separated or lysed flows into to fill the chamber. The container is then oscillated until sufficiently separated and/or lysed. The chamber is evacuated of the separated and/or lysed material. In the flow-through mode, a sample of material to be separated and/or lysed flows through the chamber of the container during oscillation at a desired flow rate, providing a desired or defined residence time within the chamber. In the flow-through stop or semi-batch mode, the sample may abutted by an immiscible liquid or gas and the chamber may be evacuated by a blast of a fluid, for example a liquid or a gas.

At least some of the embodiments take advantage of the understanding that the forces responsible for mechanical rupture of biological samples scale with the oscillation frequency squared, and that by employing relatively small sample sizes, the various embodiments described herein can achieve relatively higher frequencies than commercially available apparatus, resulting in rapid and efficient lysis. Various specific embodiments will now be discussed.

At least some of the embodiments take advantage of a recently identified property of material to undergo an "anti-centrifugal" force when oscillated at a sufficiently high frequency, which frequency is a function of various characteristics of the particles. Such may be advantageously employed to change a direction of motion of particles or to achieve a direction of separation not previously thought to be achievable. Such may be employed with a variety of materials and is not limited or restricted to lysing.

Figure 4:
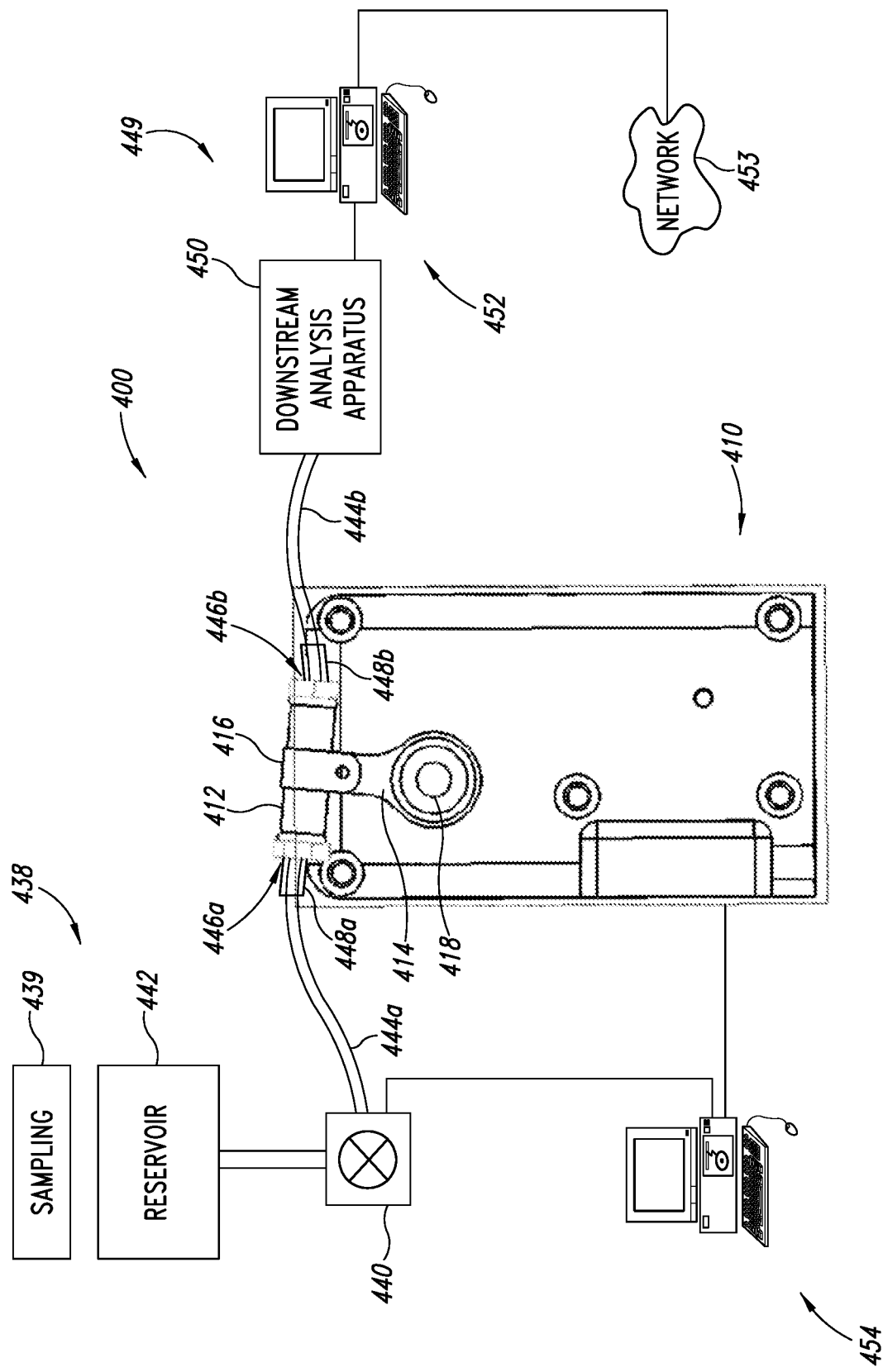
FIG. 4 is a schematic view of a system to perform flow-through processing, including an apparatus to perform material separation and/or lysis, an upstream subsystem to provide material to be separated and/or lysed, a downstream subsystem to analyze material that has been separated and/or lysed, and a control subsystem, according to one illustrated embodiment.

FIGS. 1A-1C and 2A-2C show an apparatus 10 operable to perform separation and/or lysing on a material to be separated and/or lysed contained in a container 12, according to one illustrated embodiment. In some embodiments, off-the-shelf vials and tubes may be employed as the container 12 to hold specimens of material to be separated and/or lysed and the lysing particulate material or other material, for example PCR or Eppendorf tubes. While illustrated in FIGS. 1A-1C and 2A-2C in a batch mode, the separation and/or lysis apparatus 10 may be used in a flow-through stop or semi-batch mode or in a continuous mode as illustrated in FIG. 4.

The container 12 may be removably coupled to an arm 14 via a holder 16. The holder 16 may take a variety of forms. For example, the holder 16 may take the form of a U-shaped clamp or other member. The holder 16 may include a fastener (e.g., screw, bolt, etc.) 16a operable to secure the holder 16 in a container securing configuration. Alternatively, the holder 16 may be resilient and biased into the container securing configuration.

The arm 14 may be coupled to pivot about an axle 18 such that the container 12 oscillates along an arcuate path 20. Oscillation along an arcuate path 20 achieves confined periodic flow fields with angular accelerations that provide strong particulate flow fields and large shear rates between beads in a liquid solution or slurry. Experiments by the applicants have demonstrated that miniaturized geometries can provide superior lysis through the application of high frequencies (e.g., greater than approximately 100 Hz). Since the relative forces on non-neutral density beads in a liquid scale according to $\omega^2 r$, where w represents angular velocity and r is the distance of a bead from the center of rotation, a small increase in angular speed can allow for a substantial decrease in size to attain similar performance. Linear oscillatory motions, even at high frequencies result in little lysis of biological samples, while those with an arc motion may achieve lysis that is superior to commercially available bead-based lysis apparatus. High-speed movies clearly show that linear motions result in periodic concentration of beads followed by expansion of beads away from one another, but relatively little relative motion of beads that is not along the axis of motion. In contrast, where a container oscillates in an arc, the beads are seen to compress to higher density just as a strong swirl is induced, resulting in very effective lysing. Collisions and shearing provided by the relative motion of the suspended beads contribute to the high efficiency of the lysing.

The arm 14 may be a rigid arm, i.e., an arm that does not appreciably bend during oscillation with a load having a mass at least roughly equivalent to an expected load of a container containing a material to be lysed and a lysing particulate material. Alternatively, the arm 14 may be a flexible arm, i.e., an arm that does appreciably bend during oscillation with a load having a mass at least roughly equivalent to an expected load of a container containing a material to be separated and/or lysed and optionally a lysing particulate material.

As best illustrated in FIGS. 2A-2C and 3 in which a cover plate 24 is removed, the arm 14 may be driven via a motor 22 and a drive mechanism 26, which may take the form of a four-bar linkage. In particular, a shaft 28 of the motor 22 drives a first member such as a bar, here in the form of eccentric cam 30. The eccentric cam 30 is received in a bore 32 of a second member or connecting arm 34. The connecting arm 34 is drivingly coupled to the holder 16 by the axle 18 of a rocker arm 36. The drive mechanism 26 provides a low cost, reliable mechanism to realize relatively high frequency oscillatory motion along the arcuate path 20. While such frequencies may not be considered high for other types of devices, of instance rotating devices or ultra-sonic devices, such frequencies are considered high oscillating type devices.

FIG. 4 shows a flow-through separation and/or lysis system 400 according to one illustrated embodiment. As described in more detail herein, the flow-through separation and/or lysis system 400 may be operated in a flow-through stop or semi-batch mode, or in a continuous flow mode.

The flow-through system 400 includes a separation and/or lysing apparatus 410 and a container 412, which may be similar to those described in previous embodiments. For example, the separation and/or lysing apparatus 410 may include an arm 414 and holder 416 to hold the container 412 as the container pivotally oscillates about an axle 418.

The flow-through separation and/or lysis system 400 may include an upstream subsystem 438 to deliver material to be separated and/or lysed. For example, the upstream subsystem 438 may include a pump 440 operable to pump or otherwise deliver material to be separated and/or lysed to the container 412. The upstream subsystem 438 may also include a reservoir 442 that holds the material to separated and/or lysed.

The upstream subsystem 438 may additionally or alternatively include a mechanism to collect material to be separated and/or lysed, for example a sampling apparatus 439. The sampling apparatus 439 may be manually operated or may be automatic. The sampling apparatus 439 may, for example, sample the ambient environment, for example the air or atmosphere, water or fluids, soil or other solids. The sampling apparatus 439 may include a vacuum or mechanism to create a negative pressure to extract a sample. The sampling apparatus 439 may include an actuator, for example an arm with a shovel or broom to retrieve samples. The sampling apparatus may include an actuator, for example a needle and syringe to example samples.

The material to be separated and/or lysed may be delivered via one or more conduits, for example, a tube 444a to an entrance 446a of the container 412. The tube 444a may be reinforced at one or both ends, for example, being reinforced with multiple layers of concentrically arranged tubes 448a. The tube 444a may have a length $L_1$ that is sufficiently long to allow the container 412 and arm 414 to oscillate, while being sufficiently short as to prevent resonance in the tube. The length $L_1$ would be a function of the density, the rigidity, or the attachment method of the tube 444a as well as the density, mass and/or rigidity of any material to be separated and/or lysed carried therein.

The flow-through separation and/or lysis system 400 may further include a downstream analysis subsystem 449. The downstream analysis subsystem 449 may include one or more downstream analysis apparatus 450. The downstream analysis apparatus 450 may take any of a variety of forms.

For example, the downstream analysis apparatus 450 may include a nucleic acid amplification instrument, electron-microscope, western blotting apparatus, mass spectrometer, gas chromatograph, etc.

The downstream analysis subsystem 449 may further include one or more computing systems 452 communicatively coupled to the downstream analysis apparatus 450. The computing system 452 may be coupled to one or more networks 453, for example a local area network (LAN), a wide area network (WAN) such as the Internet, and/or a wireless wide area network (VVWAN). The computer system 452 may provide information about the results of an analysis performed on separated and/or lysed material via the network 453. For example, the computing system 452 may automatically provide an alert or other message to suitable system based on the results of the analysis. Such may, for example, be used to provide an alert when a toxic or dangerous substance or condition is detected.

The downstream analysis apparatus 450 may be fluidly communicatively coupled to an exit 446*b* of the container 412 via one or more conduits, for example, tube 444*b*. The tube 444*b* may be reinforced at one or both ends, for example, by one or more concentrically arranged lengths of tube 448*b*. The tube 444*b* may have a length $L_2$ that is sufficiently long as to allow the container 412 and arm 414 to oscillate freely while being sufficiently short as to prevent resonance of the tube 444*b*. The length $L_2$ may be based on the density, the rigidity, or the attachment method of the tube 444*b* as well as a density, mass and/or rigidity of any material carried therein.

The flow-through separation and/or lysis system 400 may further include one or more control systems 454. The control system 454 may take the form of one or more motor controllers and/or computing systems. The control system 454 may be configured to operate the flow-through system 400 in a flow-through stop or semi-batch mode and/or in a flow-through continuous flow mode. The control systems 454 may, for example, be communicatively coupled to control the separation and/or lysing apparatus 410 and/or pump 440.

The flow-through system 400 provides a number of advantages over batch based apparatus. For example, some types of beads may have an affinity for certain bio-products that are released on lysis, so some of the cell contents may be "lost" due to adsorption on the bead surfaces. The flow-through design may advantageously automatically elute the adsorbed biomolecules. It also avoids difficult or additional acts that may be required in batch mode configurations to evacuate the chamber. For example, the flow-through embodiments may eliminate any possible need to blast the chamber with a fluid such as air to clear the chamber of the separated and/or lysed material.

Figure 5:
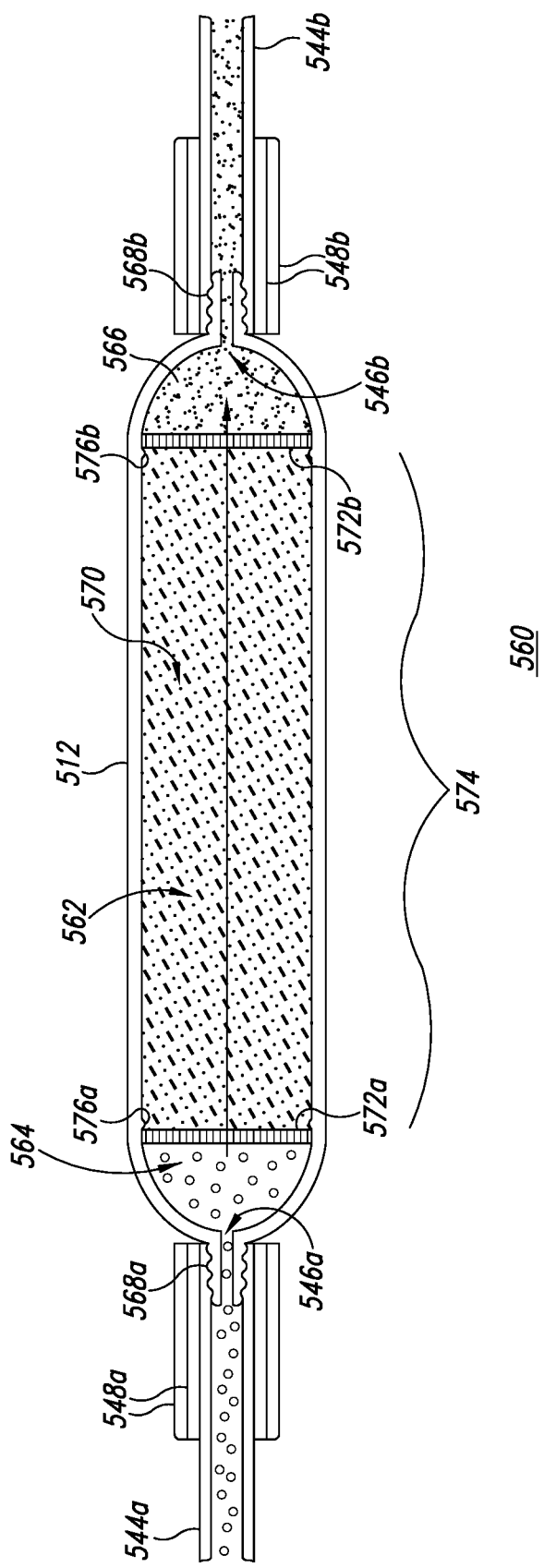
FIG. 5 is a cross-sectional view of a container having a chamber that houses material to be lysed, particulate lysing material, and material that has been lysed, according to one illustrated embodiment particularly useful in flow-through lysing.

FIG. 5 shows a container 512 according to one illustrated embodiment.

The container 512 may have an entrance 546*a* to provide fluid communication from an exterior 560 of the container to a chamber 562 of the container 512. The container 512 may include an exit 546*b* providing fluid communication between the exterior 560 and the chamber 562 of the container 512. A first tube 544*a* may be coupled to the container 512 to provide material to be lysed 564 to the chamber 562 via the entrance 546*a*. As noted previously, the tube 544*a* may be reinforced, for example, with one or more layers of concentrically arranged tubing 548*a*. A second tube 544*b* may be coupled to the container 512 via the exit 546*b* to remove lysed material 566 via the exit 546*b*. In some embodiments, the container 512 may include attachment structures to attach or otherwise couple or secure the tubes 544*a*, 544*b*. For example, the container 512 may include a ribbed nipple 568*a* at the entrance 546*a* and/or a ribbed nipple 568*b* at or proximate the exit 546*b*.

The container includes lysing material 570. The lysing material 570 may take a variety of forms, for example, a plurality of beads. The beads may take a variety of forms including one or more of ceramic beads, glass beads, zirconium beads, zirconium/silica beads, metal beads, plastic beads, and/or sand. The beads may have a variety of diameters, for example, between approximately 10 microns and approximately 600 microns.

In the flow through embodiments, the container 512 may include a first filter 572*a* positioned relatively proximate the entrance 546*a* and a second filter 572*b* positioned relatively proximate the exit 546*b*. The first and second filters 572*a*, 572*b* form a particulate retainment area 574 in which the lysing particulate material 570 is retained. In particular, the filters 572*a*, 572*b* may have a plurality of openings sized to substantially pass the material to be lysed 564 and the lysed material 566, respectively, while blocking the particulate lysing material 570. The container 512 may include one or more structures, for example, tabs or annular ridges 576*a*, 576*b* to retain the first and second filters 572*a*, 572*b* in place. Filters may, for example take the form of nylon or stainless steel mesh filter.

The embodiments of FIGS. 1A-5 may advantageously allow extremely high packing densities. In these embodiments, the volume of particulate material may advantageously exceed the volume of material to be lysed or may exceed the volume of material that has been lysed. Additionally or alternatively, these embodiments may advantageously have essentially no air in the chamber. As used herein, essentially no air means that the chamber is free of air other than small bubbles which may be unintentionally entrapped in the chamber. Such may increase lysing efficiency and prevent undesirable heating of the system from friction associated with liquid-air contact line motions.

Figure 6:
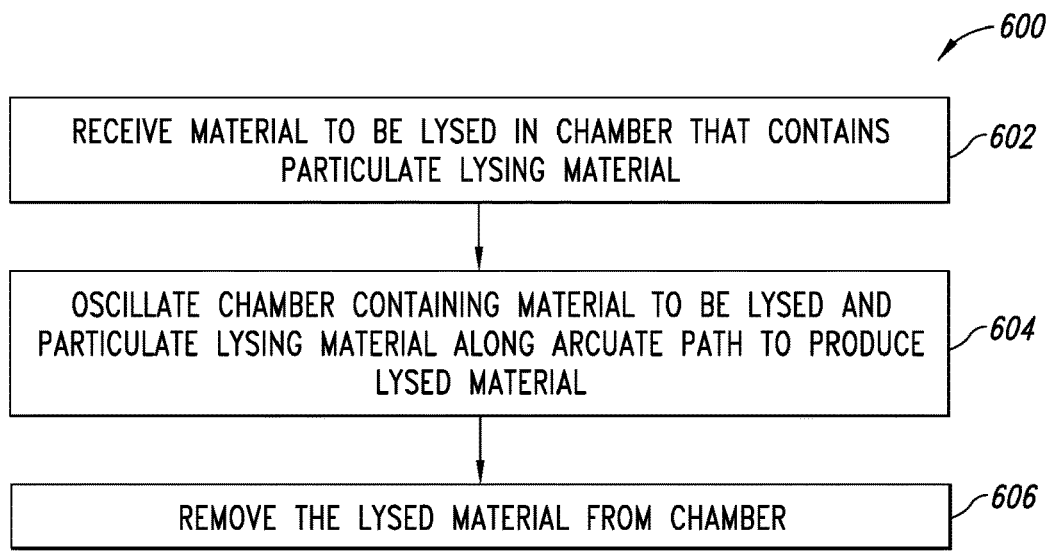
FIG. 6 is a flow diagram of a method of operating an apparatus, such as the apparatus of FIGS. 1A-4, to perform lysing.

FIG. 6 shows a method 600 of operating an apparatus such as that illustrated in FIGS. 1A-4 to lyse material, according to one illustrated embodiment.

At 602, material to be lysed is received in the chamber of the container. The chamber may already hold lysing particulate material. At 604, the container is oscillated along an arcuate path. The oscillation produces large variations in movement between respective ones of the lysing particulate material. Such variations are more pronounced than in translational or rotational movements. At 606, the lysed material is removed from the chamber of the container.

Figure 7:
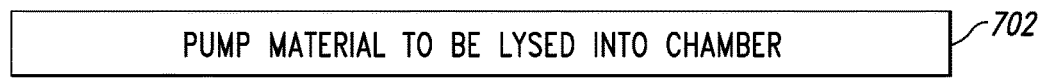
FIG. 7 is a flow diagram of a method of pumping material to be lysed in a flow-through lysing system such as that of FIG. 4 according to one embodiment.

FIG. 7 shows a method 700 of pumping material to be lysed in a flow-through lysing system such as the one of FIG. 4, according to one illustrated embodiment.

At 702, the material to be lysed is pumped into the chamber of the container.

Figure 8:
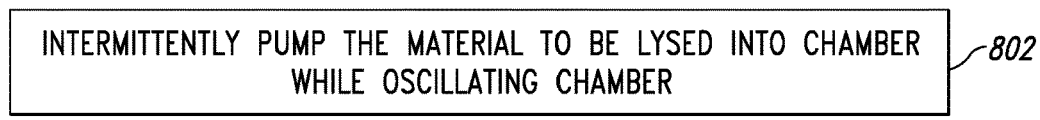
FIG. 8 is a flow diagram of a method of pumping material to be lysed in a flow-through lysing system such as that of FIG. 4, according to another illustrated embodiment.

FIG. 8 shows a method 800 of pumping material to be lysed in a flow-through lysing system such as that of FIG. 4, according to one illustrated embodiment.

At 802, the material to be lysed is intermittently pumped into the chamber of the container while the container is oscillated. Such is suitable for the flow-through stop or semi-batch mode.

Figure 9:
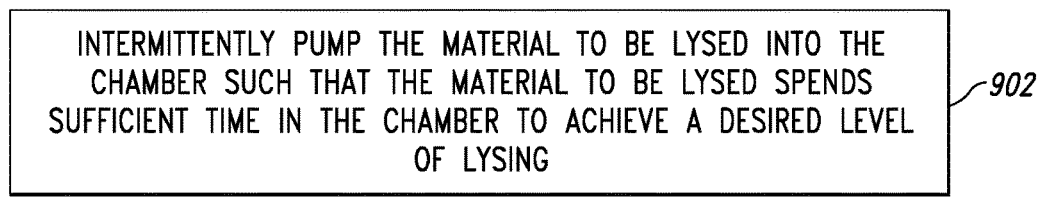
FIG. 9 is a flow diagram of a method of pumping material to be lysed in a flow through lysing system such as that of FIG. 4, according to yet another illustrated embodiment.

FIG. 9 shows a method 900 of pumping material to be lysed in a flow-through lysing system such as that of FIG. 4, according to another illustrated embodiment.

At 902, the material to be lysed is intermittently pumped into the chamber such that the material to be lysed spends a sufficient time in the chamber to achieve a desired level of lysing. Thus, if is determined that 30 seconds of oscillation achieves a desired level of lysing, the pump may be intermittently operated to load the chamber with material to be lysed approximately every 30 seconds. Oscillation times of few seconds or tenths of seconds may be suitable. Such operation is suitable for the flow-through stop or semi-batch mode.

Figure 10:
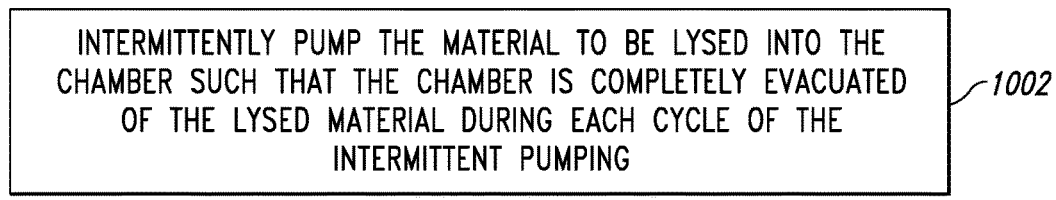
FIG. 10 is a flow diagram of a method of pumping material to be lysed in a flow-through lysing system such as that of FIG. 4, according to still another illustrated embodiment.

FIG. 10 shows a method 1000 of pumping material to be lysed in a flow-through lysing system such as that of FIG. 4, according to another illustrated embodiment.

At 1002, the material to be lysed is intermittently pumped into the chamber such that the chamber is completely evacuated of the lysed material during each cycle of the intermittent pumping. Such is suitable for the flow-through stop or semi-batch mode.

Figure 11:
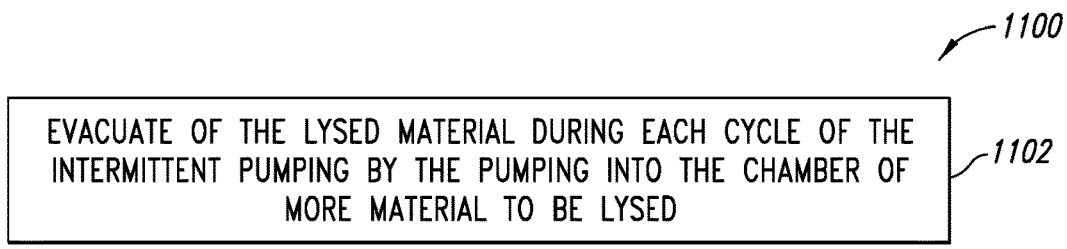
FIG. 11 is a flow diagram of a method of evacuating lysed material in a flow-through lysing system such as that of FIG. 4, according to one illustrated embodiment.

FIG. 11 shows a method 1100 of evacuating lysed material in a flow-through lysing system such as that of FIG. 4, according to another illustrated embodiment.

At 1102, the chamber is evacuated of the lysed material during each cycle of the intermittent pumping by pumping into the chamber more material to be lysed. Such is suitable for the flow-through stop or semi-batch mode.

Figure 12:
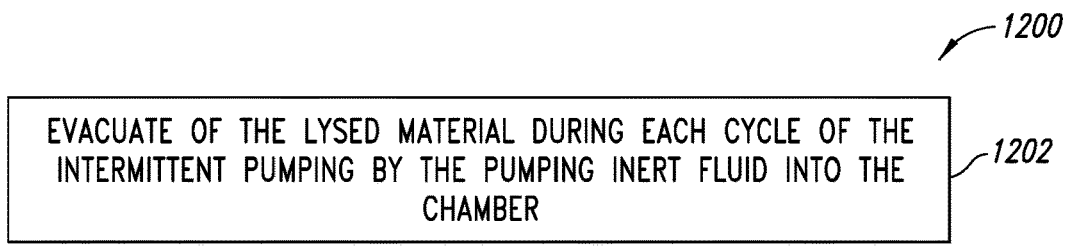
FIG. 12 is a flow diagram of a method of evacuating lysed material in a flow-through lysing system such as that of FIG. 4, according to another illustrated embodiment.

FIG. 12 shows a method 1200 of operating a lysing apparatus such as that of FIG. 4, according to another illustrated embodiment.

At 1202, the chamber is evacuated of the lysed material each cycle of the intermittent pumping by pumping an inert fluid into the chamber. The inert fluid may take the form of a liquid or gas, and may be immiscible with the lysed material or material to be lysed. Such is suitable for the flow-through stop or semi-batch mode.

Figure 13:
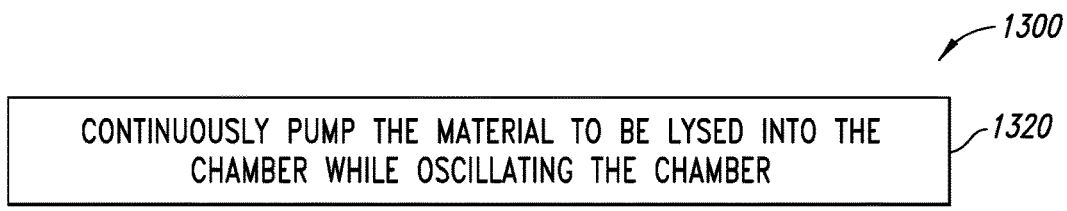
FIG. 13 is a method of pumping material to be lysed in a flow-through lysing system such as that of FIG. 4, according to a further illustrated embodiment.

FIG. 13 shows a method 1300 of operating a continuous lysing apparatus, according to one illustrated embodiment.

At 1302, the material to be lysed is continuously pumped into the chamber of the container while the container is oscillated. Such is suitable for the flow-through continuous mode.

Figure 14:
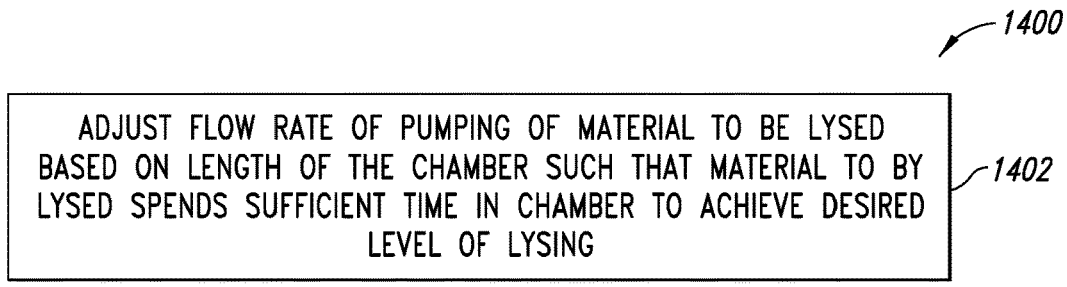
FIG. 14 is a flow diagram of a method of pumping material to be lysed in a flow-through lysing system such as that of FIG. 4, according to still a further illustrated embodiment.

FIG. 14 shows a method 1400 of operating a flow-through lysing apparatus, according to another illustrated embodiment.

At 1402, a flow rate of the pumping of the material to be lysed is adjusted based at least in part on the length and free volume of the chamber such that the material to be lysed spends sufficient time in the chamber (i.e., desired or defined residence time) to achieve a desired level of lysing. Such is suitable for the flow-through continuous mode.

Figure 15:
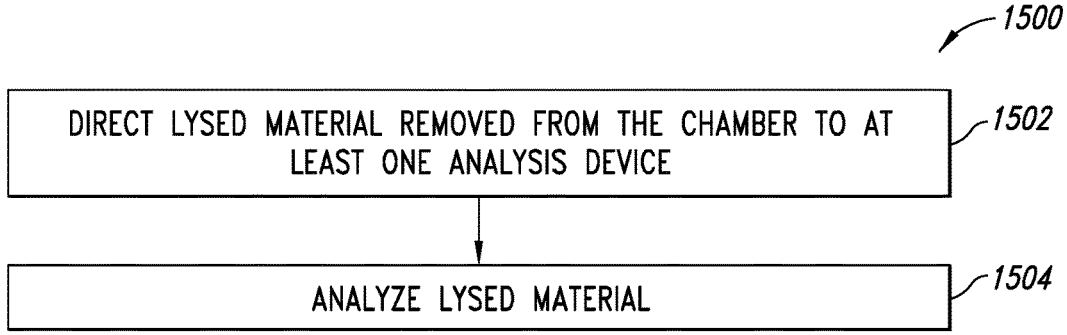
FIG. 15 is a method of operating a flow-through lysing system such as that of FIG. 4 to analyze lysed material, according to one illustrated embodiment.

FIG. 15 shows a method 1500 of operating a flow-through lysing apparatus, such as that of FIG. 4, according to another illustrated embodiment.

At 1502, the lysed material removed from the chamber of the container is directed to at least one analysis device. At 1504, the lysed material is analyzed. Analysis may take a variety of forms, for example analysis with electron-microscope, western blotting, mass spectrometry, gas chromatography, etc. Such is suitable for any of the modes, and particularly suited to the flow-through modes.

Figure 16:
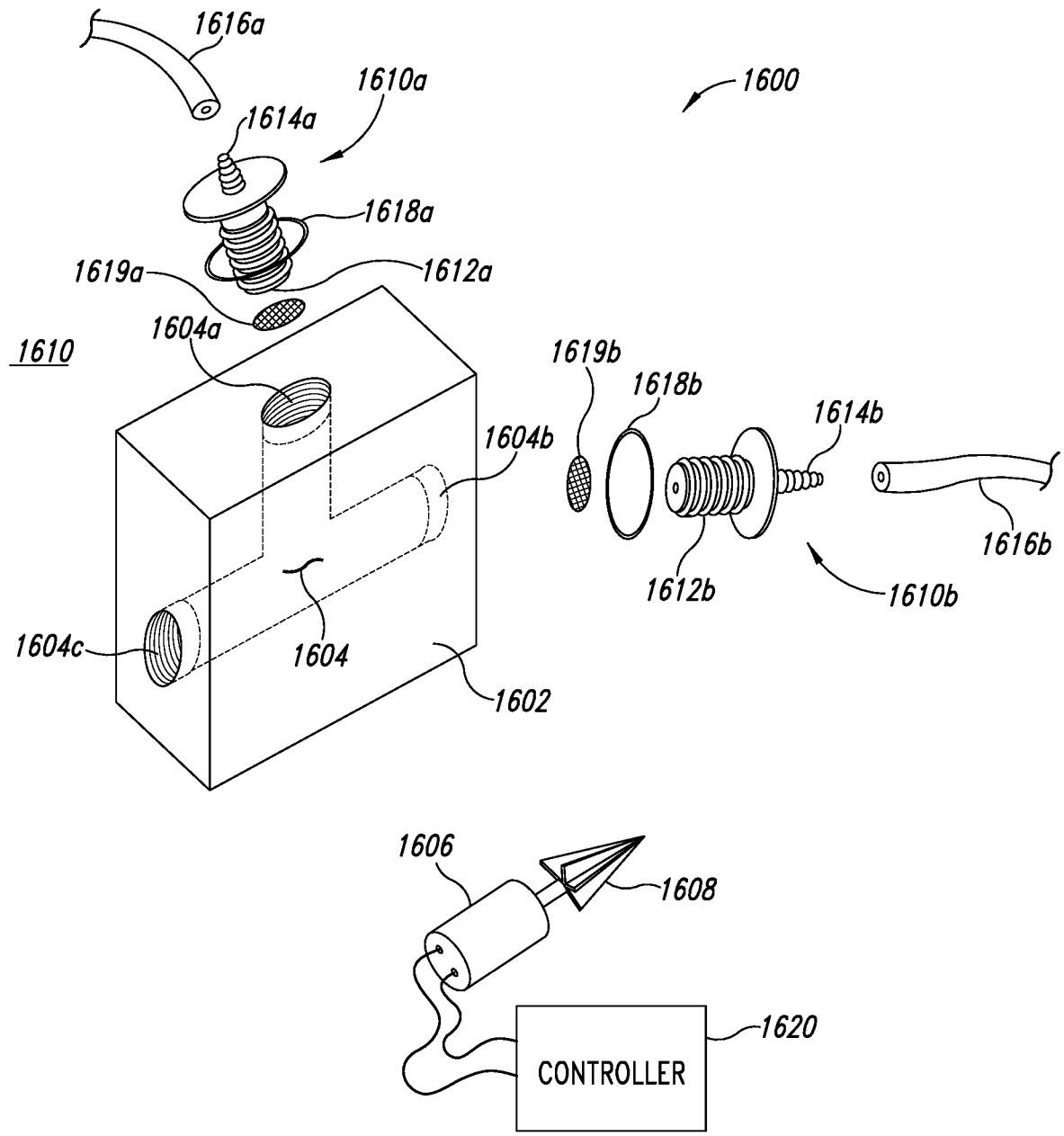
FIG. 16 is an exploded isometric view of a lysing apparatus according to another illustrated embodiment.

FIG. 16 shows a flow-through lysing apparatus 1600 according to another illustrated embodiment. As described in more detail herein, the flow through lysis system 1600 may be operated in a flow-through stop or semi-batch mode, or in a continuous flow mode.

The flow-through lysing apparatus 1600 includes a container 1602 having a chamber 1604, and a micromotor 1606 coupled to drive an impeller 1608.

As illustrated, the chamber 1604 may have a first opening 1604a that serves as an entrance providing fluid communication from an exterior 1610 of the container 1602 to the chamber 1604. Also as illustrated, the chamber 1604 may have a second opening 1604b that serves as an exit, providing fluid communication from the chamber 1604 to the exterior 1610. The container 1602 may further have a third opening 1604c sized to receive the impeller 1608 and to sealingly engage an outer portion of the micromotor 1606. Some embodiments may include a bushing or O-ring to form or enhance the sealing between the micromotor 1606 and third opening 1604c.

A first coupler 1610a may include a stem 1612a sized to be sealingly received in the opening 1604a to provide fluid communication into the chamber 1604. The stem 1612a may be threaded with the hole 1604a having a complementary thread. The first coupler 1610a may include an attachment structure, for example, a ribbed nipple 1614a to secure a tube 1616a and provide a flow of material to be lysed to the chamber 1604. An O-ring 1618a, or other similar structure, may enhance a seal between a flange of the first coupler 1610a and the container 1602.

A second coupler 1610b may include a stem 1612b sized to be sealingly received in the opening 1604b to provide fluid communication into the chamber 1604. The stem 1612b may be threaded with the hole 1604b having a complementary thread. The second coupler 1610b may include an attachment structure, for example, a ribbed nipple 1614b to secure a tube 1616b and provide a flow of material to be lysed to the chamber 1604. An O-ring 1618b, or other similar structure, may enhance a seal between a flange of the second coupler 1610b and the container 1602.

Filters 1619a, 1619b may be positioned in the chamber to retain lysing particulate material therebetween. The filters 1619a, 1619b may, for example, take the form of nylon mesh filters with 50 micron openings mounted to suitable fittings.

The micromotor 1606 may, for example, take the form of a micromotor having a 4 mm diameter, and may be capable of driving the impeller at high speed, for example approximately 50,000 RPM, when not in the presence of liquid and beads. The impeller 1608 may be a nylon or acrylic impeller having a number of vanes. The vanes may be straight, without curvature or angle of attachment, such that movement of material is primarily circumferential. Should axial/horizontal movement of the material through the chamber be desirable, for example in a flow-through mode (e.g., FIGS. 16 and 17), such axial or flow movement comes from pumping and not from rotation of the impeller. This allows more precise control over amount of time that the material remains in the chamber and hence is subject to lysis. The vanes may, for example, produce a periodic flow at a frequency nearly 5 times as high as the embodiments of FIGS. 1A-4, however with a smaller amplitude of motion.

The lysing apparatus 1600 may also include a controller 1620 coupled to control the micromotor 1606. The controller 1620 may, for example include a motor controller and/or a programmed general purpose computing system, a special purpose computer, an application specific integrated circuit (ASIC) and/or field programmable gate array (FPGA). The controller 1620 may for example, be programmed or configured to cause the motor to pulsate. Pulsating may increase the effectiveness of the lysing.

Figure 17:
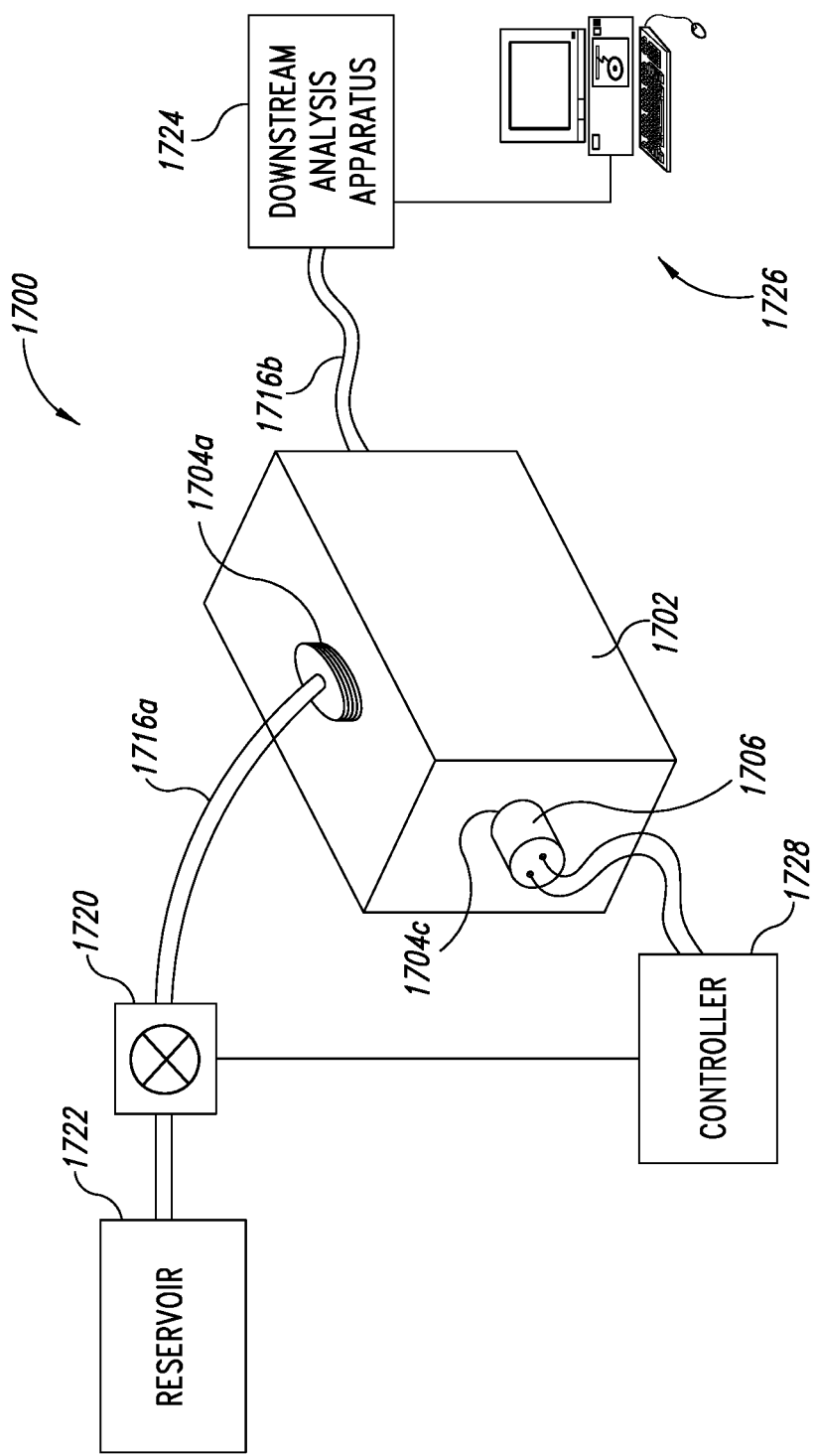
FIG. 17 is a schematic diagram of a lysing system including a lysing apparatus, an upstream subsystem to provide material to be lysed, a downstream subsystem to analyze material that has been lysed, and a control subsystem, according to another illustrated embodiment.

FIG. 17 shows a flow-through lysing system 1700 according to one illustrated embodiment. As described in more detail herein, the flow-through lysis system 1700 may be operated in a flow-through stop or semi-batch mode, or in a continuous flow mode.

The flow-through lysing system 1700 includes a container 1702 having a chamber (not illustrated in FIG. 17), openings 1704a, 1704c (only two illustrated), and a micromotor 1706 coupled to an impeller (not shown in FIG. 17). The opening or entrance 1704 may be fluidly communicatively coupled to a pump 1720 that delivers material to be lysed from a reservoir 1722 via a first conduit or tube 1716a. A second opening or exit may deliver lysed material to one or more downstream analysis apparatus 1724 via one or more conduits such as tubes 1716b. As previously noted, downstream analysis may take a variety of forms, for instance nucleic acid amplification, electrophoresis, western blotting, mass spectrometry, gas chromatography, etc. The downstream analysis apparatus 1724 may be communicatively coupled to one or more computing systems 1726. The flow-through lysing system 1700 may also include one or more control systems 1728 which may control the micromotor 1706 and/or pump 1720. The control system 1728 may for example synchronize the pumping and oscillation, for example to implement a flow-through stop or semi-batch mode. The control system 1728 may for example control the pumping to attain a desired or defined residence time of the material in the chamber to achieve a desired or defined level of lysing, for example to implement a flow-through continuous mode.

The embodiments of FIGS. 16 and 17 may advantageously allow extremely high packing densities. In these embodiments, the volume of particulate material may advantageously exceed the volume of material to be lysed or may exceed the volume of material that has been lysed. Additionally or alternatively, these embodiments may advantageously have essentially no air in the chamber. As used herein, essentially no air means that the chamber is free of air other than small bubbles which may be unintentionally entrapped in the chamber. Such may increase lysing efficiency and prevent undesirable heating of the system from friction associated with liquid-air contact line motions.

Figure 18:
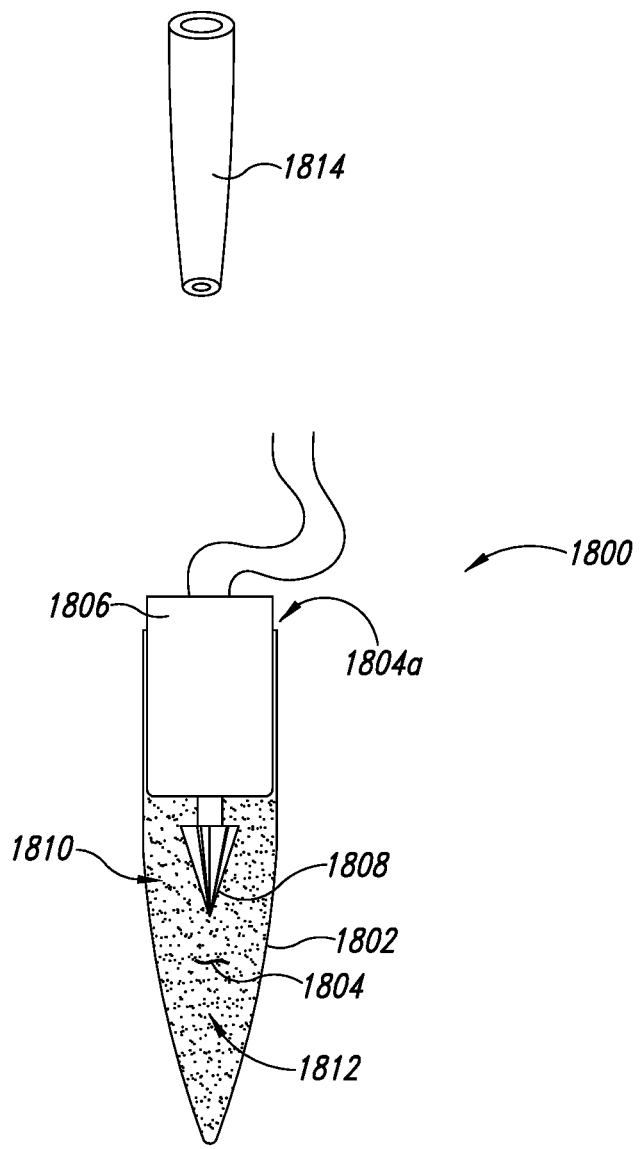
FIG. 18 is a front elevation view of a lysing apparatus and pipette according to one illustrated embodiment.

FIG. 18 shows a lysing system 1800 according to another illustrated embodiment. The lysing system 1800 is particularly suitable for batch mode lysing operations.

The lysing system 1800 includes a container 1802 having a chamber 1804 that has a single opening 1804a to provide fluid communication with an exterior of the container 1802. The apparatus 1800 includes a micromotor 1806 coupled to drive an impeller 1808 that is received in the chamber 1804. A portion of the micromotor 1806 is sized to form a sealing engagement with the container 1802 to seal the opening 1804a. Some embodiments may include one or more bushings or O-rings (not shown) to ensure the seal.

Initially, the chamber 1804 is packed with material to be lysed 1810 and lysing particulate material 1812. After rotation of the impeller 1808, for a sufficient length of time, the chamber 1804 contains material that has been lysed and the lysing particulate material 1812. The micromotor 1806 and impeller 1808 may then be removed and the lysed material may be extracted, for example using a pipette 1814. The chamber 1804 of the batch mode embodiments may not be as densely packed as in flow-through embodiments since room may be required for the apparatus to withdraw the lysed material.

In some embodiments, off-the-shelf vials and tubes may be employed as the container 1802 to hold specimens of material to be lysed and the lysing particulate material, for example PCR or Eppendorf tubes.

The embodiment of FIG. 18 may advantageously allow extremely high packing densities. In these embodiments, the volume of particulate material may advantageously exceed the volume of material to be lysed or may exceed the volume of material that has been lysed. This embodiment is less likely to ensure that there is essentially no air in the chamber since room may be required for receiving the withdrawal apparatus (e.g., pipette). However, where possible, elimination of air in the chamber may increase lysing efficiency and prevent undesirable heating of the system from friction associated with liquid-air contact line motions.

Figure 19:
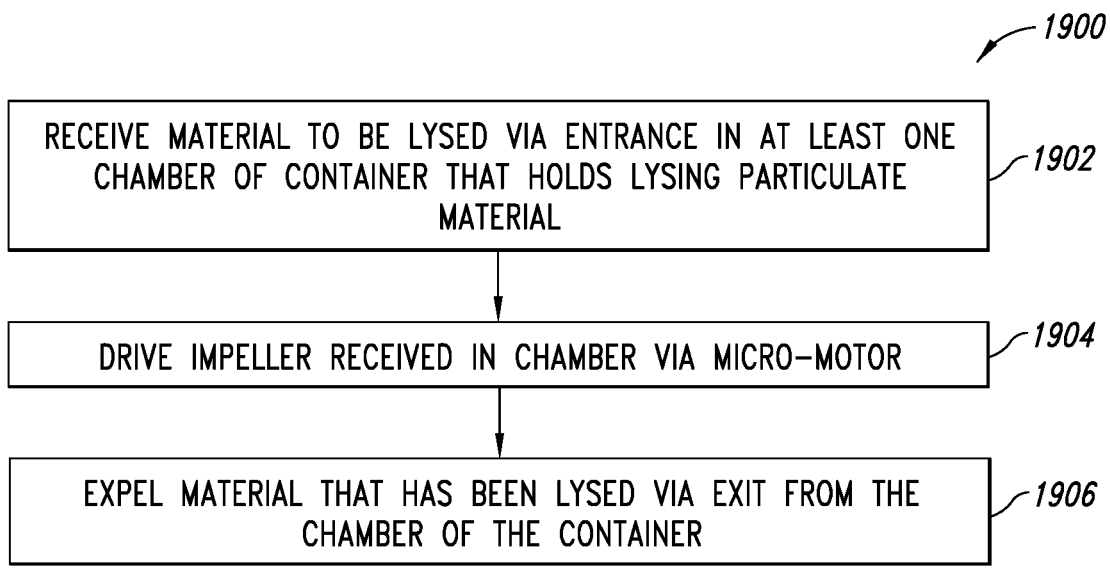
FIG. 19 shows a flow diagram of a method of operating a lysing apparatus such as that of FIGS. 16 and 17, according to one illustrated embodiment.

FIG. 19 shows a method 1900 of operating a flow-through lysing apparatus and/or system according to one illustrated embodiment. Such may be useful in a flow-through stop or semi-batch mode or in a flow-through continuous mode.

At 1902, material to be lysed is received in the chamber of a container via an entrance. The chamber may already hold lysing particulate material. At 1904, the micromotor drives the impeller to cause the lysing particulate material to lyse the material to be lysed. At 1906, material that has been lysed is expelled from the chamber of the container via an exit.

Figure 20:
FIG. 20 is a flow diagram of a method of evacuating material that has been lysed from a chamber in operating a lysing apparatus such as that of FIGS. 16 and 17, according to another illustrated embodiment.

FIG. 20 shows a method 2000 of evacuating material that has been lysed from a chamber, according to one illustrated embodiment.

At 2002, the material that has been lysed may be expelled via a first filter position before the exit in a flow path of material through the apparatus or system.

Figure 21:
FIG. 21 is a flow diagram of a method of receiving material to be lysed in a chamber in operating a lysing apparatus such as that of FIGS. 16 and 17, according to one illustrated embodiment.

FIG. 21 shows a method 2100 of receiving material to be lysed in a chamber, according to another illustrated embodiment.

At 2102, the material to be lysed is received in the chamber via a second filter positioned following the entrance of the chamber in the flow path through the apparatus or system.

Figure 22:
FIG. 22 is a flow diagram of a method of pumping material to be lysed into a chamber in operating a lysing apparatus such as that of FIGS. 16 and 17, according to one illustrated embodiment.

FIG. 22 shows a method 2200 of pumping material to be lysed into a chamber, according to another illustrated embodiment.

At 2202, the material to be lysed is intermittently pumped into the chamber via the entrance. Such may be particularly suitable for flow-through stop or semi-batch mode operation.

Figure 23:
FIG. 23 is a flow diagram of a method of pumping material to be lysed into a chamber in operating a lysing apparatus such as that of FIGS. 16 and 17, according to another illustrated embodiment.

FIG. 23 shows a method 2300 of pumping material to be lysed into a chamber, according to one illustrated embodiment.

At 2302, the material to be lysed is continuously pumped into the chamber of the container via the entrance, at a flow rate that provides for a resident time of the material to be lysed in the chamber that is sufficiently long to achieve a desired or defined level of lysing. The micromotor may continuously drive the impeller to lyse the material. Such may be particularly suitable for flow-through continuous mode operation.

Figure 24:
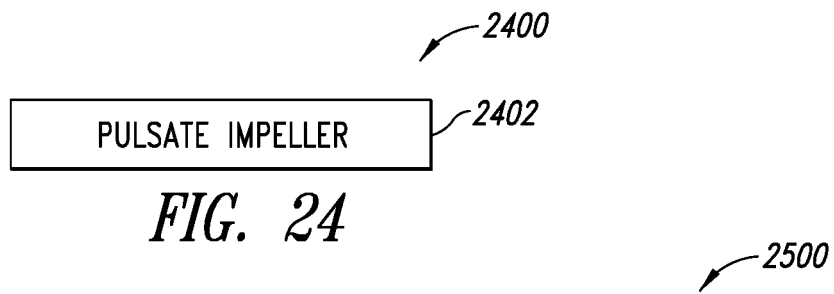
FIG. 24 is a flow diagram of a method of operating an impeller of a lysing system such as that of FIG. 16, 17 or 18, according to one illustrated embodiment.

FIG. 24 shows a method 2400 of operating an impeller of a lysing system, according to one illustrated embodiment.

At 2402, the micromotor pulsatingly drives the impeller. Pulsations may be achieved by varying a voltage or current delivered to the micromotor. Pulsating may achieve a higher efficiency of lysing, thereby increasing throughput or decreasing time required to achieve a desired or defined level of lysing.

Figure 25:
FIG. 25 is a flow diagram of a method of operating an impeller of a lysing system such as that of FIG. 16, 17 or 18, according to one illustrated embodiment.

FIG. 25 shows a method 2500 of operating an impeller of a lysing system according to one illustrated embodiment.

At 2502, the micromotor drives the impeller at greater than 10,000 RPM in the presence of liquid and beads. Driving the impeller at a relatively high speed achieves a desired or defined level of lysing.

Figure 26:
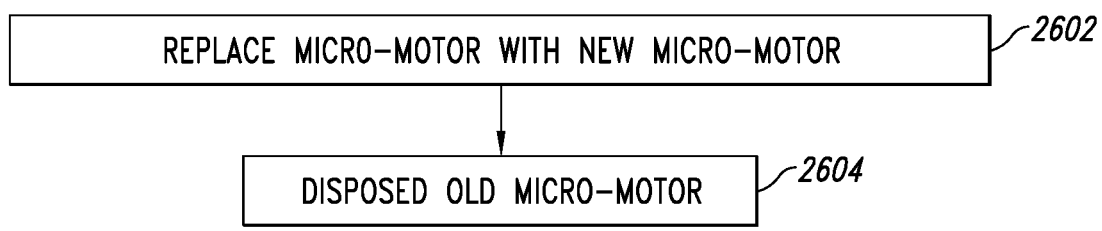
FIG. 26 is a flow diagram of a method of replacing a micromotor of a lysing system such as that of FIG. 16, 17 or 18, according to one illustrated embodiment.

FIG. 26 shows a method 2600 of replacing a micromotor of a lysing system according to one illustrated embodiment.

At 2602, the micromotor may be replaced with a new micromotor. At 2604, the old micromotor may be disposed or recycled. This may be particularly useful since it is difficult to seal the internal elements (e.g., rotor, stator) of the high speed micromotor from exposure to the ambient environment, thus the micromotors may fail more frequently than in other embodiments or environments.

Figure 27:
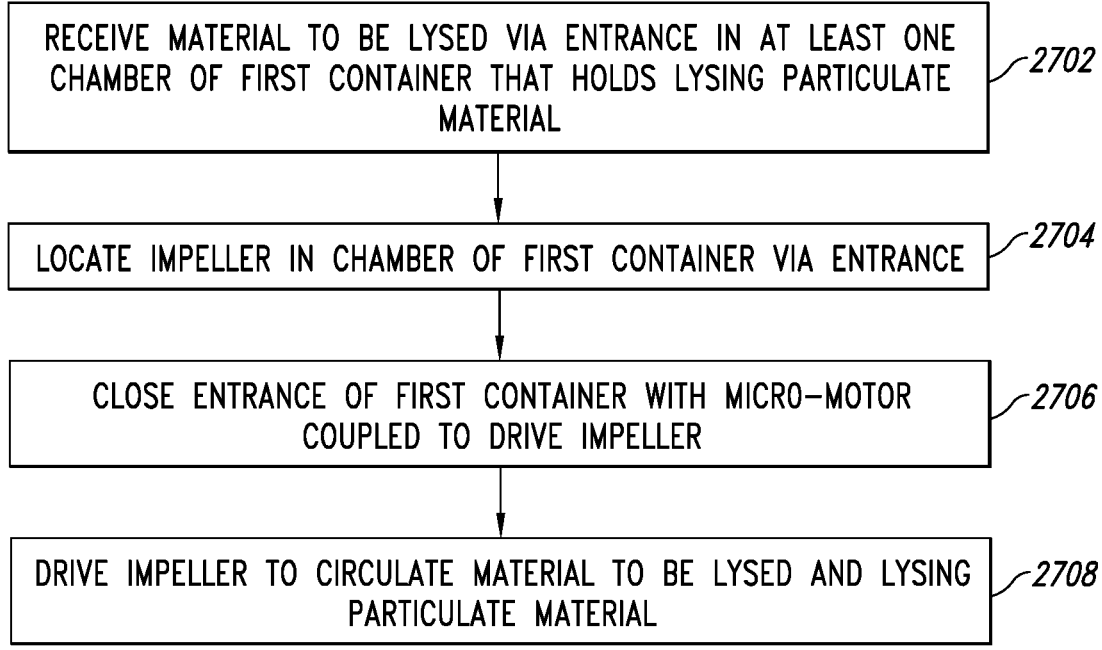
FIG. 27 is a flow diagram of a method of operating a lysing apparatus such as that of FIG. 18, according to one illustrated embodiment.

FIG. 27 shows a method 2700 of operating a batch based lysing apparatus according to one illustrated embodiment. The method 2700 may be particularly useful for use with the embodiment of FIG. 18.

At 2702, material to be lysed is received in a chamber of a first container via an entrance. The chamber may already hold a lysing particulate material or the lysing material may be provided into the chamber with or after the material to be lysed.

At 2704, an impeller is located in the chamber of the first container. At 2706, the entrance to the first container is closed or sealed with a micromotor. At 2708, the micromotor drives the impeller to circulate the material to be lysed and the lysing particulate material. The micromotor may drive the impeller for a sufficient length of time at a sufficient speed until a desired or defined level of lysing has occurred.

Figure 28:
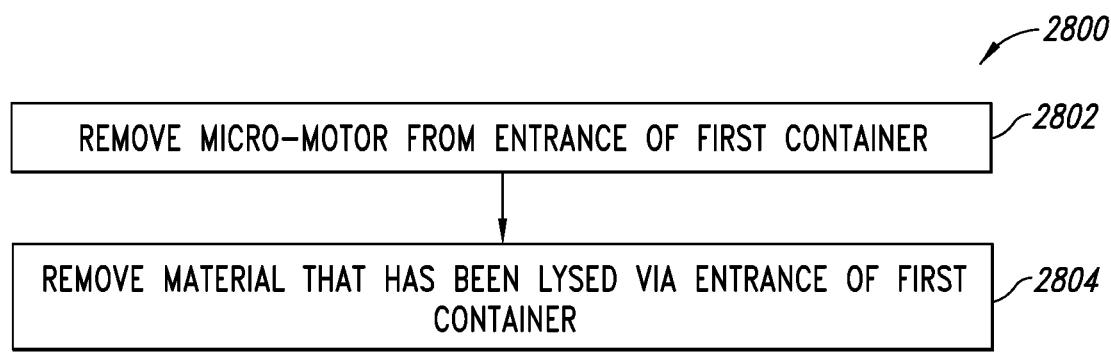
FIG. 28 is a flow diagram of a method of operating a lysing apparatus such as that of FIG. 18, according to one illustrated embodiment.

FIG. 28 shows a method 2800 of operating a lysing apparatus according to one illustrated embodiment. The method 2800 may be particularly useful for use with the embodiment of FIG. 18.

At 2802, the micromotor may be removed from the entrance of the first container. At 2804, the material that has been lysed is removed from the chamber of the first container via the entrance.

Figure 29:
FIG. 29 is a flow diagram of a method withdrawing lysed material from a chamber of a lysing apparatus such as that of FIG. 18, according to one illustrated embodiment.

FIG. 29 shows a method 2900 of removing material that has been lysed according to one illustrated embodiment.

At 2902, the material that has been lysed may be withdrawn using a pipette.

Figure 30:
FIG. 30 is a flow diagram of a method of reusing a micromotor of a lysing apparatus such as that of FIG. 18, according to another illustrated embodiment.

FIG. 30 shows a method 3000 of operating a lysing apparatus according to another illustrated embodiment.

At 3002, the micromotor may be reused with one or more additional containers. It is noted that the micromotor, particularly when operated at high speed, may not be particularly well protected from the material to be lysed, lysing particulate material, or lysed material. Consequently, the micromotor may wear out. In many applications the micromotor may be employed to lyse multiple samples before failing.

Figure 31:
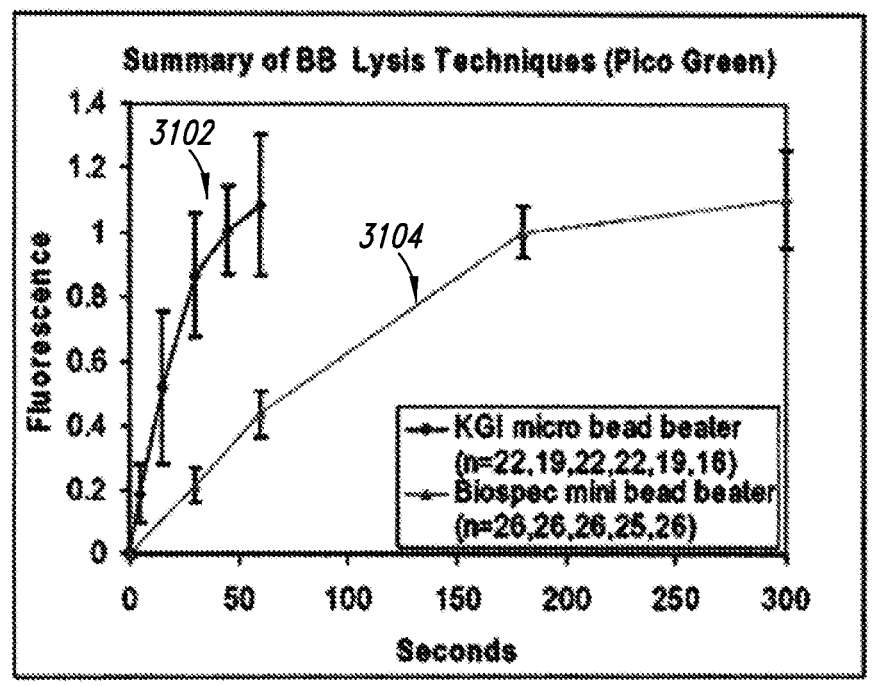
FIG. 31 is a graph showing data representing an efficiency of lysis as a function of lysing duration using an apparatus similar to that of FIG. 4.

FIG. 31 shows data on efficiency of lysis using an apparatus similar to that of FIG. 4.

A first curve 3102 represents measured fluorescence versus time of oscillation using an embodiment similar to that illustrated in FIG. 4. Fluorescence is proportional to the amount of nucleic acid released from cells. A second curve 3105 represents measured fluorescence versus time of oscillation using a commercially available "MINI-BEAD-BEATER-1 product from Biospec Products, Inc. of Bartlesville, Okla. As seen by comparison of the first curve 3102 and second curve 3105, the embodiment of FIG. 4 causes the release of cell contents more efficiently than the commercially available apparatus.

Figure 32:
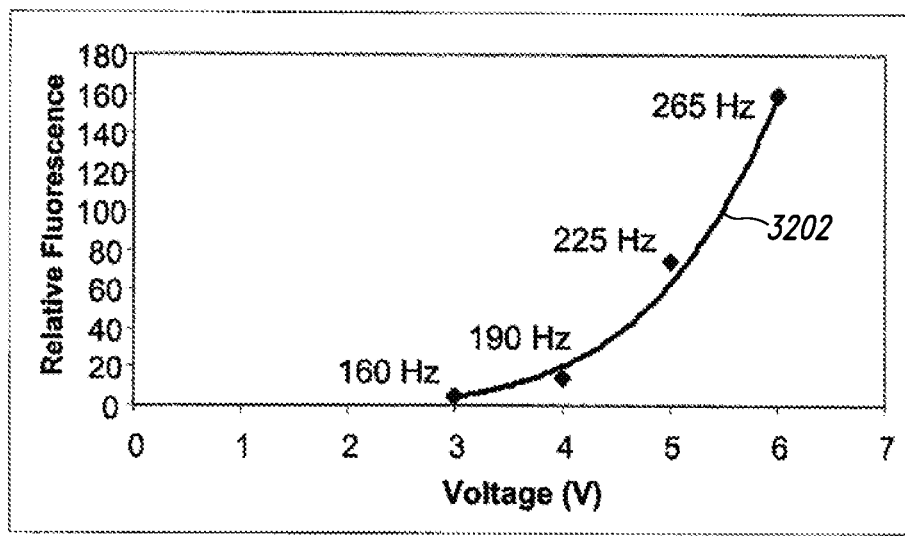
FIG. 32 is a graph showing a dependency of lysis efficiency on frequency of oscillation.

FIG. 32 illustrates a dependency of lysis efficiency on the frequency.

A curve 3202 appears to indicate a nearly quadratic dependence of the degree of lysis on frequency as controlled by changes to the applied voltage for a fixed amount of time.

Figure 33:
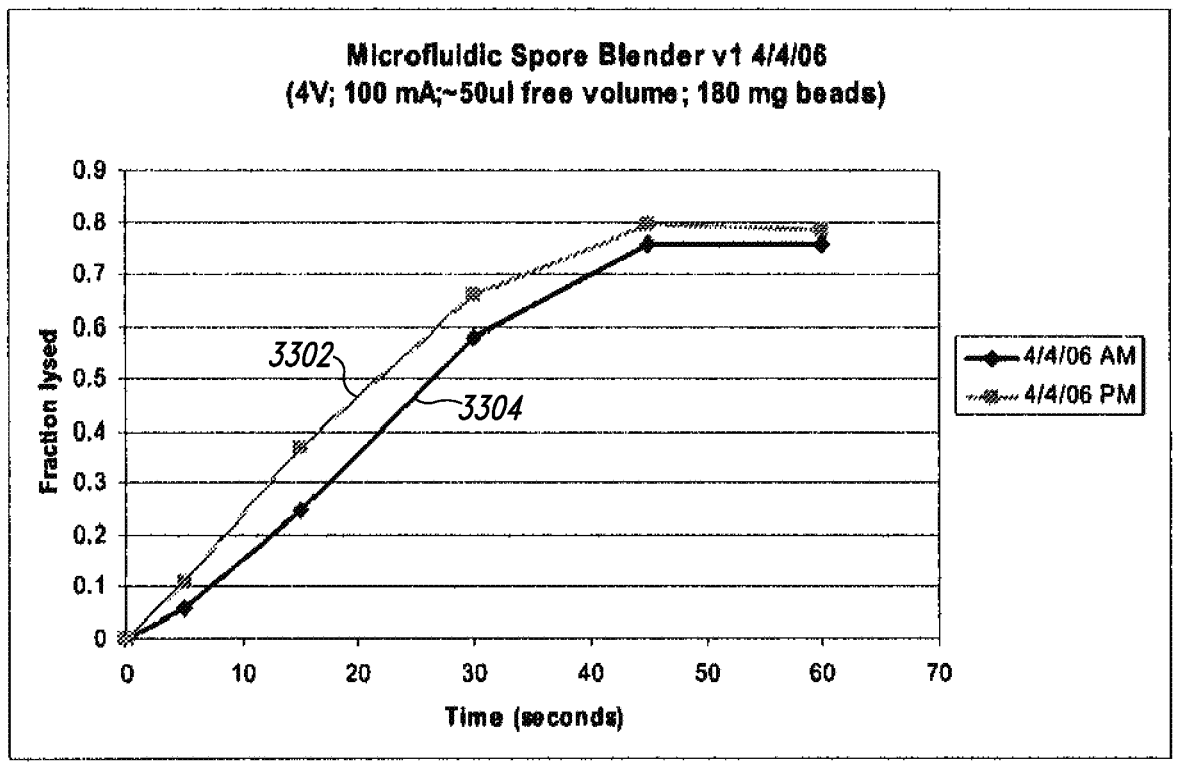
FIG. 33 is a graph showing spore lysis as a function of lysis duration for an apparatus similar to that of the embodiment of FIG. 16.

FIG. 33 shows data representing spore lysis as a function of time for an embodiment similar to that illustrated in FIGS. 16 and 17.

The curves 3302, 3304 illustrate that the time to saturation is comparable to that of the embodiments of FIG. 4, but with peak efficiency of only 80%. The power required for this efficiency was only 400 mW, which is lower than the power used for various other embodiments.

Figure 34:
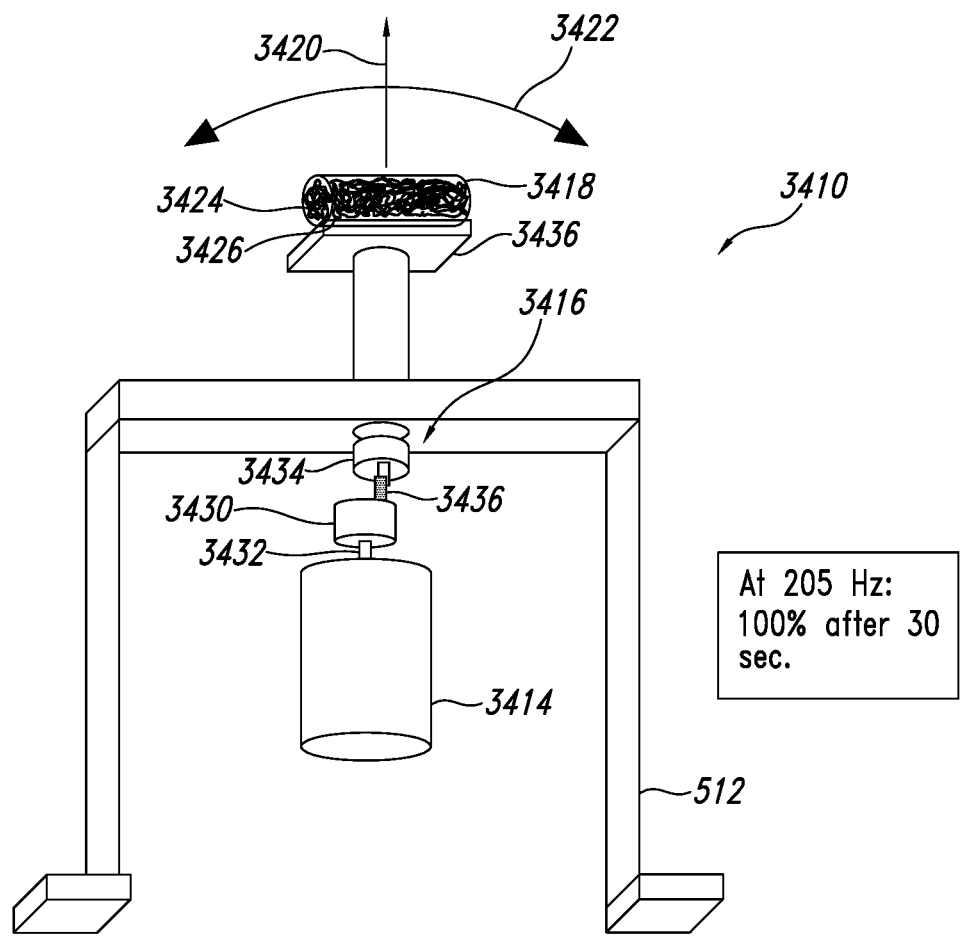
FIG. 34 is an isometric view of a material separation apparatus according to another illustrated embodiment.

FIG. 34 shows a material separation apparatus 3410 according to one illustrated embodiment.

The material separation apparatus 3410 has a base 3412. The material separation apparatus 3410 includes an actuator in the form of an electric motor 3414 and a transmission or drive mechanism 3416 coupled to the base 3412. The electric motor 3414 is selectively operable to drive the drive mechanism 3416 to oscillatingly angularly rotate (i.e., oscillating pivot) a container 3418, about an axis of rotation 3420 as indicated by double headed arrow 3422. Notable in this embodiment, the axis of rotation 3420 passes through a portion of the container 3418. The container 3418 has an interior 3424 that holds material 3426. The material 3426, is material to be separated at a first time, and is separated material at a second time.

The drive mechanism 3416 may include a first drive member 3430 that is rotated by a drive shaft 3432 of the motor 3414. A second drive member 3434 may be coupled to the first drive member 3430 may a connecting rod or member 3436 such that the second drive member eccentrically rotates the container 3418. Other drive members may be employed, for example eccentric gears or cams. The second drive member 3434 is coupled to a holder 3436 to which the container 3418 is removably attached or permanently fixed.

Figure 35B:
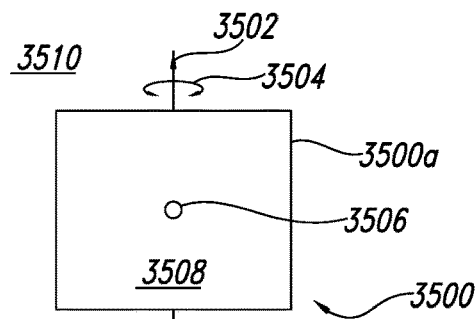
FIG. 35B is a side-elevational view of the container of FIG. 6A.
Figure 35A:
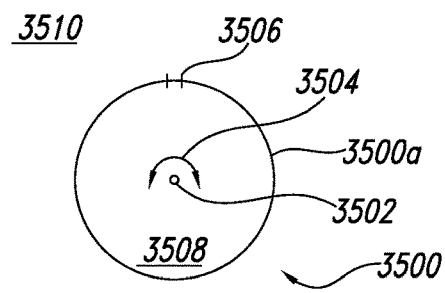
FIG. 35A is a top plan view of a container to hold material to be separated, according to one illustrated embodiment.

FIGS. 35A and 35B show a container 3500 according to one illustrated embodiment.

As illustrated, the container 3500 may have an oval or circular outer periphery. The container 3500 may be mounted concentrically with respect to an axis of rotation 3502, for oscillating angular rotation thereabout as indicated by double headed arrow 3504. Thus, the axis of rotation 3502 passes through a portion of the container 3500.

The container 3500 may include at least one port 3506 to transfer material between an interior 3508 of the container 3500 and an exterior 3510 thereof. The container 3500 may include one or more filters (now shown), which may, for example take the form of nylon or stainless steel mesh filter. One or more of the ports, collectively 3506, may include a valve and/or filter.

Figure 36B:
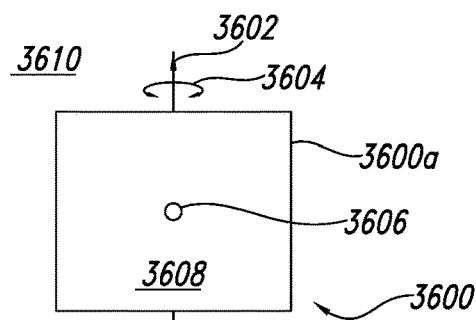
FIG. 36B is a side-elevational view of the container of FIG. 7A.
Figure 36A:
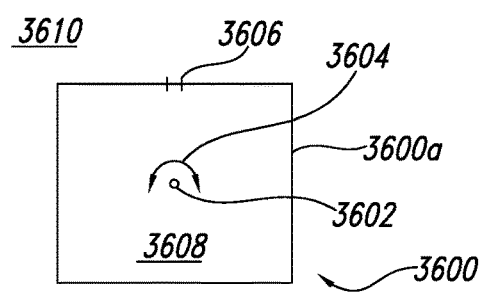
FIG. 36A is a top plan view of a container to hold material to be separated, according to another illustrated embodiment.

FIGS. 36A and 36B show a container 3600 according to one illustrated embodiment.

As illustrated, the container 3600 may have a rectangular or square outer periphery. The container 3600 may be mounted concentrically with respect to an axis of rotation 3602, for oscillating angular rotation thereabout as indicated by double headed arrow 3604. Thus, the axis of rotation 3602 passes through a portion of the container 3600.

The container 3600 may include at least one port 3606 to transfer material between an interior 3608 of the container 3600 and an exterior 3610 thereof. The container 3600 may include one or more filters (now shown), which may, for example take the form of nylon or stainless steel mesh filter. One or more of the ports, collectively 3606, may include a valve and/or filter.

Figure 37B:
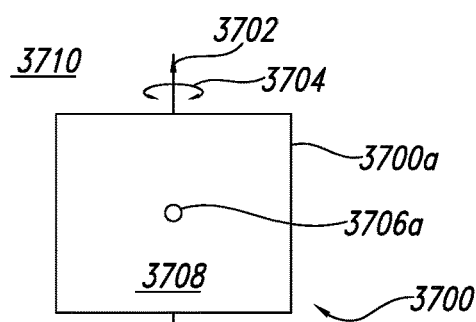
FIG. 37B is a side-elevational view of the container of FIG. 8A.
Figure 37A:
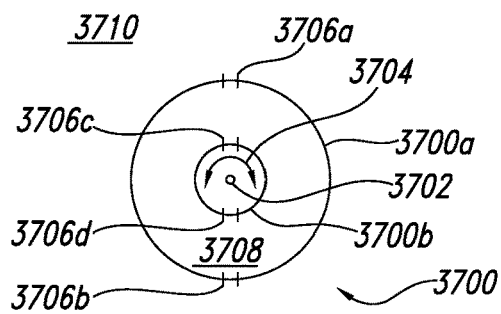
FIG. 37A is a top plan view of a container to hold material to be separated, according to another illustrated embodiment.

FIGS. 37A and 37B show a container 3700 according to one illustrated embodiment.

As illustrated, the container 3700 may have an annular cross-section with an oval or circular outer periphery 3700a and an oval or circular inner periphery 3700b. The container 3700 may be mounted concentrically with respect to an axis of rotation 3702, for oscillating angular rotation thereabout as indicated by double headed arrow 3704. Thus, the axis of rotation 3702 passes through a portion of the container 3700.

The container 3700 may include a number of outer ports 3706a, 3706b to transfer material between an interior 3708 of the container 3700 and an exterior 3710 thereof. In particular, the outer ports 3706a, 3706b may be formed in the outer periphery 3700a of the container 3700. The container 3700 may include a number of inner ports 3706c, 3706d to transfer material between the interior 3708 of the container 3700 and the exterior 3710 thereof. In particular, the inner ports 3706c, 3706d may be formed in the inner periphery 3700b of the container 3700. The container 3700 may include one or more filters (now shown), which may, for example take the form of nylon or stainless steel mesh filter. One or more of the ports, collectively 3706, may include a valve and/or filter.

Figure 38B:
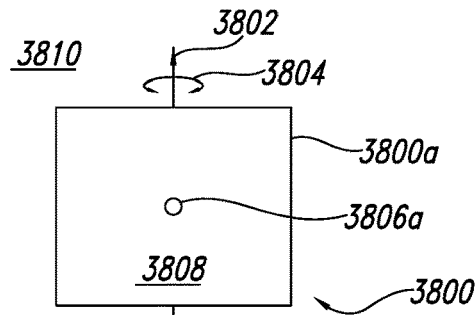
FIG. 38B is a side-elevational view of the container of FIG. 9A.
Figure 38A:
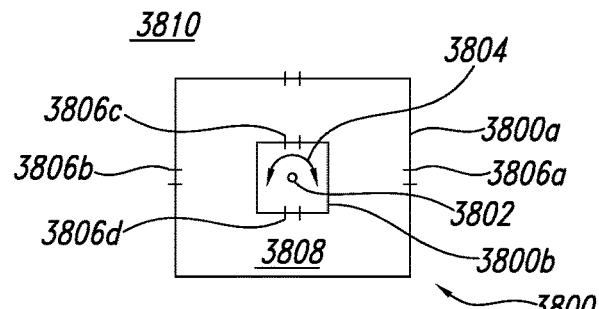
FIG. 38A is a top plan view of a container to hold material to be separated, according to another illustrated embodiment.

FIGS. 38A and 38B show a container 3800 according to one illustrated embodiment.

As illustrated, the container 3800 may have an annular cross-section with an oval or circular outer periphery 3800a and an oval or circular inner periphery 3800b. The container 3800 may be mounted concentrically with respect to an axis of rotation 3802, for oscillating angular rotation thereabout as indicated by double headed arrow 3804. Thus, the axis of rotation 3802 passes through a portion of the container 3800.

The container 3800 may include a number of outer ports 3806a, 3806b to transfer material between an interior 3808 of the container 3800 and an exterior 3810 thereof. In particular, the outer ports 3806a, 3806b may be formed in the outer periphery 3800a of the container 3800. The container 3800 may include a number of inner ports 3806c, 3806d to transfer material between the interior 3808 of the container 3800 and the exterior 3810 thereof. In particular, the inner ports 3806c, 3806d may be formed in the inner periphery 3800b of the container 3800. The container 3800 may include one or more filters (now shown), which may, for example take the form of nylon or stainless steel mesh filter. One or more of the ports, collectively 3806, may include a valve and/or filter.

FIGS. 39A and 39B show a container 3900 according to one illustrated embodiment.

As illustrated, the container 3900 may have an oval or circular cross section with an oval or circular outer periphery 3900a and an oval or circular inner periphery 3900b. The container 3900 may be mounted for oscillating angular rotation about an axis of rotation 3902 as indicated by double headed arrow 3904. Thus, the axis of rotation 3902 does not pass through any portion of the container 3900.

The container 3900 may include a number of outer ports 3906a to transfer material between an interior 3908 of the container 3900 and an exterior 3910 thereof. The container 3900 may include a number of inner ports 3906b to transfer material between the interior 3908 of the container 3900 and the exterior 3910 thereof. In particular, the outer port 3906a may spaced relatively farther from the axis of rotation 3902 than the inner port 3906b. The container 3900 may include one or more filters (now shown), which may, for example take the form of nylon or stainless steel mesh filter. One or more of the ports, collectively 3906, may include a valve and/or filter.

FIGS. 40A and 40B show a container 4000 according to one illustrated embodiment.

As illustrated, the container 4000 may have an oval or circular cross section with an oval or circular outer periphery 4000a and an oval or circular inner periphery 4000b. The container 4000 may be mounted for oscillating angular rotation about an axis of rotation 4002 as indicated by double headed arrow 4004. Thus, the axis of rotation 4002 does not pass through any portion of the container 4000.

The container 4000 may include a number of outer ports 4006a to transfer material between an interior 4008 of the container 4000 and an exterior 4010 thereof. The container 4000 may include a number of inner ports 4006b to transfer material between the interior 4008 of the container 4000 and the exterior 4010 thereof. In particular, the outer port 4006a may spaced relatively farther from the axis of rotation 4002 than the inner port 4006b. The container 4000 may include one or more filters (now shown), which may, for example take the form of nylon or stainless steel mesh filter. One or more of the ports, collectively 4006, may include a valve and/or filter.

Figure 41:
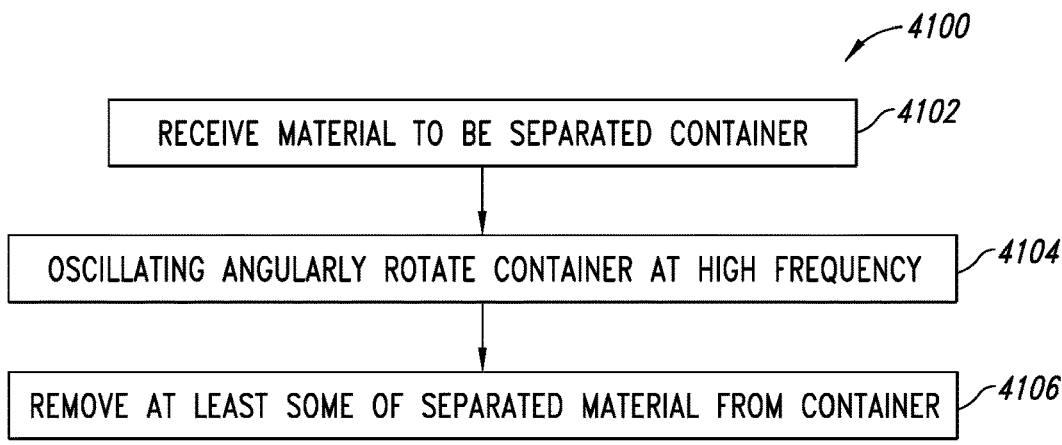
FIG. 41 is a flow diagram of a method of operating a system to separate materials, according to one illustrated embodiment.

FIG. 41 shows a method 4100 of operating an apparatus to separate materials, according to one illustrated embodiment.

At 4102, a material to be separated is received in a container. The material may, for example, include a particulate material in a suspension.

At 4105, the container is oscillating angularly rotated at a high frequency. Such may be implemented by supplying power to a motor to drive a drive mechanism coupled to the container.

At 4106, at least some of the separated material is removed from the container. For example, the relatively dense or heavier material may be removed. The relatively dense or heavier material may collect at a portion of the interior of the container that is relatively closer to an axis of rotation than other portions of the interior of the container. Thus, such dense or heavier material may be removed, for instance, via an inner port of the container. Also for example, the relatively less dense or lighter material may be removed. The relatively less dense or lighter material may collect at a portion of the interior of the container that is relatively farther from an axis of rotation than other portions of the interior of the container. Thus, such less dense or lighter material may be removed, for instance, via an outer port of the container. The separated material being removed may pass through one or more filters to further separate materials.

Figure 42:
FIG. 42 is a flow diagram of a method of operating a system to separate materials, according to another illustrated embodiment.

FIG. 42 shows a method 4200 of operating an apparatus to separate materials, according to one illustrated embodiment.

At 4202, the material to be separated is pumped into the container.

Figure 43:
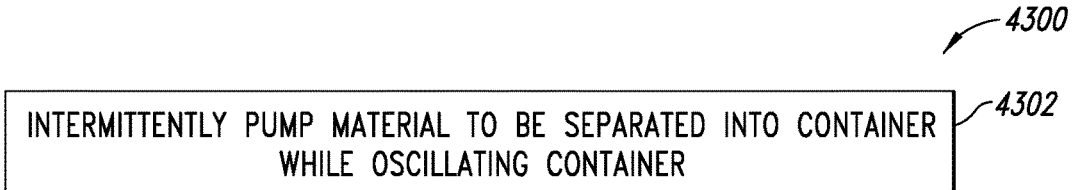
FIG. 43 is a flow diagram of a method of operating a system to separate materials, according to another illustrated embodiment.

FIG. 43 shows a method 4300 of operating an apparatus to separate materials, according to one illustrated embodiment.

At 4302, the material to be separated is intermittently pumped into the container while oscillating the container.

Figure 44:
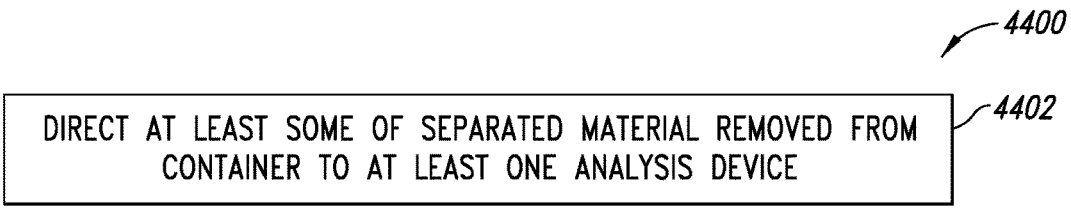
FIG. 44 is a flow diagram of a method of operating a system to separate materials, according to another illustrated embodiment.

FIG. 44 shows a method 4400 of operating an apparatus to separate materials, according to one illustrated embodiment.

At 4402, at least some of the separated material removed from the container is directed to at least one analysis device. Such may be accomplished using gravity flow, pumps, valves, etc.

Figure 45:
FIG. 45 is a flow diagram of a method of operating a system to separate materials, according to another illustrated embodiment.

FIG. 45 shows a method 4500 of operating an apparatus to separate materials, according to one illustrated embodiment.

At 4502, the container is evacuated of the separated materials using an inert fluid. For example the container may be flushed with an inert gas or liquid. Such may prepare the container for a next specimen, sample or batch of material to be separated.

To summarize, apparatus and methods cause separation of particles (e.g., cells, bio-molecules, etc.) in a fluid suspension by imparting angular oscillations to the fluid container, which essentially undergoes oscillatory rigid-body rotation.

Particles whose density is different from the fluid can be separated radially similar to centrifugation. However, the direction of particle motion and accumulation can unexpectedly be opposite to ordinary centrifugation. One can thus collect the relatively heavy or denser particles near the rotation axis while the relatively light or less dense particles are thrown away from the axis of rotation. In contrast, in ordinary centrifugation, particles denser than the fluid move away from the rotation axis.

As taught here, it is shown that if instead of rotating steadily such as in an ordinary centrifuge, the container undergoes high-frequency, purely oscillatory, angular rotation, dense or relatively heavy particles can be made to move toward the rotation axis while light or relatively less dense particles can be moved away from the axis of rotation.

Thus, such provides an approach to separating particles based on their density difference (but also dependent upon their size) in a manner similar to a centrifuge. However, the direction of particle migration can be manipulated (for instance by changing the frequency of oscillations) to be opposite to what one expects in an ordinary centrifuge. Such can potentially be applied to separation of red and white blood cells or other bio-particles or bio-molecules. In addition to particle separation and concentration, one can envision using such for re-suspension of particles that have already been separated in an ordinary centrifuge. For instance, heavy particles are centrifuged out, but are then re-suspended by putting the container in an oscillatory angular rotation mode, rather than in its original steady rotation.

In practice, a particle suspension is introduced into and completely fills a container (for instance a chamber having a square cross-section, thin side walls, and a top cover) and the container is made to undergo oscillatory angular rotations about an axis perpendicular to the centerline of the container (e.g. center of the square cross-section). The frequency and amplitude of oscillations can be varied. Particles migrate radially and collect near the rotation axis or near the side walls, depending on their density and size.

The above approach is based on a theoretical analysis of particle motion, set out below. The theoretical analysis neglects some effects that are assumed to be of minor importance (e.g. Basset history-integral forces and lift forces on the particles as well as hydrodynamic interactions among the particles and between the particles and the walls). These effects may end up being significant and may modify the current predictions. Experimental verification is planned.

Applicants have observed that linear sliding motion is not as effective at lysing spores as the "wagging" or oscillatory motion described herein and in U.S. provisional patent application Ser. No. 61/020,072 filed Jan. 9, 2008, which is incorporated by reference herein in its entirety.

The equations of motion for a bead include:

$$m_p \frac{dV}{dt} = \quad\quad\quad\quad\quad\quad\quad\quad\quad\quad\quad\quad \text{Equation 1}$$

$$m_f \frac{Du}{Dt} - \frac{1}{2} m_f \left( \frac{dV}{dt} - \frac{Du}{Dt} \right) - 6\pi\mu a(V-u) + (m_p - m_f)g$$

Where the first term after the equal sign represents pressure stress, the second term represents added mass, the third term viscous drag and the forth term represents gravity, but can be ignored or neglected.

Where cartridge displacement is represented by:

$$\Delta \sin(\omega t) i \quad\quad\quad\quad\quad\quad\quad\quad\quad\quad\quad \text{Equation 2}$$

And fluid acceleration is represented by:

$$Du/Dt = -\omega^2 \Delta \sin(\omega t) i \quad\quad\quad\quad\quad\quad\quad \text{Equation 3}$$

The equation of motion for the bead becomes:

$$\left(m_p + \frac{1}{2}m_f\right)\ddot{x} = -\frac{3}{2}m_f \omega^2 \Delta \sin(\omega t) - 6\pi\mu a[\dot{x} - \omega\Delta\cos(\omega t)] \quad \text{Equation 4}$$

with initial conditions:

$$x(0)=0 \dot{x}(0)=\omega\Delta. \quad\quad\quad\quad\quad\quad\quad\quad \text{Equation 5}$$

In moving frame and dimensionless, the equation is represented as:

$$\ddot{X} = (1=\alpha)\sin(t) - \beta\dot{X} \quad\quad\quad\quad\quad\quad \text{Equation 6}$$

where $$\alpha = \frac{3m_f}{2m_p + m_f} \quad \beta = \frac{6\pi\mu a}{\omega(m_{p\_}m_f/2)} = St^{-1} \quad \text{Equation 8}$$

and with initial conditions:

$$X(0)=0 \dot{X}(0)=0 \quad\quad\quad\quad\quad\quad\quad\quad \text{Equation 9}$$

The solution is given by:

$$X(t) = (1-\alpha)\left\{ \frac{1}{\beta} - \frac{e^{-\beta t}}{\beta(1+\beta^2)} - \frac{1}{1+\beta^2}[\sin(t) + \beta\cos(t)] \right\} \quad \text{Equation 10}$$

Figure 46:
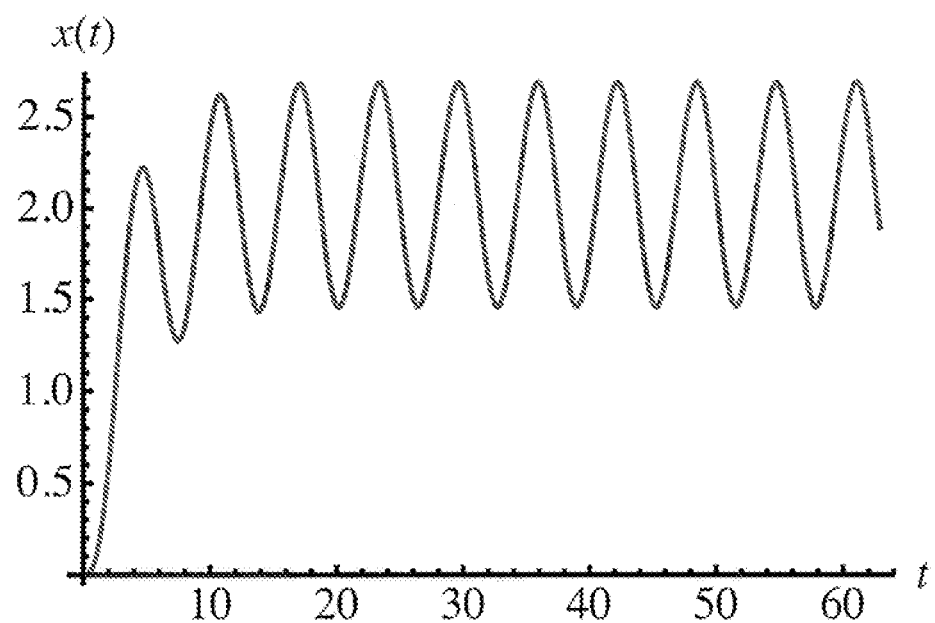
FIG. 46 is a graph showing bead trajectory, linear oscillations.
Figure 47:
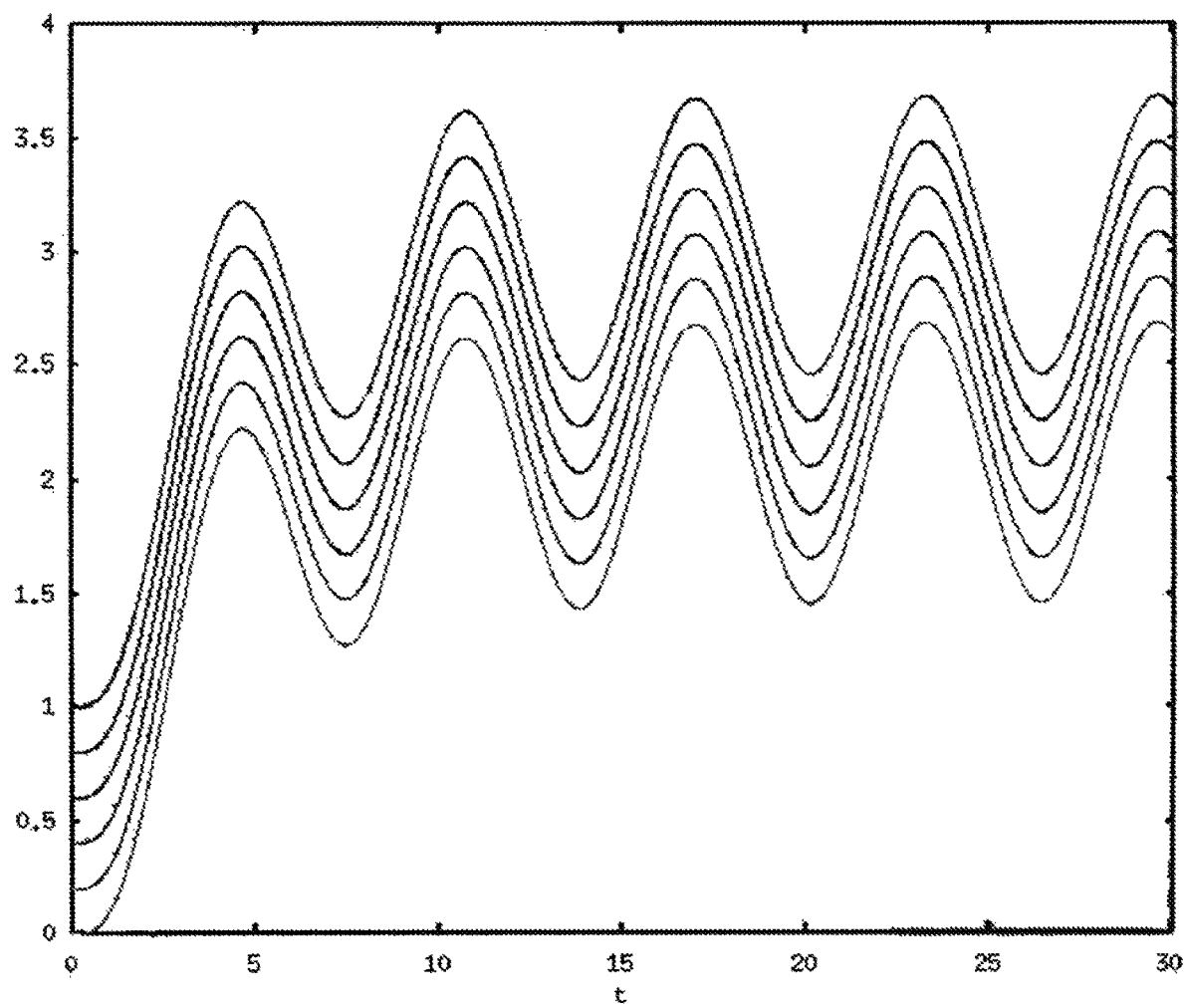
FIG. 47 is a graph showing constant distance b/w neighboring beads.

FIG. 46 shows bead trajectory, linear oscillations.
FIG. 47 shows constant distance b/w neighboring beads.
Oscillatory rotational motion is represented by:

$$\phi(t)=\Delta \sin(\omega t)$$

$$\Omega(t)=\dot{\phi}=\omega\Delta\cos(\omega t)$$

$$\dot{\Omega}(t)=-\omega^2\Delta \sin(\omega t) \quad\quad\quad\quad\quad\quad \text{Equation 11}$$

And fluid acceleration by:

$$\frac{Du}{Dt} = \dot{\Omega} r \hat{e}_\theta - \Omega^2 r \hat{e}_r \quad\quad\quad\quad\quad\quad \text{Equations 12}$$

The equations of motion are represented as:

$$\ddot{r} - r(\dot{\theta})^2 = -\alpha r \omega^2 - \omega\beta\dot{r}$$

$$r\ddot{\theta} + 2\dot{r}\dot{\theta} = \alpha\dot{\Omega}r - \omega\beta r(\dot{\theta}-\omega)$$

$$r(0)=r_o \theta(0)=0 \dot{r}(0)=0 \dot{\theta}(0)=\omega\Delta \quad\quad \text{Equation 13}$$

In rotating frame and dimensionless, the equations of motion are become::

$$\ddot{r}=-\beta\dot{r}+\Delta^2 r[(1-\alpha)\cos^2(t)+2\cos(t)+2\cos(t)\dot{\delta}+\dot{\delta}^2]$$

$$\ddot{\delta}=(1=\alpha)\sin(t)-\beta\dot{\delta}-2(\dot{r}/r)[\dot{\delta}+\cos(t)]$$

$$r(0)=1 \delta(0)=0 \dot{r}(0)=0 \quad\quad\quad\quad\quad \text{Equation 14}$$

with parameters::

$$(1-\alpha) = \frac{m_p - m_f}{m_p + m_f/2}$$ Equations 15

$$\beta = \frac{6\pi\bar{\omega}a}{\omega(m_p + m_f/2)} = St^{-1}$$

Figure 48:
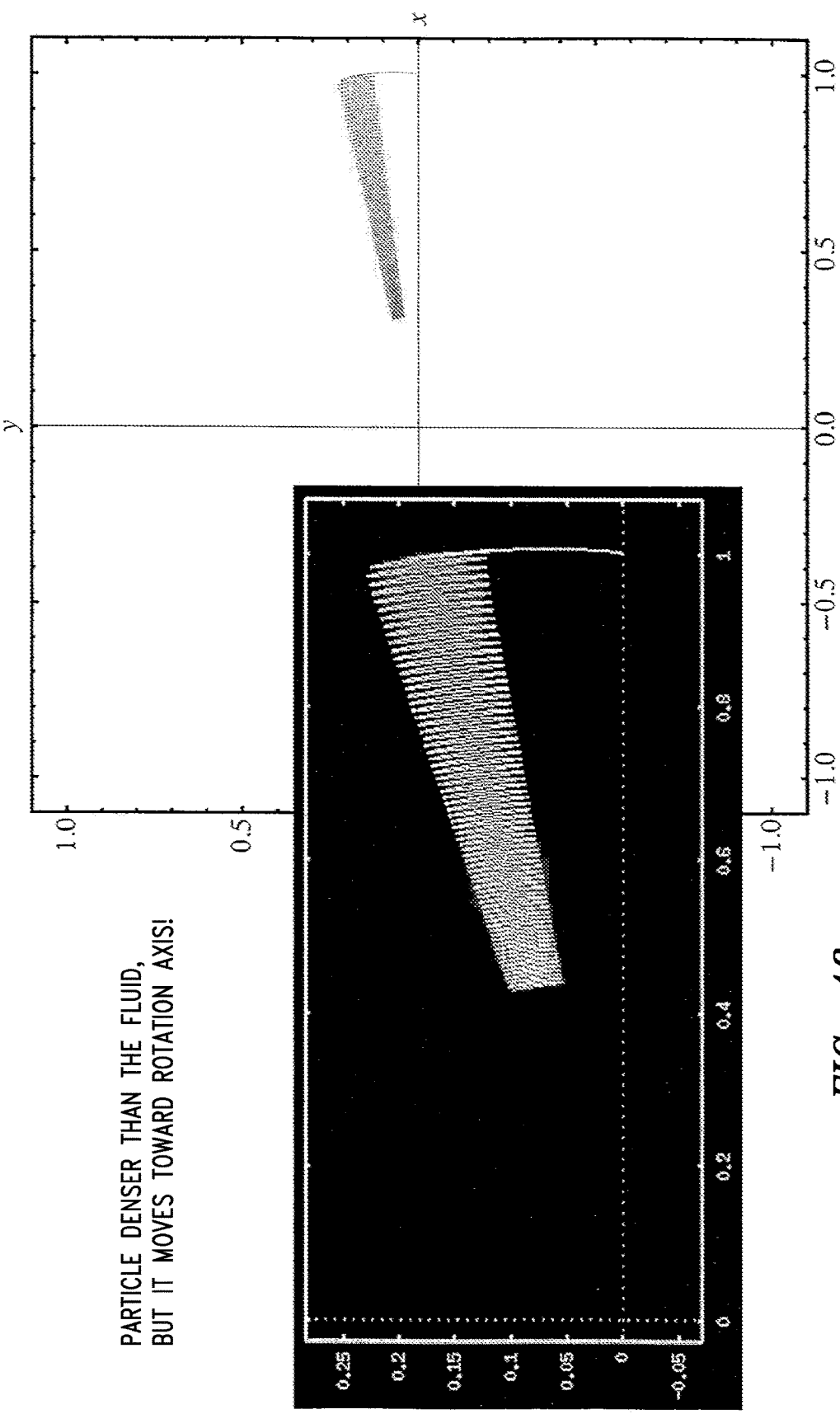
FIG. 48 is a graph showing how particles that are denser or heavier that the fluid may move toward the rotational axis rather than moving away as would have been expected.

FIG. 48 represents how particles that are denser or heavier that the fluid may move toward the rotational axis rather than moving away as would have been expected.

Figure 49:
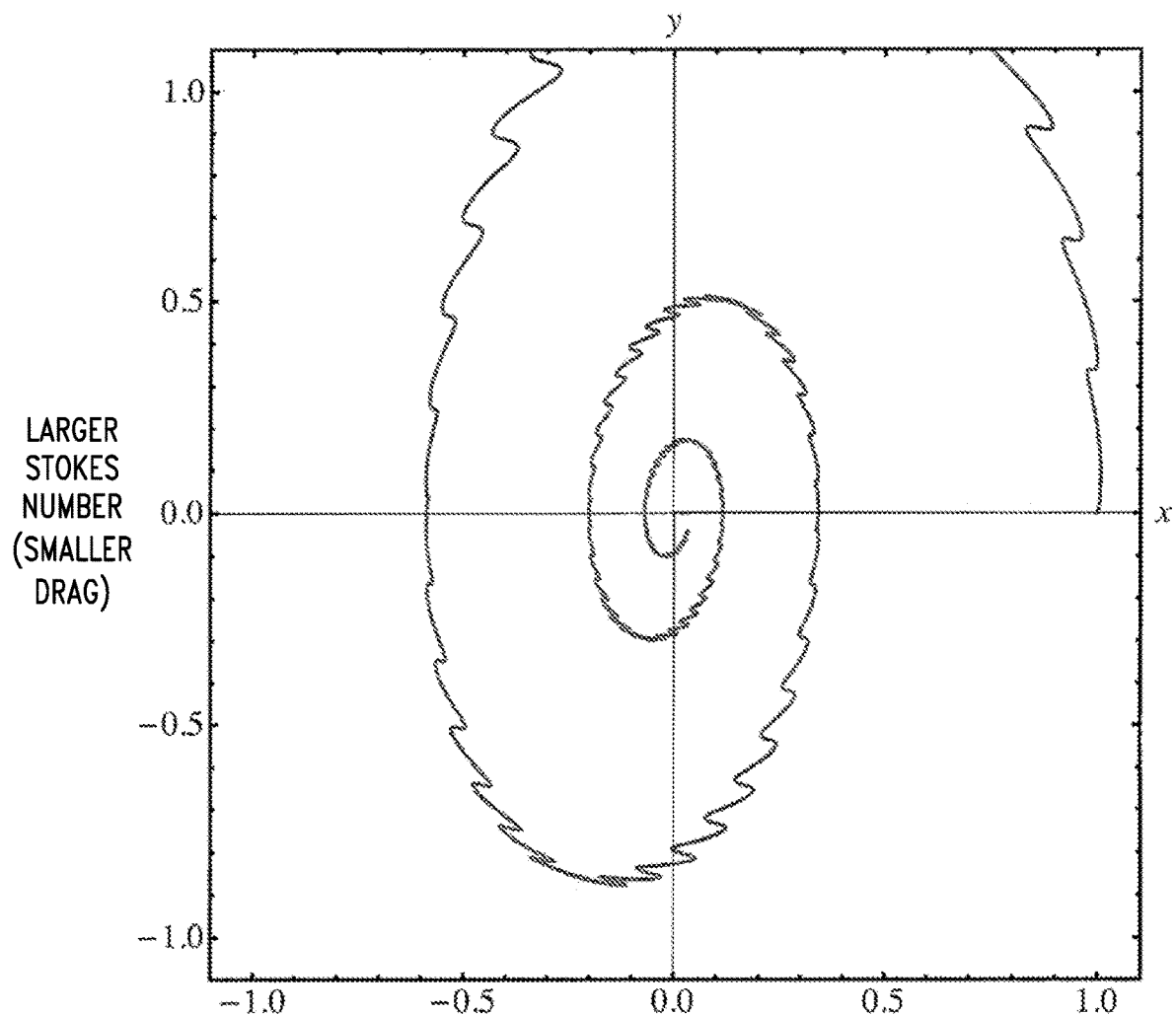
FIG. 49 is a graph showing an effect of a larger Stokes number, hence smaller drag.

FIG. 49 represents the effect of a larger Stokes number, hence smaller drag.

Figure 50:
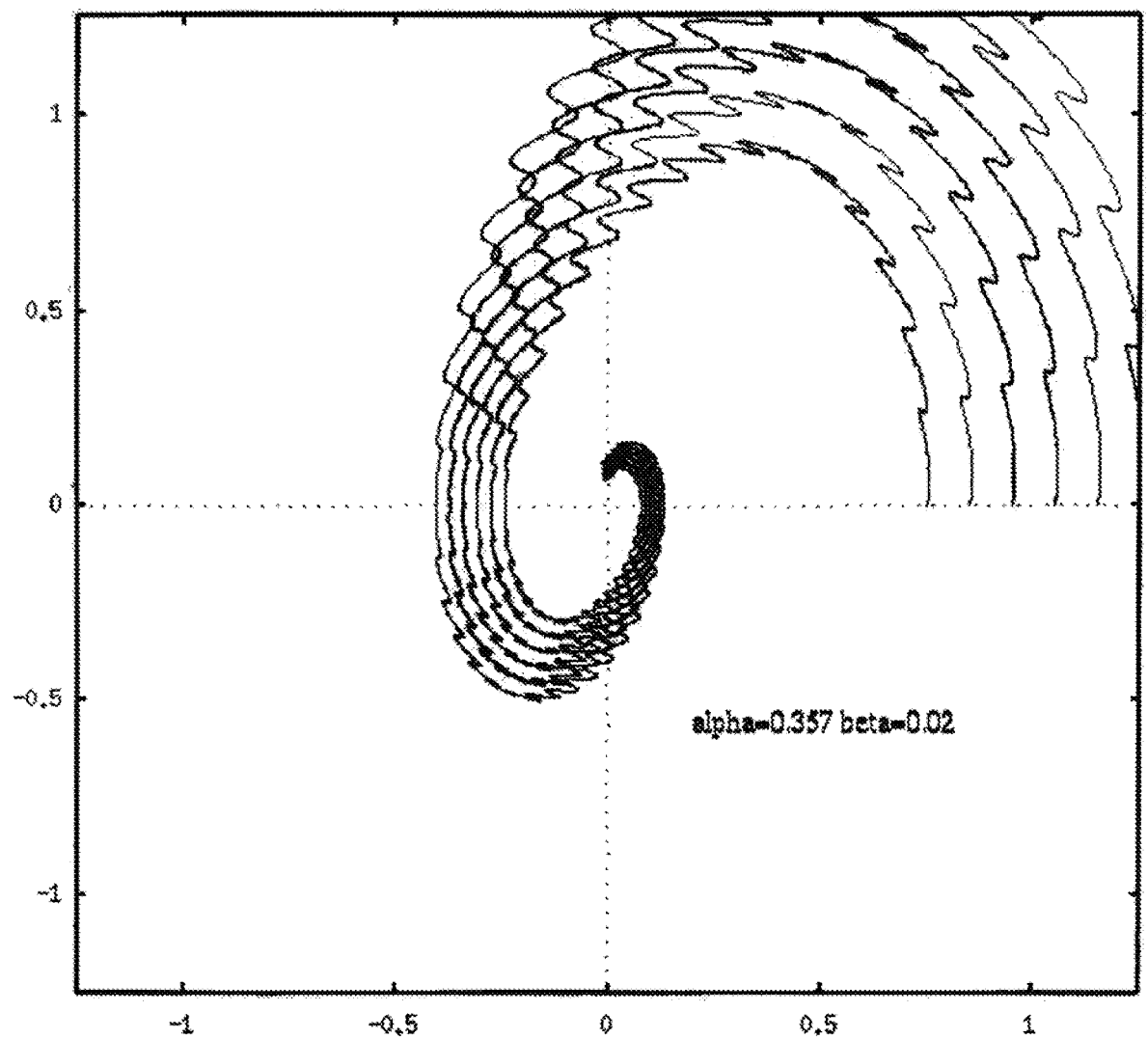
FIG. 50 is a graph showing a convergence of neighboring beads.

FIG. 50 represents convergence of neighboring beads.

An approximate may be made via a method of averaging. Where $$\beta < \sqrt{\alpha}$$

particles move radially inward, while where $$\beta < \sqrt{\alpha}$$

particles move radially outward.

Figure 51A:
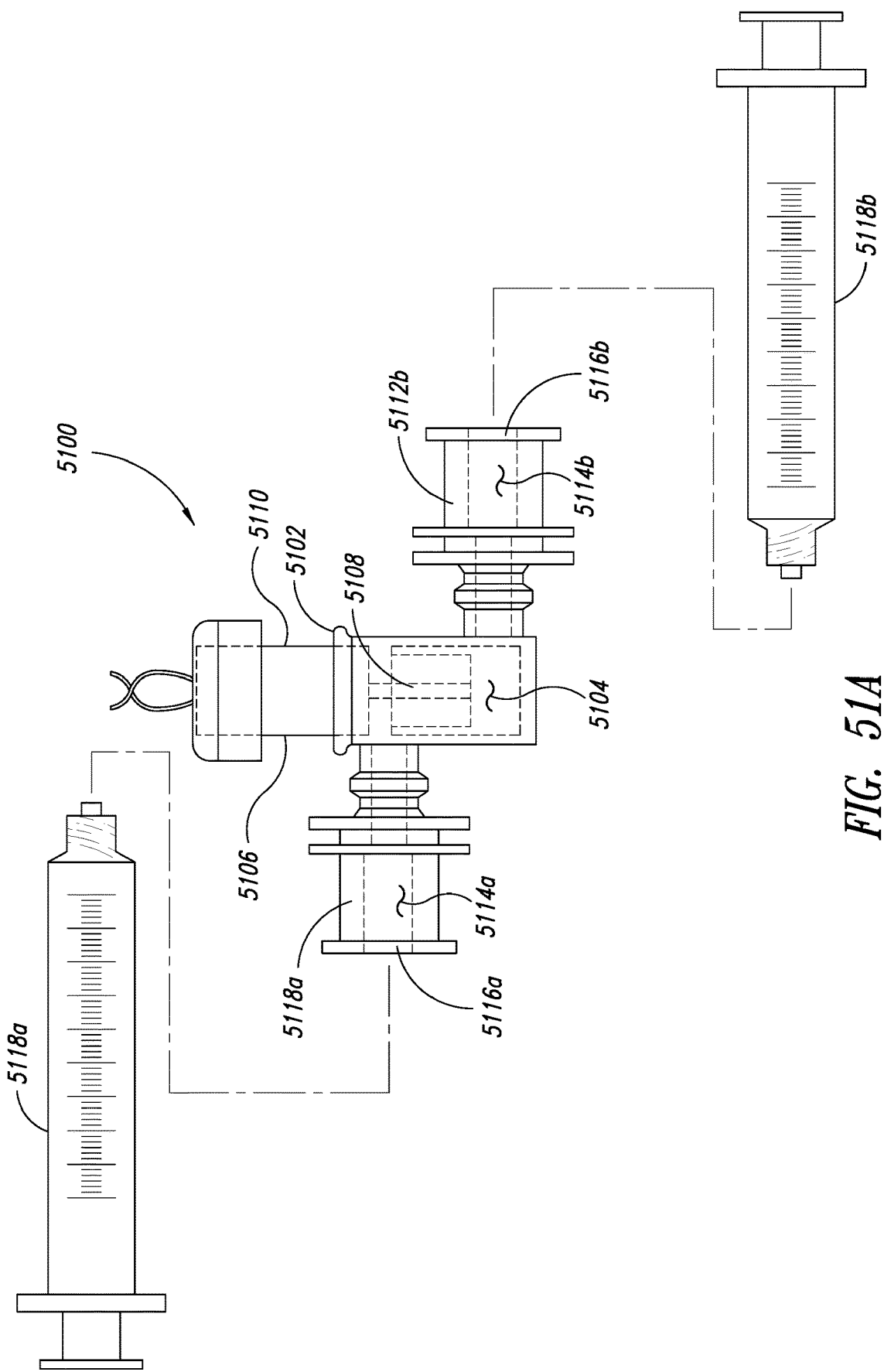
FIG. 51A is a plan view of a lysing apparatus having Luer-Lock couplers, according to one illustrated embodiment, and two syringes coupleable to the lysing apparatus via the couplers.
Figure 51B:
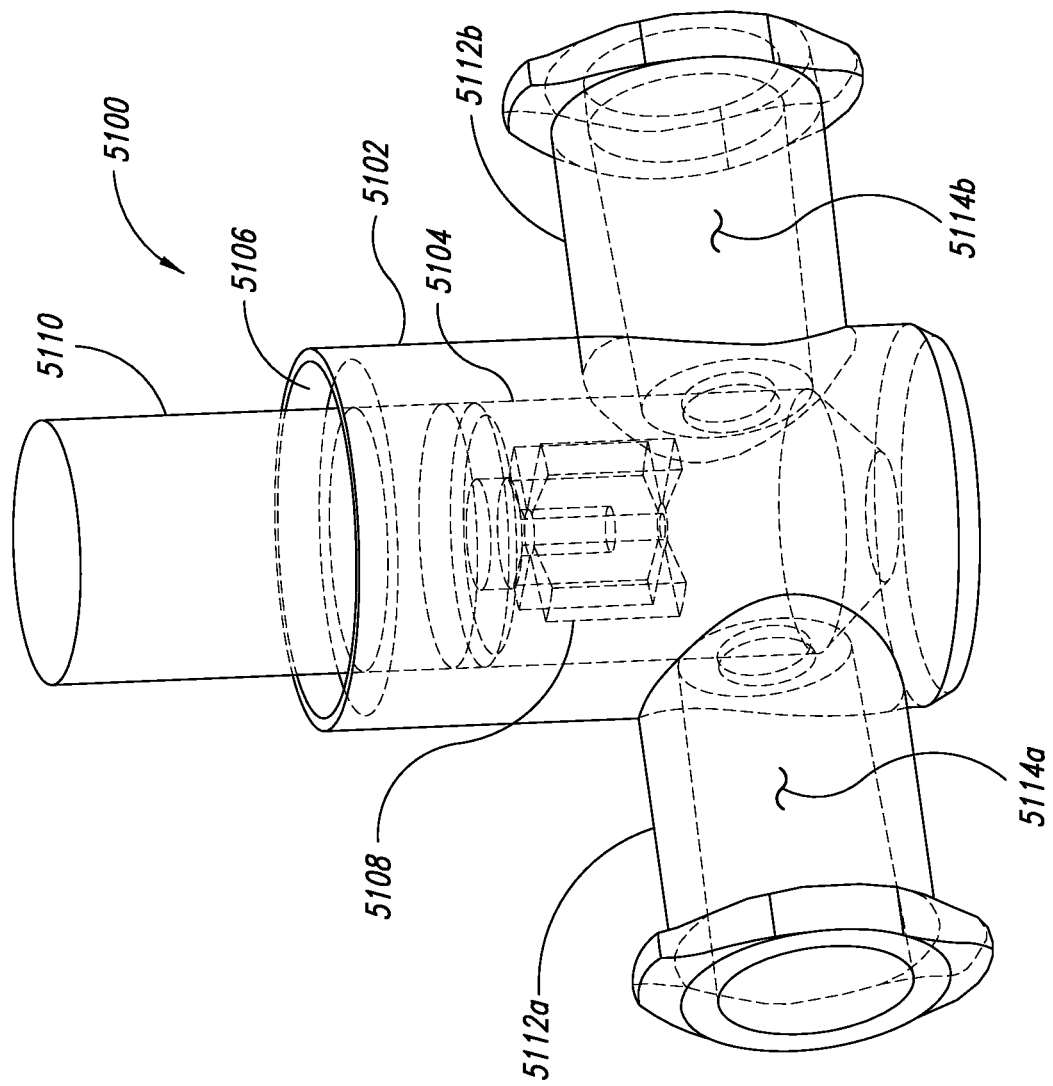
FIG. 51B is an isometric view of the lysing apparatus of FIG. 51A.

FIGS. 51A and 51B show a lysing apparatus 5100, according to another illustrated embodiment.

The lysing apparatus 5100 includes a body 5102 that forms a chamber 5104. The body 5102 may have an opening 5106 sized and dimensioned to receive an impeller 5108 therethrough such that the impeller resides in the chamber 5104. The opening 5106 may optionally receive part or all of a drive motor, for instance a micro electric motor 5110. The electric motor 5110 is coupled to drive the impeller 5108. The electric motor 5110 is selectively operable in response to power supplied thereto. The electric motor 5110 may be secured in the opening 5106 via a press type fitting or interference fit. In particular, an inner wall forming the opening 5106 and/or chamber 5104 may be slightly tapered to sealing engage a side wall of the electric motor 5110 as the electric motor is advanced through the opening 5106 and into the chamber 5104. Alternatively, or additionally, a side wall of the electric motor 5110 may be slightly tapered to sealing engage a side wall of the opening 5106 and/or the chamber 5104 as the electric motor 5110 is advanced through the opening 5106 and into the chamber 5104. Alternatively, the electric motor 5110 and the opening 5106 and/or chamber 5104 may include coupler structures. For instance, the electric motor 5110 and the opening 5106 and/or chamber 5104 may include threads (not shown) which sealing mate together as the electric motor 5110 is advanced through the opening 5106 and into the chamber 5104. Alternatively, a bayonet (not shown) or lug type (not shown) coupler structure may be employed. Other sealing structures may be employed. For example, one or more gaskets, washers or O-rings (not shown) may be employed, with or without a seat or peripheral ring to seat the gasket, washers or O-rings. The seal may be a fluid tight seal and/or a gas tight seal.

The lysing apparatus includes a first port 5112a and a second port 5112b (collectively 5112). The first and second ports 5112 include passages 5114a, 5114b, respectively, (collectively 5114) to provide fluid communication with the chamber from an exterior thereof. The ports 5112 may be used to as input ports to supply material to the chamber 5104 and/or as output ports to remove material from the chamber 5104.

Each port 5112 may have a coupler 5116a, 5116b (collectively 5116) that allows selective coupling to the respective port 5112a, 5112b. For example, each of the ports 5112 may include a respective Luer-Lock® fitting or Luer-Slip® fitting, male or female. The Luer-Lock® or Luer-Taper® fittings allow the coupling of syringes 5118a, 5118b (FIG. 51A, collectively 5118) to the lysing apparatus 5100. For example, a first syringe 5118a may be coupled to the first port 5112a to allow sample or specimen injection, while a second syringe 5118b may be coupled to the second port 5112b to allow removal of a sample or specimen after lysing (i.e., lysed material). Such may allow the passage of a sample or specimen back and forth through the chamber 5104, for instance to enhance performance of the lysing or of DNA capture. Use of syringes 5118 may occur at either port 5112a, 5112b or at both ports 5112. The advantages of using a syringe 5118 as a sample or specimen delivery system include the fact that syringes 5118 are inexpensive, disposable, and employ positive displacement of fluid for a high degree of reliability in rapidly dispensing volumes. The Luer-Lock® design exemplifies a universal attachment that seals reliably and mates with many devices that also have complimentary Luer-Lock® fittings.

As illustrated in FIG. 52, selectively fastenable fittings, such as the Luer-Lock® fittings, may allow multiple lysing apparatus 5100a-5100b (collectively, 5100, only three illustrated) to be connected in succession. Such may advantageously be used to sequentially process a sample or specimen through multiple stages. Additionally, or alternatively, lysing particulate (e.g., beads) in the different sequential lysing apparatus 5100 may each have a respective receptivity for different molecules. For instance, the particulate in successive ones of the sequential lysing apparatus may be conferred with receptors (e.g., binding sites) to capture different respective molecules from the same sample or specimen. Each lysing apparatus 5100 with a different captured molecule, may then be easily separated from one another, and processed individually using different types of elution acts or steps.

Figure 53A:
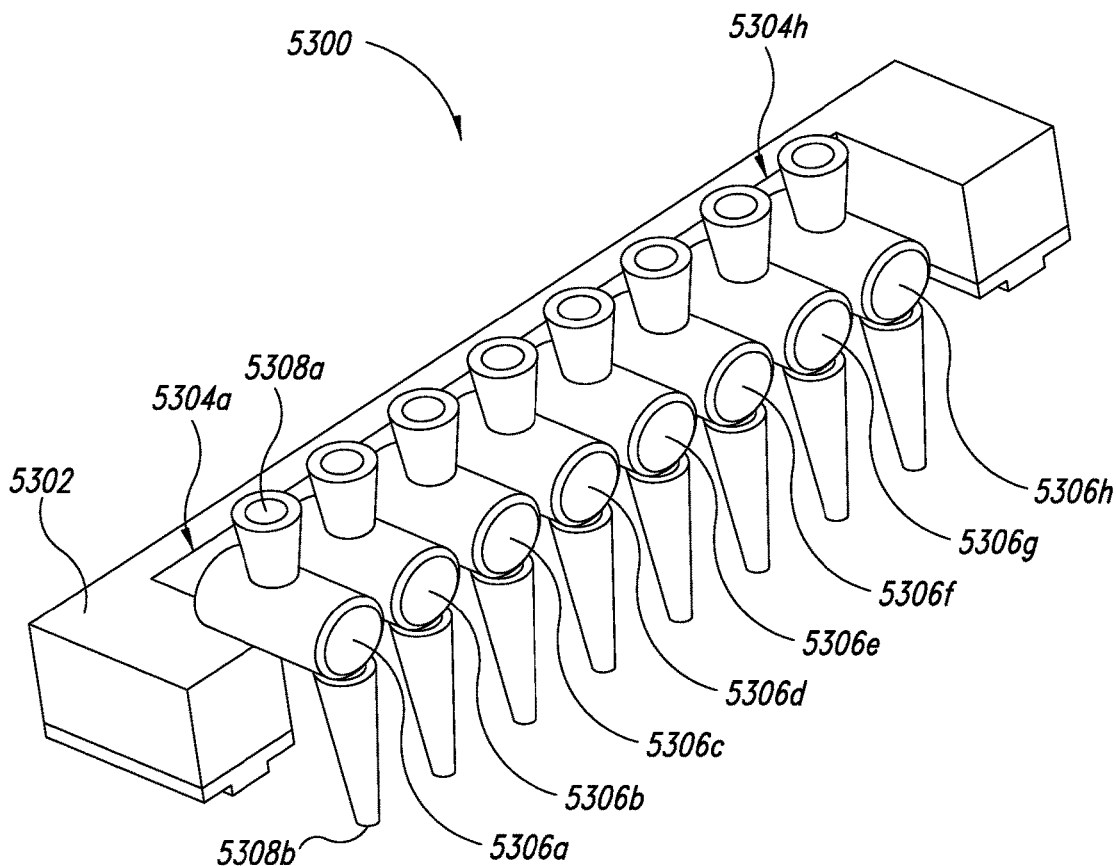
FIG. 53A is an isometric view of a manifold or array of lysing apparatus, according to one illustrated embodiment.
Figure 53B:
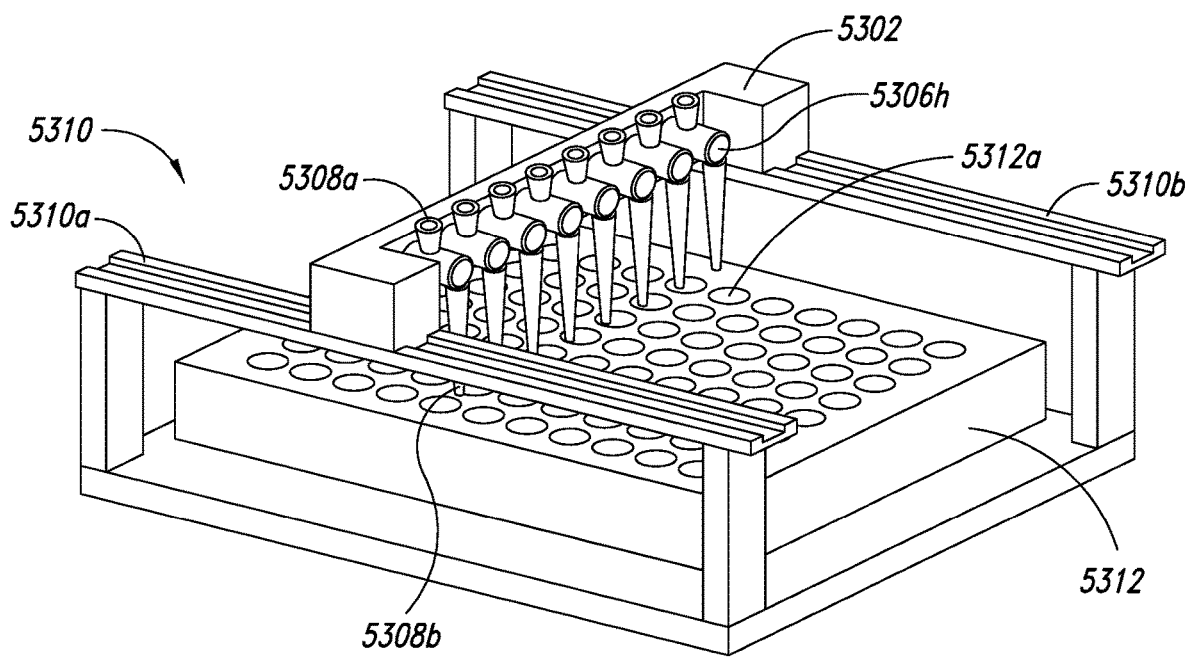
FIG. 53B is an isometric view of the manifold or array of lysing apparatus carried by a frame, according to one illustrated embodiment, the lysing apparatus positioned to deposit lysed material into respective wells of a plate.

FIGS. 53A and 53B show a lysing manifold or array 5300, according to one illustrated embodiment. The lysing manifold or array 5300 includes a block or frame 5302 that has a plurality of positions 5304a, 5304h (collectively 5304, only two called out in FIG. 53A) to hold respective ones of one or more individual lysing apparatus 5306a-5306h (collectively 5306, six illustrated). The individual lysing apparatus 5306 may, for example, take the form of distinct lysing apparatus which employ a chamber that receives an impeller and electric motor, for instance, the individual lysing apparatus 53006 may be identical or similar to the lysing apparatus 5100 (FIG. 51). Each individual lysing apparatus 5306 may include a respective disposable electric motor coupled to drive the impeller. Each individual lysing apparatus 5306 may include a first port 5308a and a second port 5308b (collectively 5308, only two called out in FIG. 53A). The ports 5308 may function as inlet and/or outlets to a chamber (not called out in FIG. 53A or 53B).

As illustrated in FIG. 53B, the lysing manifold or array 5300 may include a support structure 5310 to support one or more blocks or frames 5302 and associated individual lysing apparatus 5306. In particular, the support structure 5310 may include rails 5310a, 5310b to hold the block or frame 5302 and associated individual lysing apparatus 5306 positioned relative to a structure that receives the lysed material, for example a plate such as a micro-titer plate 5312. For instance, the support structure 5310 may hold the block or frame 5302 such that the associated individual lysing apparatus 5306 are positioned above respective ones of a plurality of wells 5312a (only one called out in FIG. 53B) of the micro-titer plate 5312. FIG. 53B shows only a single lysing manifold or array 5300 carrying a single row of individual lysing apparatus 5306, constituting a one-dimensional array of lying apparatus 5306. Alternatively, the support structure 5310 may carry additional lysing manifolds or arrays, each carrying a respective single row of individual lysing apparatus 5306. The individual lysing apparatus 5306 carried by the plurality of lysing manifolds or arrays 5300 can constitute a two-dimension array. As a further alternative, a single lysing manifold or array 5300 may carry individual lysing apparatus 5306 arranged in a two-dimensional array. As an even further alternatively, a motor and drive mechanism may be coupled to move a single lysing manifold or array 5300 carrying the individual lysing apparatus 5306 along the rails 5310a, 5310b of the support structure 5310. Thus, the one-dimensional array of lysing apparatus 5306 may be moved to address a two-dimensional array of positions. Movement may be controlled manually or automatically, for example via one or more computer processors.

As described immediately above, individual lysing apparatus 5306 can be bundled together into a lysing manifold or array 5300 (e.g., one- or two dimensions) to facilitate multiplex processing. The distance between centers for these individual lysing apparatus 5306 can, for example, be 9 mm or a multiple of 9 mm to match a standard format of a micro-titer plate 5312 (e.g., with 9 mm spacing, 96 well plate or greater). Similarly, the use of electric motors with diameters below 4.5 mm allows the manifold or array of lysing apparatus 5300 to be used for micro-titer plate formats with 4.5 mm spacing (e.g., 384 well plate). Bundling the individual lysing apparatus 5306 in strips or rows of 4, 8, 6 or 12 may facilitate use for automated or semi-automated processing of samples in a micro-titer format. Additionally, if intake ports 5308a of the individual lysing apparatus 5306 are designed to receive sample or specimen from pipette tips, then the individual lysing apparatus 5306 may be addressed by multichannel pipettors for either manual or robotic operation. The block or frame 5302 may be fabricated monolithically from a single block of material that has been molded or cut-extruded with multiple sites for the individual lysing apparatus 5306.

Figures 54A, 54B:
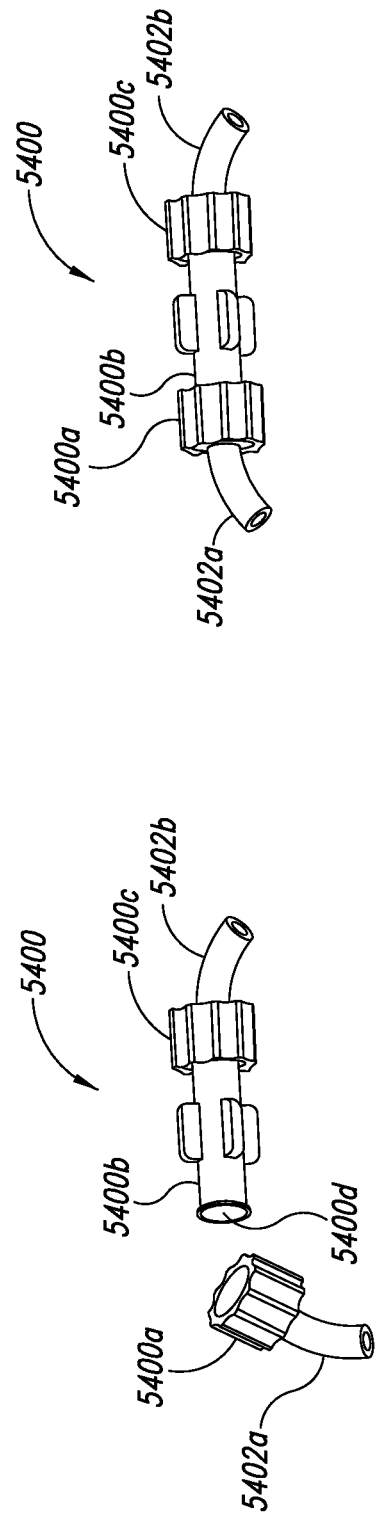
FIG. 54A is an isometric view of a cartridge style container for use in flow through lysing showing an end cap removed from a body of the cartridge style container, according to one illustrated embodiment.
FIG. 54B is an isometric view of the cartridge style container of FIG. 54A with the end cap secured to a body of the cartridge style container.
Figure 56B:
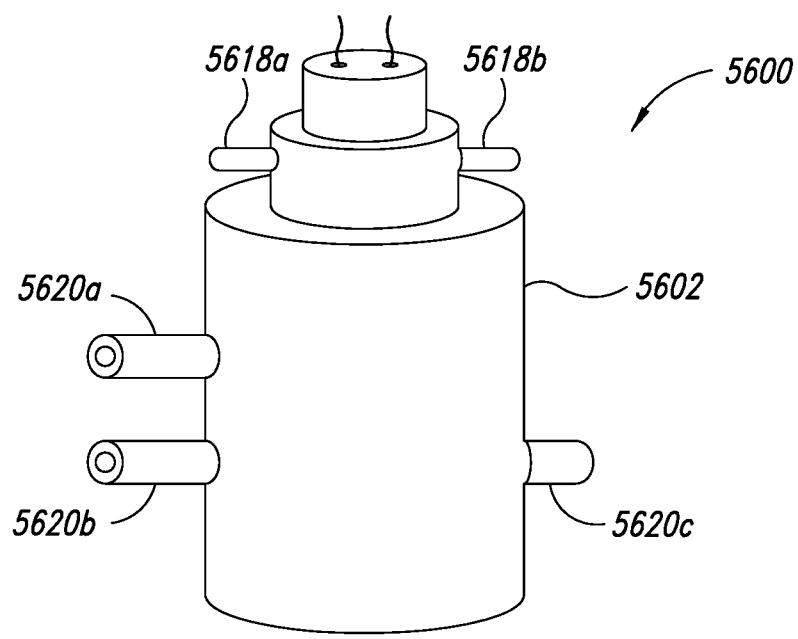
FIG. 56B is an isometric view of a stopcock style lysing device of FIG. 56A, showing an inner vessel received in an outer vessel, and an drive device including a motor and impeller received in the inner vessel.
Figure 57B:
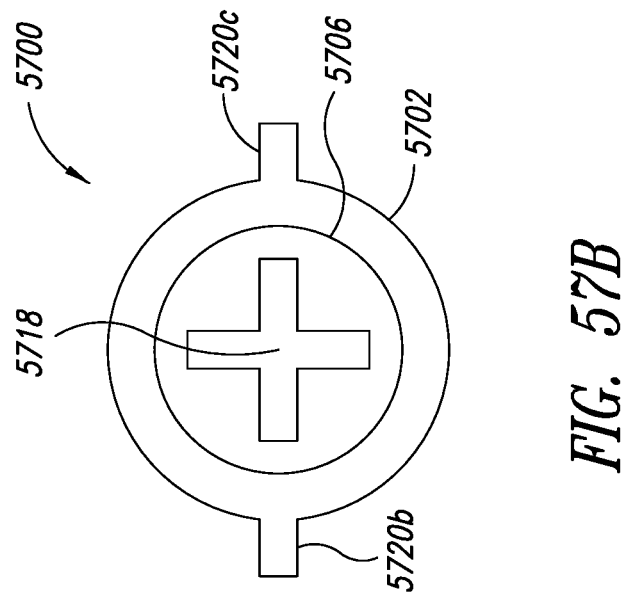
FIG. 57B is a bottom plan view of a stopcock style lysing device of FIG. 57A.
Figure 57A:
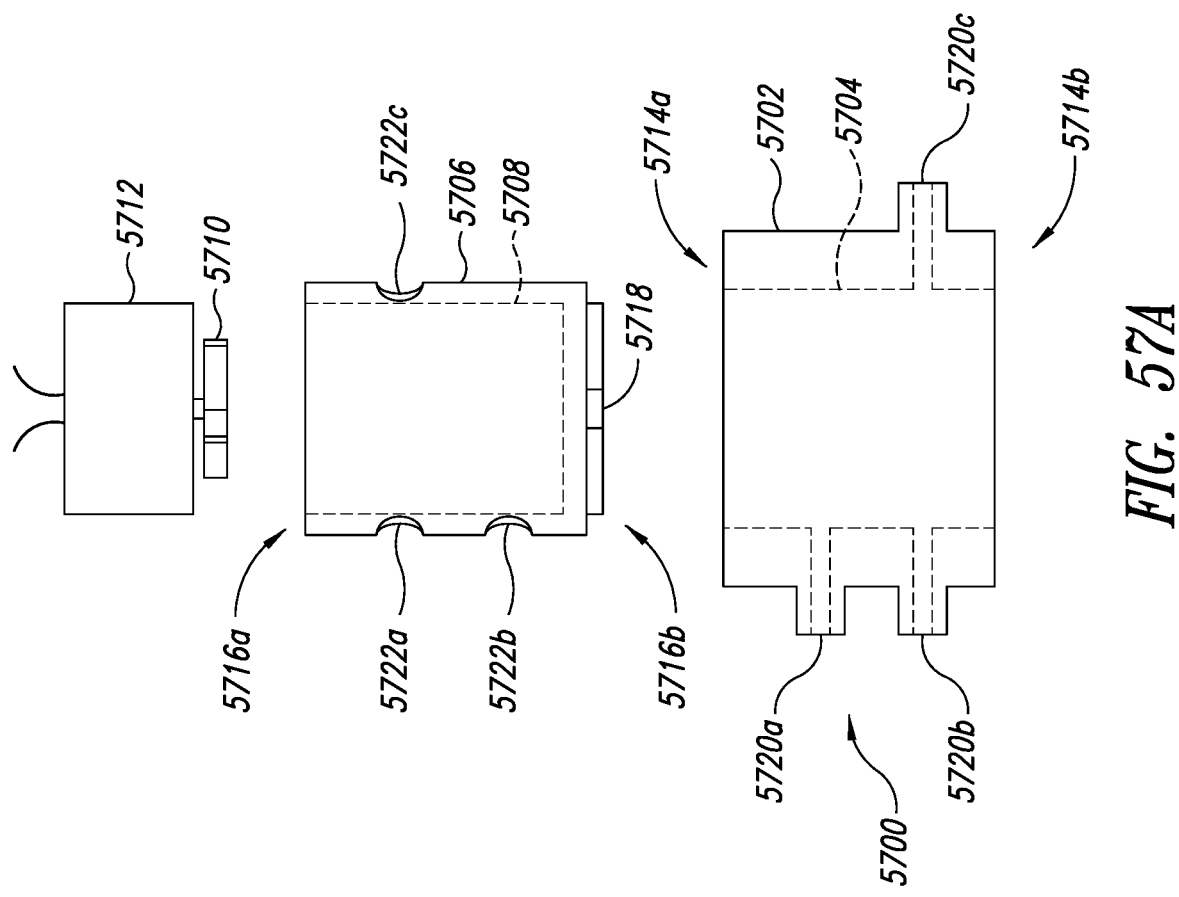
FIG. 57A is an exploded side elevational view of a stopcock style lysing device, according to another illustrated embodiment, showing an inner vessel with a closed bottom portion.

FIGS. 54A and 54B show a cartridge style container 5400 configured to perform flow through lysis processing, according to one illustrated embodiment. In particular, FIG. 54A shows the container 5400 with one end cap 5400a removed to provide access to a chamber (not called out in FIG. 54A or 54B) formed by a body 5400b of the container 5400, and the other end cap 5400c fixed to the body 5400b. FIG. 54B shows the container 5400 with both end caps 5400a, 5400c fastened to the body 5400b of the container 5400. The cartridge style container 5404 may, for example, be employed with the oscillating arcuate motion based apparatus (FIGS. 1-5), sometimes referred to herein as a bead beater.

The body 5400b of the container 5400 may have openings 5400d (only one illustrated, in FIG. 54A) at opposed ends 5400e, 5400f thereof, providing access to the chamber formed by the body 5400b of the container 5400. These openings 5400d may be relatively large to accommodate samples or specimens in various states. As noted above, at least one end cap 5400a, 5400b of the container 5400 is selectively removable from the body 5400b of the container 5400. Such provides access to the interior of the chamber for relatively large samples or specimens. In some embodiments, both end caps 5400a, 5400c are selectively removable and fastenable to the body 5400b of the container 5400, while in other embodiments only one end cap 5400a, 5400c may be removable. In such embodiments, the other end cap 5400a, 5400c may be a monolithic portion of the body 5400b, or may be permanently secured thereto, for example via an adhesive, heat sealing or radio frequency (RF) welding.

Each of the end caps 5400a, 5400c may include a respective port 5402a, 5402b (collectively 5402) that provides fluid communication to the interior chamber of the body 5400b from an exterior thereof. Such may accommodate flow through operation.

The cartridge style container 5400 and flow through lysing operation may be used on virtually any cell type, for example plants, bacteria, spores, yeast, invertebrates and vertebrates. Additionally, the re-closable end caps 5400a, 5400c advantageously allows the placement of a piece of sample tissue in the chamber, while maintaining flow through capability after the end cap 5400a, 5400c is fastened to close the chamber. This may allow the lysing apparatus to function as a homogenizer of tissues, for instance biopsy samples, mouse tail slices, leaf punches, seeds, etc. Such may eliminate the need to precede cell lysis with a separate tissue homogenization act or step, which would otherwise typically require a separate piece of equipment.

A small disposable electric motor, such as that used to mix the beads in the embodiment employing an impeller received in a chamber of bead blender (e.g., FIG. 16), may also be used for other integrated functions related to analytical biochemistry. For example, such small disposable electric motors may be used as part of, but not limited to, a pump, a reversible pump, a valve, a mixer of reagents, a micro centrifuge, etc. Such disposable electric motors may even perform these functions in combination with performing other functions, such as, but not limited to, lysing cells in the presence of lysing particulate or beads, while pumping fluid (e.g., material to be lysed, lysed material, cleansers) at the same time. For example, a pump may comprises an assay device with impeller and a disposable electric motor, such as illustrated in FIG. 16, with a check valve on either or both ports. The check valve(s) direct flow in one direction, while the fluid is driven by motion the motor imparts to the fluid via the impeller.

In both configurations (i.e., lysing apparatus with rapidly oscillating arcuate motion sometimes referred to herein as bead beating or lysing apparatus with high angular velocity impeller sometimes referred to herein as bead blender), high energy is imparted to the fluid, in turn causing high velocities of lysing particulate or beads relative to each other, which in turn causes high shear forces between lysing particulate or beads as they pass by relative to each other. Not to be limited by theory, these shear forces are a possible explanation for surprising ultra rapid lysis of the cells. Other configurations that impart similar shear forces between the lysing particulate or beads may also provide rapid cell lysing.

The flow through nature of some embodiments may allow for reuse of the system for processing additional samples or specimens. For example, the flow through nature may facilitate performance of one or more wash acts or steps to sterilize or otherwise sanitize or cleanse the system. Containers may be reused by cleaning and/or sterilizing the container between uses. This may be coordinated with downstream processing of one sample or specimen such that the container may be made ready for another sample or specimen during the downstream processing. One or more acts may be employed to clean and/or sterilize the container, for example using a high pH or low pH solution, bleach, detergent or combinations thereof. Adjusting pH may advantageously reduce the number of wash acts or steps, since the pH can be easily neutralized. An alternative approach may be the use of di-ethyl-pyrocarbonate (DEPC). DEPC compound can destroy proteins and nucleic acid. This treatment may be followed by a single wash and then a flow of hot air. Because DEPC is so volatile, it may be removed by degradation and evaporation during the act of passing heated air over any surfaces treated with the DEPC.

Lysis efficiency or cell disruption appears to be affected by the ratio of particulate or bead volume to chamber volume. Higher efficiency appears to occur when the volume of lysing particulate or beads is greater than 50% of the volume of the chamber, with an upper limit. Not to be limited by theory, the assumption is that a denser population of lysing particulate or beads leads to a higher rate of collisions and/or a higher rate of proximal passes between lysing particulate or beads with high shear force, thereby increasing the efficiency of lysis. Clearly, this advantage diminishes when the lysing particulate or beads are packed too densely to move or are too dense to permit the electric motor to function (e.g. over packed in bead blender apparatus). In theory, the ratio of chamber volume to lysing particulate or bead volume for both the oscillating arcuate motion based apparatus (i.e., bead beater) and the rotational impeller based apparatus (i.e., bead blender) can be any number, but higher efficiencies will occur when the ratio is greater than 1 to 1.

Lysis efficiency appears to be affected by a ratio of the volume of the lysis chamber to the volume of fluid in the lysis chamber. The high energy methods of lysis of cells by mechanical means with lysis particulate or beads such as by rapid oscillation of the chamber or fast rotation of a vane (i.e., impeller) are primarily designed to fill the lysis chamber entirely with fluid. It is possible to include a gap of air in the chamber during lysis, however doing so will disadvantageously reduce lysis efficiency as the air gap is increased. This approach of allowing an air gap tends to generate heat. However, the heat may advantageously be used to further denature components of the sample matrix or assist in elution of captured analyte. For example, in the case of capture of DNA by sequence specific capture probes, the heat generated by lysing in the presence of an air gap or pocket may be used to enhance the release and elution of DNA from the capture probes.

The various embodiments described above can be combined to provide further embodiments. U.S. provisional patent application Ser. No. 61/020,072 filed Jan. 9, 2008; International Patent Application Ser. No. PCT/US2009/030622 filed Jan. 9, 2009 and published as WO 2009/089466; U.S. provisional patent application Ser. No. 61/117,012 filed Nov. 21, 2008; U.S. provisional patent application Ser. No. 61/220,984 filed Jun. 26, 2009; U.S. provisional patent application Ser. No. 61/317,604, filed Mar. 25, 2010; U.S. non-provisional application Ser. No. 12/732,070, filed Mar. 25, 2010; U.S. non-provisional application Ser. No. 14/451,015, filed Aug. 4, 2014 and U.S. non-provisional application Ser. No. 15/299,059, filed Oct. 20, 2016 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of performing lysis, the method comprising:
providing a lysing apparatus that includes:
a container having at least one chamber, the container including a first opening that provides fluid communication into the chamber from an exterior thereof;
an impeller having a number of blades positionable in the chamber of the container; and
a micromotor coupled to turn the impeller;
receiving a material to be lysed and a lysing particulate material in the chamber of the container;
removably positioning at least a portion of the micromotor in the first opening of the container to seal the first opening, wherein, when the micromotor is so positioned, the impeller is positioned in the chamber of the container; and
causing the micromotor to drive the impeller to circulate the material to be lysed and the lysing particulate material in the chamber of the container.

2. The method of claim 1 wherein receiving the material to be lysed and the lysing particulate material in the chamber comprises receiving the material to be lysed and the lysing particulate material in the chamber via the first opening.

3. The method of claim 1 wherein the container comprises a second opening positioned above the first opening, the second opening provides fluid communication into the chamber from the exterior thereof, and receiving the material to be lysed and the lysing particulate material in the chamber comprises receiving the material to be lysed and the lysing particulate material in the chamber via the second opening.

4. The method of claim 1 the first opening is the only opening in the container, and receiving the material to be lysed and the lysing particulate material in the chamber comprises receiving the material to be lysed and the lysing particulate material in the chamber via the first opening.

5. The method of claim 1 wherein providing a lysing apparatus comprises providing a lysing apparatus that is one lysing apparatus of a plurality of lysing apparatuses spaced apart from each other in a one-dimensional array or a two-dimensional array.

6. The method of claim 1 wherein causing the micromotor to drive the impeller comprises causing the micromotor to pulsate.

7. The method of claim 1 wherein causing the micromotor to drive the impeller comprises causing the micromotor to drive the impeller at a rate of greater than 10,000 RPM.

8. The method of claim 1, further comprising:
removing the micromotor from first opening of the container; and
removing material that has been lysed from the chamber of the container.

9. The method of claim 8 wherein removing the material that has been lysed comprises removing the material that has been lysed via the first opening of the container.

10. The method of claim 8 wherein the container comprises a second opening positioned above the first opening, the second opening provides fluid communication into the chamber from the exterior thereof, and removing the material that has been lysed comprises removing the material that has been lysed via the second opening of the container.

* * * * *